United States Patent
Gibson et al.

(10) Patent No.: US 7,880,031 B2
(45) Date of Patent: *Feb. 1, 2011

(54) PROCESS TO PRODUCE AN ENRICHMENT FEED

(75) Inventors: Philip Edward Gibson, Kingsport, TN (US); Kenny Randolph Parker, Afton, TN (US)

(73) Assignee: Eastman Chemical Company, Kingsport, TN (US)

( * ) Notice: Subject to any disclaimer, the term of this patent is extended or adjusted under 35 U.S.C. 154(b) by 1034 days.

This patent is subject to a terminal disclaimer.

(21) Appl. No.: 11/365,117

(22) Filed: Mar. 1, 2006

(65) Prior Publication Data

US 2006/0264661 A1    Nov. 23, 2006

Related U.S. Application Data

(60) Provisional application No. 60/682,764, filed on May 19, 2005.

(51) Int. Cl.
    *C07C 51/16*    (2006.01)
(52) U.S. Cl. .................. 562/409; 562/412; 562/414
(58) Field of Classification Search ............... None
    See application file for complete search history.

(56) References Cited

U.S. PATENT DOCUMENTS

| | | |
|---|---|---|
| 2,829,153 A | 4/1958 | Vodonik |
| 2,905,707 A | 9/1959 | Hurt et al. |
| 2,959,839 A | 11/1960 | Craig |
| 3,054,776 A | 9/1962 | Higgins |
| 3,118,843 A | 1/1964 | Stuetzer |
| 3,170,768 A | 2/1965 | Baldwin |
| 3,385,881 A | 5/1968 | Bachmann et al. |
| 3,452,088 A | 6/1969 | Baldwin et al. |
| 3,507,913 A | 4/1970 | Motoo et al. |
| 3,582,244 A | 6/1971 | Siclari et al. |
| 3,600,137 A | 8/1971 | Girantet et al. |
| 3,644,096 A | 2/1972 | Lewis et al. |
| 3,647,740 A | 3/1972 | McCall |
| 3,689,461 A | 9/1972 | Balint et al. |
| 3,819,585 A | 6/1974 | Funk et al. |
| 3,839,436 A | 10/1974 | Longland |

(Continued)

FOREIGN PATENT DOCUMENTS

CA    2248288    8/1997

(Continued)

OTHER PUBLICATIONS

USPTO Office Action dated Dec. 31, 2007 for copending U.S. Appl. No. 11/365,652.

(Continued)

*Primary Examiner*—Karl J Puttlitz
(74) *Attorney, Agent, or Firm*—Steven A. Owen; Bernard J. Graves, Jr.

(57) ABSTRACT

A process is provided for producing an enriched carboxylic acid compositions produced by contacting composition comprising a carboxylic acid with an enrichment feed in an enrichment zone to form an enriched carboxylic acid composition. This invention also relates to a process and the resulting compositions for removing catalyst from a carboxylic acid composition to produce a post catalyst removal composition.

9 Claims, 22 Drawing Sheets

U.S. PATENT DOCUMENTS

| | | | |
|---|---|---|---|
| 3,929,684 | A | 12/1975 | Einberg |
| 3,931,305 | A | 1/1976 | Fisher |
| 3,996,271 | A | 12/1976 | Yokota et al. |
| 4,110,316 | A | 8/1978 | Edging et al. |
| 4,158,738 | A | 6/1979 | Scott et al. |
| 4,185,073 | A | 1/1980 | Marsh et al. |
| 4,212,991 | A | 7/1980 | Choulet et al. |
| 4,219,669 | A | 8/1980 | Tsuchiya et al. |
| 4,230,818 | A | 10/1980 | Broughton, Jr. et al. |
| 4,235,844 | A | 11/1980 | Sterzel et al. |
| 4,286,101 | A | 8/1981 | Hashizume et al. |
| 4,289,895 | A | 9/1981 | Burkhardt et al. |
| 4,356,319 | A | 10/1982 | Roffia et al. |
| 4,357,475 | A | 11/1982 | Hanotier et al. |
| 4,391,985 | A | 7/1983 | Hook et al. |
| 4,613,678 | A | 9/1986 | Swart |
| 4,670,587 | A | 6/1987 | Saska |
| 4,772,748 | A | 9/1988 | Hashizume et al. |
| 4,782,181 | A | 11/1988 | James |
| 4,827,025 | A | 5/1989 | Shiraki et al. |
| 4,939,297 | A | 7/1990 | Browder et al. |
| 4,992,580 | A | 2/1991 | Partenheimer |
| 5,095,146 | A | 3/1992 | Zeitlin et al. |
| 5,166,420 | A | 11/1992 | Shiraki et al. |
| 5,175,355 | A | 12/1992 | Streich et al. |
| 5,254,288 | A | 10/1993 | Verheijen et al. |
| 5,359,133 | A | 10/1994 | Nazimok et al. |
| 5,527,957 | A | 6/1996 | Hindmarsh et al. |
| 5,596,129 | A | 1/1997 | Murashige et al. |
| 5,696,285 | A | 12/1997 | Roby |
| 5,767,311 | A | 6/1998 | Lee et al. |
| 5,840,965 | A | 11/1998 | Turner et al. |
| 5,840,968 | A | 11/1998 | Lee et al. |
| 5,877,346 | A | 3/1999 | Hindmarsh et al. |
| 6,013,835 | A | 1/2000 | Lee et al. |
| 6,025,061 | A | 2/2000 | Khanarian et al. |
| 6,133,476 | A | 10/2000 | Lin |
| 6,265,608 | B1 | 7/2001 | Sumner, Jr. et al. |
| 6,291,707 | B1 | 9/2001 | Lin |
| 6,307,099 | B1 | 10/2001 | Turner et al. |
| 6,355,835 | B1 | 3/2002 | Kulsrestha et al. |
| 6,392,091 | B2 | 5/2002 | Lin |
| 6,417,269 | B1 | 7/2002 | Murray et al. |
| 6,544,611 | B2 | 4/2003 | Schiraldi et al. |
| 6,562,996 | B2 | 5/2003 | Saleh |
| 6,639,104 | B2 | 10/2003 | Piras et al. |
| 6,765,113 | B2 | 7/2004 | Graham et al. |
| 7,132,566 | B2 | 11/2006 | Sumner et al. |
| 7,273,559 | B2 | 9/2007 | Gibson et al. |
| 7,282,151 | B2 | 10/2007 | Parker et al. |
| 7,291,270 | B2 | 11/2007 | Gibson et al. |
| 2002/0193630 | A1 | 12/2002 | Lin et al. |
| 2003/0091774 | A1 | 5/2003 | Tyler et al. |
| 2004/0073059 | A1 | 4/2004 | Lin |
| 2004/0110981 | A1 | 6/2004 | Sheppard et al. |
| 2004/0249208 | A1* | 12/2004 | Lin et al. ............ 562/600 |
| 2005/0065373 | A1 | 3/2005 | Sumner et al. |
| 2005/0154179 | A1 | 7/2005 | Lin |
| 2005/0159578 | A1 | 7/2005 | Parker et al. |

FOREIGN PATENT DOCUMENTS

| | | |
|---|---|---|
| DE | 12 42 212 B | 6/1967 |
| DE | 29 42 375 A1 | 4/1980 |
| EP | 0 502 628 B1 | 10/1996 |
| EP | 0 579 716 B1 | 8/1997 |
| EP | 1 484 305 A1 | 12/2004 |
| EP | 1 484 306 A1 | 12/2004 |
| JP | 47-34992 A | 11/1972 |
| WO | WO 93/24441 | 12/1993 |
| WO | 9730963 * | 8/1997 |
| WO | 9730963 A1 | 8/1997 |
| WO | WO 02/098836 A1 | 12/2002 |
| WO | WO 03/016252 A2 | 2/2003 |
| WO | WO 2004/052822 A1 | 6/2004 |
| WO | WO2004052820 A1 | 6/2004 |
| WO | WO 2006/007348 A1 | 1/2006 |
| WO | WO 2006/028818 A1 | 3/2006 |
| WO | 2006049818 * | 5/2006 |
| WO | 2006049818 A1 | 5/2006 |
| WO | WO 2006/088470 A2 | 8/2006 |
| WO | 2006125144 A1 | 11/2006 |

OTHER PUBLICATIONS

USPTO Office Action dated Jan. 2, 2008 for copending U.S. Appl. No. 11/365,256.
USPTO Office Action dated Feb. 17, 2009 for copending U.S. Appl. No. 11/365,055.
USPTO office action dated Feb. 28, 2007 for copending U.S. Appl. No. 11/365,440.
Copending U.S. Appl. No. 11/705,218, filed Feb. 12, 2007, Kenny R. Parker et al.
USPTO Office Action dated Mar. 25, 2008 for copending U.S. Appl. No. 11/365,054.
USPTO Office Action dated Jun. 25, 2007 for copending U.S. Appl. No. 11/365,054.
USPTO Notice of Allowance dated Aug. 15, 2008 for copending U.S. Appl. No. 11/365,256.
Copending U.S. Appl. No. 11/845,269, filed Aug. 27, 2007, Philip Edward Gibson, et al.
USPTO Notice of Allowance dated Sep. 13, 2007 for copending U.S. Appl. No. 11/365,440.
USPTO Office Action dated Sep. 22, 2008 for copending U.S. Appl. No. 11/365,652.
Copending U.S. Appl. No. 12/244,109, filed Oct. 2, 2008, Kenny Randolph Parker, et al.
USPTO Office Action dated Oct. 20, 2008 for copending U.S. Appl. No. 11/365,054.
Copending U.S. Appl. No. 11/365,055, filed Mar. 1, 2006.
Copending U.S. Appl. No. 11/365,080, filed Mar. 1, 2006.
Copending U.S. Appl. No. 11/365,255, filed Mar. 1, 2006.
Copending U.S. Appl. No. 11/365,439, filed Mar. 1, 2006.
Copending U.S. Appl. No. 11/365,054, filed Mar. 1, 2006.
Copending U.S. Appl. No. 11/365,079, filed Mar. 1, 2006.
Copending U.S. Appl. No. 11/365,074, filed Mar. 1, 2006.
Copending U.S. Appl. No. 11/365,440, filed Mar. 1, 2006.
Copending U.S. Appl. No. 11/365,652, filed Mar. 1, 2006.
Copending U.S. Appl. No. 11/365,256, filed Mar. 1, 2006.
USPTO Office Action dated Dec. 12, 2008 for copending U.S. Appl. No. 11/365,074.
USPTO Office Action dated Apr. 7, 2009 for copending U.S. Appl. No. 11/365,080.
USPTO Office Action dated May 13, 2009 for copending U.S. Appl. No. 11/705,218.
USPTO Notice of Allowance dated May 13, 2009 for copending U.S. Appl. No. 11/365,652.
USPTO Office Action dated May 27, 2009 for copending U.S. Appl. No. 11/365,054.
USPTO Office Action dated Jun. 2, 2009 for copending U.S. Appl. No. 11/365,255.
New copending U.S. Appl. No. 12/492,246, filed Jun. 26, 2009, Philip Edward Gibson, et al.
New copending U.S. Appl. No. 12/492,248, filed Jun. 26, 2009, Philip Edward Gibson, et al.
USPTO Office Action dated Aug. 19, 2009 for copending U.S. Appl. No. 11/365,439.
USPTO Office Action dated Oct. 20, 2009 for copending U.S. Appl. No. 11/365,074.
USPTO Office Action dated Oct. 23, 2009 for copending U.S. Appl. No. 12/244,109.
USPTO Office Action dated Nov. 16, 2009 for copending U.S. Appl. No. 11/365,055.

USPTO Office Action dated Jan. 14, 2010 for copending U.S. Appl. No. 11/705,218.
USPTO Office Action dated Jan. 15, 2010 for copending U.S. Appl. No. 11/365,080.
USPTO Office Action dated Jan. 26, 2010 for copending U.S. Appl. No. 11/365,255.
USPTO Office Action dated Mar. 4, 2010 for copending U.S. Appl. No. 11/365,054.
USPTO Office Action dated Apr. 6, 2010 for copending U.S. Appl. No. 12/492,246.
USPTO Notice of Allowance dated Apr. 22, 2010 for copending U.S. Appl. No. 11/365,055.
USPTO Office Action dated Jun. 11, 2010 for copending U.S. Appl. No. 11/845,269.
USPTO Office Action dated Jun. 21, 2010 for copending U.S. Appl. No. 11/365,074.
USPTO Office Action dated Jun. 22, 2010 for copending U.S. Appl. No. 12/244,109.
USPTO Office Action dated Dec. 1, 2009 for copending U.S. Appl. No. 11/365,079.
USPTO Office Action dated Aug. 25, 2010 for copending U.S. Appl. No. 11/705,218.
USPTO Notice of Allowance dated Aug. 31, 2010 for copending U.S. Appl. No. 11/365,080.
USPTO Office Action dated Sep. 17, 2010 for copending U.S. Appl. No. 11/365,074.
USPTO Office Action dated Sep. 21, 2010 for copending U.S. Appl. No. 12/492,248.
USPTO Notice of Allowance dated Nov. 17, 2010 for copending U.S. Appl. No. 11/705,218.
USPTO Notice of Allowance dated Nov. 18, 2010 for copending U.S. Appl. No. 11/365,079.
USPTO Office Action dated Jul. 22, 2010 for copending U.S. Appl. No. 11/365,079.
USPTO Office Action dated Aug. 6, 2010 for copending U.S. Appl. No. 12/244,109.
USPTO Notice of Allowance dated Oct. 29, 2010 for copending U.S. Appl. No. 12/244,109.
USPTO Notice of Allowance dated Nov. 4, 2010 for copending U.S. Appl. No. 12/492,246.
USPTO Office Action dated Mar. 18, 2009 for copending U.S. Appl. No. 11/365,079.

* cited by examiner

US 7,880,031 B2

PROCESS TO PRODUCE AN ENRICHMENT FEED

CROSS-REFERENCE TO RELATED APPLICATIONS

This application claims priority to U.S. Provisional Application Ser. No. 60/682,764, filed on May 19, 2005, the disclosure of which is incorporated herein by reference in its entirety.

FIELD OF INVENTION

This invention relates to a process and resulting enriched carboxylic acid compositions produced by contacting a carboxylic acid composition with an enrichment feed in an enrichment zone to form an enriched carboxylic acid composition. This invention also relates to a process and the resulting compositions for removing catalyst from a cooled carboxylic acid composition.

BACKGROUND OF THE INVENTION

Terephthalic acid is commercially produced by oxidation of paraxylene in the presence of at least one catalyst, such as, for example, Co, Mn, and Br catalyst and a solvent, typically acetic acid. Terephthalic acid is typically made in a manner to remove impurities formed as a result of the oxidation of paraxylene.

Terephthalic acid (TPA) is an intermediate in the production of condensation polymers and copolymers especially polyesters and co-polyesters for plastics, fibers, films, coatings, containers, and other articles. Of particular commercial importance is poly(ethylene terephthalate), referred to as PET, a polyester of TPA and ethylene glycol (EG), as well as related copolyesters. Commercial processes for the manufacture of TPA are often based on the multi-valent transition metal catalyzed oxidation of p-xylene, generally with a bromide promoter in an acetic acid solvent. Due to the limited solubility of TPA in acetic acid under practical oxidation conditions, a slurry of crystalline agglomerate containing primarily TPA is usually formed in the oxidation reactor. Typically, the TPA oxidizer slurry is withdrawn from the reactor, and TPA solids are separated from the oxidizer mother liquor using conventional solid-liquid separation techniques. The oxidizer mother liquor stream, which contains most of the catalyst and promoter used in the process, is recycled to the oxidation reactor. In addition to the catalyst and promoter, the oxidizer mother liquor stream also contains dissolved TPA and many by-products, impurities, and other compounds. These other compounds, oxidation by-products and impurities arise partially from compounds present in minor amounts in the p-xylene feed stream. Other compounds and oxidation by-products arise due to the incomplete oxidation of p-xylene resulting in partially oxidized products. Still other compounds and oxidation by-products result from competing side reactions formed as a result of the oxidation of p-xylene to terephthalic acid. Patents disclosing the production of terephthalic acid such as U.S. Pat. No. 4,158,738 and U.S. Pat. No. 3,996,271 are hereby incorporated by reference in their entirety to the extent that they do not contradict statements herein.

Many of the compounds in the oxidizer mother liquor stream that are recycled are relatively inert to further oxidation, but are not inert to further reaction including decomposition and conversion to other compounds. Such compounds include, for example, isophthalic acid (IPA), benzoic acid, and phthalic acid. Compounds in the oxidizer mother liquor stream, which may undergo further oxidation are also present, such as, for example in the case of oxidation of p-xylene (also known as 1,4-dimethylbenzene), compounds such as 4-carboxybenzaldehyde, p-toluic acid, p-tolualdehyde and terephthaldehyde. Compounds that are relatively inert to oxidation and are not otherwise removed from the process tend to accumulate in the oxidizer mother liquor stream upon recycle.

Conventionally, crude terephthalic acid (CTA) is purified either by conversion to a dimethyl ester or by dissolution in water with subsequent hydrogenation over standard hydrogenation catalysts. More recently, secondary oxidative treatments instead of hydrogenation have been used to produce polymer-grade TPA. It is desirable to minimize the concentration of impurities in the mother liquor and thereby facilitate subsequent purification of TPA. In some cases, it is not possible to produce a purified, polymer-grade TPA unless some means for removing impurities from the oxidizer mother liquor stream is utilized.

One technique for impurity removal commonly used in the chemical processing industry is to draw out or "purge" some portion of the mother liquor stream as a recycle stream. Typically, the purge stream is simply disposed of or, if economically justified, subjected to various treatments to remove undesired impurities while recovering valuable components. One example of this purge process is U.S. Pat. No. 4,939,297 herein incorporated by reference in its entirety to the extent that it does not contradict statements herein.

The purification of CTA to produce purified terephthalic acid (PTA) increases the manufacturing cost of the PTA. It is desirable to maximize the concentration of by-products, impurities, and other compounds in the terephthalic acid to the extent that the terephthalic acid remains useful, especially in making poly(ethylene terephthalate) (PET) polymer and articles therefrom, such as, film, containers, and fiber.

One example of utility is the improved yield in a carboxylic acid process, particularly a terephthalic acid process. Another utility of this invention is the flexibility of controlling the destination of specific compounds in the process. For example, a portion of specific compounds can be retained on the product in a catalyst removal zone, and or enriched in the product in the enrichment zones such that they go out with the product stream, or are allowed to exit the process. Yet another utility is the process allows the option of placing compounds on the product stream that are not in the TPA process. Another utility is the option of adding a comonomer, to the TPA product stream, for example, IPA, can be added.

SUMMARY OF THE INVENTION

In a first embodiment of this invention, a process to produce an enrichment feed is provided. The process comprises:
  (a) subjecting a catalyst rich liquor to a cooling and/or concentration zone to form a concentrated mother liquor stream;
  (b) subjecting at least a portion of the concentrated mother liquor stream and an extraction solvent to an extraction zone to form a catalyst depleted stream;
  (c) subjecting the balance of the concentrated mother liquor stream not sent to the extraction zone and a wash stream to a SLS zone to form a wet cake stream; and
  (d) subjecting at least a portion of the wet cake stream and optionally the catalyst depleted stream to a mix zone to form the enrichment feed.

In another embodiment of this invention, a process to produce an enrichment feed is provided. The process comprises:

(a) subjecting at least one stream selected from the group consisting of a cooled carboxylic acid composition, a crystallized slurry composition, a slurry composition, and a crude carboxylic acid composition; a wash feed; and optionally an enrichment feed to a catalyst removal zone to form a post catalyst removal composition, a catalyst rich liquor and optionally a depleted enrichment feed; wherein the wash feed is at a temperature ranging from about 5° C. to about 195° C.; wherein the post catalyst removal composition has a catalyst composition of less than 500 ppm; wherein the catalyst removal zone has a wash ratio between about 0.2 and about 6.0;

(b) subjecting the catalyst rich liquor to a cooling and/or concentration zone to form a concentrated mother liquor stream;

(c) subjecting at least a portion of the concentrated mother liquor stream and an extraction solvent to an extraction zone to form a catalyst depleted stream; and (d) subjecting the balance of the concentrated mother liquor stream not sent to the extraction zone and a wash stream to a SLS zone to form a wet cake stream; wherein the wet cake stream is suitable for use as an enrichment feed.

In another embodiment of this invention, a process to produce an enrichment feed is provided. The process comprises:

(a) subjecting at least one stream selected from the group consisting of a cooled carboxylic acid composition, a crystallized slurry composition, a slurry composition, and a crude carboxylic acid composition; a wash feed; and optionally an enrichment feed to a catalyst removal zone to form a post catalyst removal composition, a catalyst rich liquor and optionally a depleted enrichment feed; wherein said wash feed is at a temperature ranging from about 5° C. to about 195° C.; wherein said post catalyst removal composition has a catalyst composition of less than 500 ppm; wherein said catalyst removal zone has a wash ratio between about 0.2 and about 6;

(b) subjecting said catalyst rich liquor to a cooling and/or concentration zone to form a concentrated mother liquor stream;

(c) subjecting at least a portion of said concentrated mother liquor stream and an extraction solvent to an extraction zone to form a catalyst depleted stream;

(d) subjecting the balance of said concentrated mother liquor stream not sent to said extraction zone and a wash stream to a SLS zone; and (e) subjecting at least a portion of said wet cake stream and optionally said catalyst depleted stream to a mix zone to form said enrichment feed.

In another embodiment of this invention, a process to produce an enrichment feed is provided. The process comprises:

(a) subjecting at least one stream selected from the group consisting of a cooled carboxylic acid composition, a crystallized slurry composition, a slurry composition, and a crude carboxylic acid composition; a wash feed; and optionally an enrichment feed to a catalyst removal zone to form a post catalyst removal composition, a catalyst rich liquor and optionally a depleted enrichment feed; wherein the wash feed is at a temperature ranging from about 10° C. to about 90° C.; wherein the post catalyst removal composition has a catalyst composition of less than 500 ppm; wherein the catalyst removal zone has a wash ratio between about 0.2 and about 6;

(b) subjecting a catalyst rich liquor to a cooling and/or concentration zone to form a concentrated mother liquor stream;

(c) subjecting at least a portion of the concentrated mother liquor stream and an extraction solvent to an extraction zone to form a catalyst depleted stream;

(d) subjecting the balance of the concentrated mother liquor stream not sent to the extraction zone and a wash stream to a SLS zone;

(e) subjecting at least a portion of the wet cake stream and optionally the catalyst depleted stream to a mix zone to form the enrichment feed.

These embodiments, and other embodiments, will become more apparent to others with ordinary skill in the art after reading this disclosure.

DETAILED DESCRIPTION OF THE INVENTION

Figure 1A:
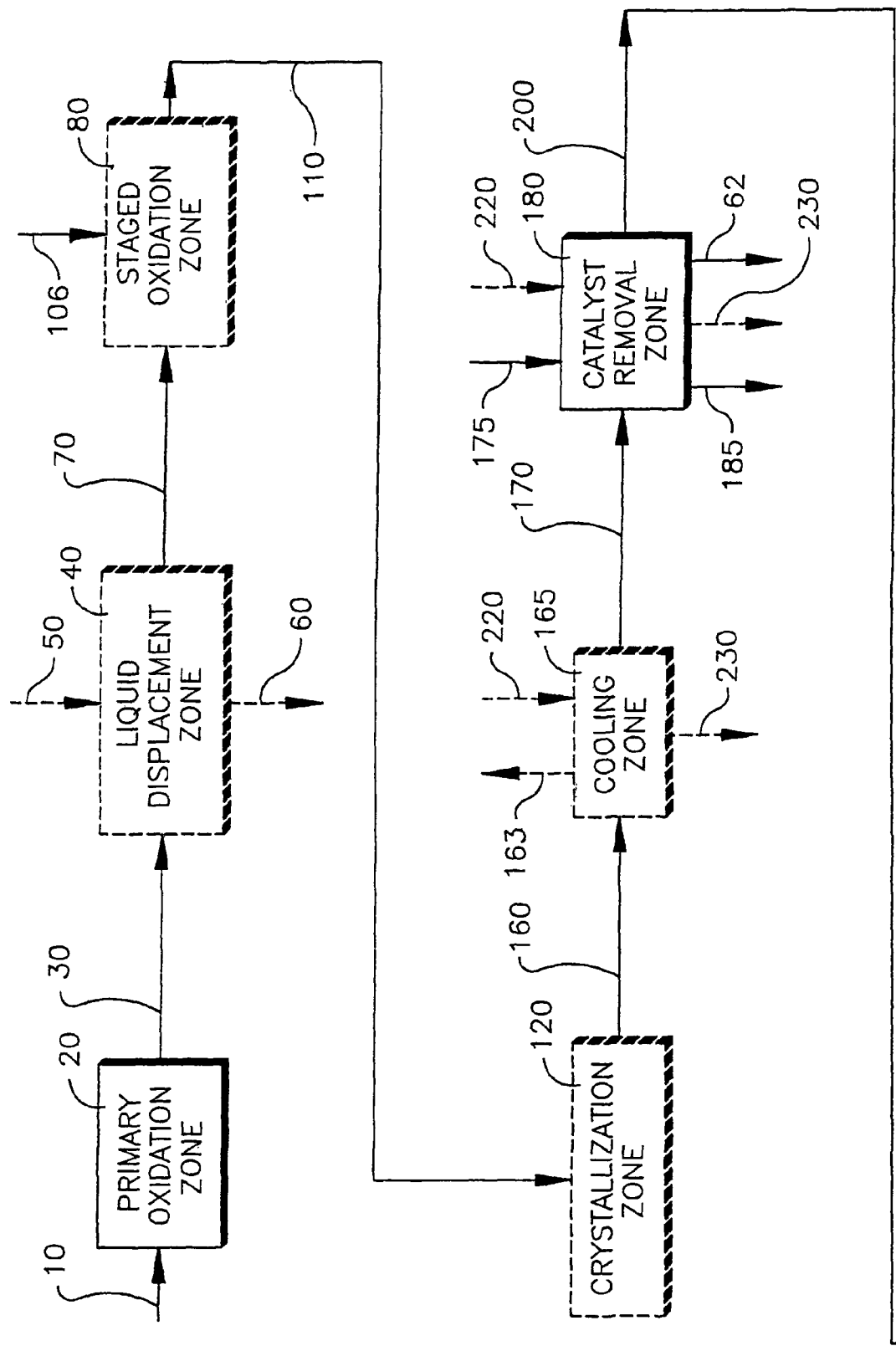
FIGS. 1A & B illustrate an embodiment of the invention where a dried carboxylic acid composition 280 is produced.

The present invention may be understood more readily by reference to the following detailed description of preferred embodiments of the invention and the Examples included herein and to the Figures and their previous and following description.

Before the present compounds, compositions, articles, devices, and/or methods are disclosed and described, it is to be understood that this invention is not limited to specific synthetic methods, specific processes, or to particular apparatuses, as such may, of course, vary. It is also to be understood that the terminology used herein is for the purpose of describing particular embodiments only and is not intended to be limiting.

In this specification and in the claims, which follow, reference will be made to a number of terms which shall be defined to have the following meanings:

As used in the specification and the appended claims, the singular forms "a," "an" and "the" include plural referents unless the context clearly dictates otherwise. Thus, for example, reference to a catalyst removal zone includes one or more catalyst removal zones.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where the event or circumstance occurs and instances where it does not. For example, the phrase "optionally heated" means that the material may or may not be heated and that such phrase includes both heated and unheated processes. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

In an embodiment of the invention, a post catalyst removal composition 200 is optionally contacted with an enrichment feed 220 in an enrichment zone 210. A slurry composition 70 or crystallized slurry composition 160 or cooled carboxylic acid composition 170 or crude carboxylic acid composition 30 can be made in any conventional process known in the art for producing a carboxylic acid composition. The slurry composition 70 or crystallized slurry composition 160 or cooled carboxylic acid composition 170 or crude carboxylic acid composition 30 is then subsequently used to produce a dried carboxylic acid composition 280 or an enriched composition 240 or a dewatered cake composition 260. For example, one method of making a post catalyst removal composition 200 is provided in FIGS. 1A & B.

Step (a) in FIG. 1A comprises oxidizing an aromatic feedstock 10 in a primary oxidation zone 20 to form a crude carboxylic acid composition 30. The aromatic feedstock 10 comprises at least one oxidizable compound, at least one solvent, and at least one catalyst.

One embodiment of the present invention concerns the liquid-phase partial oxidation of an oxidizable compound. Such oxidation is preferably carried out in the liquid phase of a multi-phase reaction medium contained in an agitated reactor or reactors. Suitable agitated reactors include, for example, bubble-agitated reactors (e.g., bubble column reactors) and mechanically agitated reactors (e.g., continuous stirred tank reactors). The liquid-phase oxidation is preferably carried out in a bubble column reactor.

As used herein, the term "bubble column reactor" shall denote a reactor for facilitating chemical reactions in a multi-phase reaction medium, wherein agitation of the reaction medium is provided primarily by the upward movement of gas bubbles through the reaction medium. As used herein, the term "agitation" shall denote work dissipated into the reaction medium causing fluid flow and/or mixing. As used herein, the terms "majority", "primarily", and "predominantly" shall mean more than 50 percent.

The oxidizable compound present in the aromatic feed stock 10 preferably comprises at least one hydrocarbyl group. More preferably, the oxidizable compound is an aromatic compound. Still more preferably, the oxidizable compound is an aromatic compound with at least one attached hydrocarbyl group or at least one attached substituted hydrocarbyl group or at least one attached heteroatom or at least one attached carboxylic acid function (—COOH). Even more preferably, the oxidizable compound is an aromatic compound with at least one attached hydrocarbyl group or at least one attached substituted hydrocarbyl group with each attached group comprising from 1 to 5 carbon atoms. Yet still more preferably, the oxidizable compound is an aromatic compound having exactly two attached groups with each attached group comprising exactly one carbon atom and consisting of methyl groups and/or substituted methyl groups and/or at most one carboxylic acid group. Even still more preferably, the oxidizable compound is para-xylene, meta-xylene, para-tolualdehyde, meta-tolualdehyde, para-toluic acid, meta-toluic acid, and/or acetaldehyde. Most preferably, the oxidizable compound is para-xylene.

A "hydrocarbyl group", as defined herein, is at least one carbon atom that is bonded only to hydrogen atoms or to other carbon atoms. A "substituted hydrocarbyl group", as defined herein, is at least one carbon atom bonded to at least one heteroatom and to at least one hydrogen atom. "Heteroatoms", as defined herein, are all atoms other than carbon and hydrogen atoms. "Aromatic compounds", as defined herein, comprise an aromatic ring, preferably having at least 6 carbon atoms, even more preferably having only carbon atoms as part of the ring. Suitable examples of such aromatic rings include, but are not limited to, benzene, biphenyl, terphenyl, naphthalene, and other carbon-based fused aromatic rings.

Suitable examples of the oxidizable compound include aliphatic hydrocarbons (e.g., alkanes, branched alkanes, cyclic alkanes, aliphatic alkenes, branched alkenes, and cyclic alkenes); aliphatic aldehydes (e.g., acetaldehyde, propionaldehyde, isobutyraldehyde, and n-butyraldehyde); aliphatic alcohols (e.g., ethanol, isopropanol, n-propanol, n-butanol, and isobutanol); aliphatic ketones (e.g., dimethyl ketone, ethyl methyl ketone, diethyl ketone, and isopropyl methyl ketone); aliphatic esters (e.g., methyl formate, methyl acetate, ethyl acetate); aliphatic peroxides, peracids, and hydroperoxides (e.g., t-butyl hydroperoxide, peracetic acid, and di-t-butyl hydroperoxide); aliphatic compounds with groups that are combinations of the above aliphatic species plus other heteroatoms (e.g., aliphatic compounds comprising one or more molecular segments of hydrocarbons, aldehydes, alcohols, ketones, esters, peroxides, peracids, and/or hydroperoxides in combination with sodium, bromine, cobalt, manganese, and zirconium); various benzene rings, naphthalene rings, biphenyls, terphenyls, and other aromatic groups with one or more attached hydrocarbyl groups (e.g., toluene, ethylbenzene, isopropylbenzene, n-propylbenzene, neopentylbenzene, para-xylene, meta-xylene, ortho-xylene, all isomers of trimethylbenzenes, all isomers of tetramethylbenzenes, pentamethylbenzene, hexamethylbenzene, all isomers of ethylmethylbenzenes, all isomers of diethylbenzenes, all isomers of ethyldimethylbenzenes, all isomers of dimethylnaphthalenes, all isomers of ethyl-methylnaphthalenes, all isomers of diethylnaphthalenes, all isomers of dimethylbiphenyls, all isomers of ethyl-methylbiphenyls, and all isomers of diethylbiphenyls, stilbene and with one or more attached hydrocarbyl groups, fluorene and with one or more attached hydrocarbyl groups, anthracene and with one or more attached hydrocarbyl groups, and diphenylethane and with one or more attached hydrocarbyl groups); various benzene rings, naphthalene rings, biphenyls, terphenyls, and other aromatic groups with one or more attached hydrocarbyl groups and/or one or more attached heteroatoms, which may connect to other atoms or groups of atoms (e.g., phenol, all isomers of methylphenols, all isomers of dimethylphenols, all isomers of naphthols, benzyl methyl ether, all isomers of bromophenols, bromobenzene, all isomers of bromotoluenes including alpha-bromotoluene, dibromobenzene, cobalt naphthenate, and all isomers of bromobiphenyls); various benzene rings, naphthalene rings, biphenyls, terphenyls, and other aromatic groups with one or more attached hydrocarbyl groups and/or one or more attached heteroatoms and/or one or more attached substituted hydrocarbyl groups (e.g., benzaldehyde, all isomers of bromobenzaldehydes, all isomers of brominated tolualdehydes including all isomers of alpha-bromotolualdehydes, all isomers of hydroxybenzaldehydes, all isomers of bromo-hydroxybenzaldehydes, all isomers of benzene dicarboxaldehydes, all isomers of benzene tricarboxaldehydes, para-tolualdehyde, meta-tolualdehyde, ortho-tolualdehyde, all isomers of toluene dicarboxaldehydes, all isomers of toluene tricarboxaldehydes, all isomers of toluene tetracarboxaldehydes, all isomers of dimethylbenzene dicarboxaldehydes, all isomers of dimethylbenzene tricarboxaldehydes, all isomers of dimethylbenzene tetracarboxaldehydes, all isomers of trimethylbenzene tricarboxaldehydes, all isomers of ethyltolualdehydes, all isomers of trimethylbenzene dicarboxaldehydes, tetramethylbenzene dicarboxaldehyde, hydroxymethyl-benzene, all isomers of hydroxymethyl-toluenes, all isomers of hydroxymethyl-bromotoluenes, all isomers of hydroxymethyl-tolualdehydes, all isomers of hydroxymethyl-bromotolualdehydes, benzyl hydroperoxide, benzoyl hydroperoxide, all isomers of tolyl methyl-hydroperoxides, and all isomers of methylphenol methyl-hydroperoxides); various benzene rings, naphthalenes rings, biphenyls, terphenyls, and other aromatic groups with one or more attached selected groups, selected groups meaning hydrocarbyl groups and/or attached heteroatoms and/or substituted hydrocarbyl groups and/or carboxylic acid groups and/or peroxy acid groups (e.g., benzoic acid, para-toluic acid, meta-toluic acid, ortho-toluic acid, all isomers of ethylbenzoic acids, all isomers of propylbenzoic acids, all isomers of butylbenzoic acids, all isomers of pentylbenzoic acids, all isomers of dimethylbenzoic acids, all isomers of ethylmethylbenzoic acids, all isomers of trimethylbenzoic acids, all isomers of tetramethylbenzoic acids, pentamethylbenzoic acid, all isomers of diethylbenzoic acids, all isomers of benzene dicarboxylic acids, all isomers of benzene tricarboxylic acids, all isomers of methylbenzene dicarboxylic acids, all isomers of dimethylbenzene dicarboxylic acids, all isomers of methylbenzene tricarboxylic acids, all isomers of bromobenzoic acids, all isomers of dibromobenzoic acids, all isomers of bromotoluic acids including alpha-bromotoluic acids, tolyl acetic acid, all isomers of hydroxybenzoic acid isomers, all isomers of hydroxymethyl-benzoic acids, all isomers of hydroxytoluic acids, all isomers of hydroxymethyl-toluic acids, all isomers of hydroxymethylbenzene dicarboxylic acids, all isomers of hydroxybromobenzoic acids, all isomers of hydroxybromotoluic acids, all isomers of hydroxymethyl-bromobenzoic acids, all isomers of carboxy benzaldehydes, all isomers of dicarboxy benzaldehydes, perbenzoic acid, all isomers of hydroperoxymethyl-benzoic acids, all isomers of hydroperoxymethylhydroxybenzoic acid isomers, all isomers of hydroperoxycarbonylbenzoic acids, all isomers of hydroperoxycarbonyl-toluenes, all isomers of methylbiphenyl carboxylic acids, all isomers of dimethylbiphenyl carboxylic acids, all isomers of methylbiphenyl dicarboxylic acids, all isomers of biphenyl tricarboxylic acids, all isomers of stilbene with one or more attached selected groups, all isomers of fluorenone with one or more attached selected groups, all isomers of naphthalene with one or more attached selected groups, benzil, all isomers of benzil with one or more attached selected groups, benzophenone, all isomers of benzophenone with one or more attached selected groups, anthraquinone, all isomers of anthraquinone with one or more attached selected groups, all isomers of diphenylethane with one or more attached selected groups, benzocoumarin, and all isomers of benzocoumarin with one or more attached selected groups).

It should be understood that the oxidizable compound present in the liquid-phase feed may comprise a combination of two or more different oxidizable chemicals. These two or more different chemical materials can be fed co-mingled in the aromatic feedstock 10 or may be fed separately in multiple feed streams. For example, an aromatic feed stock comprising para-xylene, meta-xylene, para-tolualdehyde, para-toluic acid, and acetaldehyde may be fed to the reactor via a single inlet or multiple separate inlets.

The solvent present in the aromatic feed stock 10 preferably comprises an acid component and a water component. In an embodiment of the invention, the solvent is preferably present in the aromatic feedstock 10 at a concentration in the range of from about 60 to about 98 weight percent, more preferably in the range of from about 80 to about 96 weight percent, and most preferably in the range of from 85 to 94 weight percent. The acid component of the solvent is preferably an organic low molecular weight monocarboxylic acid having 1-6 carbon atoms, more preferably 2 carbon atoms. Most preferably, the acid component of the solvent is acetic acid. Preferably, the acid component makes up at least about 75 weight percent of the solvent, more preferably at least about 80 weight percent of the solvent, and most preferably 85 to 98 weight percent of the solvent, with the balance being water.

Suitable solvents include, but are not limited to, aliphatic mono-carboxylic acids, preferably containing 2 to 6 carbon atoms, or benzoic acid and mixtures thereof and mixtures of these compounds with water.

The catalyst system present in the aromatic feed stock 10 is preferably a homogeneous, liquid-phase catalyst system capable of promoting oxidation (including partial oxidation) of the oxidizable compound. More preferably, the catalyst system comprises at least one multi-valent transition metal. Still more preferably, the multi-valent transition metal comprises cobalt. Even more preferably, the catalyst system comprises cobalt and bromine. Most preferably, the catalyst system comprises cobalt, bromine, and manganese.

When cobalt is present in the catalyst system, it is preferred for the amount of cobalt present in the aromatic feedstock 10 to be such that the concentration of cobalt in the liquid phase of the reaction medium in the primary oxidation zone 20 is maintained in the range of from about 300 to about 6,000 parts per million by weight (ppmw), more preferably in the range of from about 700 to about 4,200 ppmw, and most preferably in the range of from 1,200 to 3,000 ppmw. When bromine is present in the catalyst system, it is preferred for the amount of bromine present in the aromatic feedstock to be such that the concentration of bromine in the liquid phase of the reaction medium is maintained in the range of from about 300 to about 5,000 ppmw, more preferably in the range of from about 600 to about 4,000 ppmw, and most preferably in the range of from 900 to 3,000 ppmw. When manganese is present in the catalyst system, it is preferred for the amount of manganese present in the aromatic feedstock 10 to be such that the concentration of manganese in the liquid phase of the reaction medium is maintained in the range of from about 20 to about 1,000 ppmw, more preferably in the range of from about 40 to about 500 ppmw, most preferably in the range of from 50 to 200 ppmw.

The concentrations of the cobalt, bromine, and/or manganese in the liquid phase of the reaction medium, provided above, are expressed on a time-averaged and volume-averaged basis. As used herein, the term "time-averaged" shall denote an average of at least 10 measurements taken over a continuous 100 second period of time. As used herein, the term "volume-averaged" shall denote an average of at least 10 measurements taken at uniform 3-dimensional spacings throughout a certain volume.

The weight ratio of cobalt to bromine (Co:Br) in the catalyst system introduced into the primary oxidation zone 20 is preferably in the range of from about 0.25:1 to about 4:1, more preferably in the range of from about 0.5:1 to about 3:1, and most preferably in the range of from 0.75:1 to 2:1. The weight ratio of cobalt to manganese (Co:Mn) in the catalyst system introduced into the primary oxidation zone 20 is preferably in the range of from about 0.3:1 to about 40:1, more preferably in the range of from about 5:1 to about 30:1, and most preferably in the range of from 10:1 to 25:1.

The aromatic feedstock 10 introduced into the primary oxidation zone 20 can include small quantities of compounds such as, for example, meta-xylene, ortho-xylene, toluene, ethylbenzene, 4-carboxybenzaldehyde (4-CBA), benzoic acid, para-toluic acid, para-toluic aldehyde, alpha bromo para-toluic acid, isophthalic acid, phthalic acid, trimellitic acid, polyaromatics, and/or suspended particulates.

Step (b) optionally comprises removing at least a portion of oxidation byproducts from a crude carboxylic acid composition 30 in a liquid displacement zone 40 to form a slurry composition 70.

A crude carboxylic acid composition 30 comprises at least one carboxylic acid, at least one catalyst, at least one solvent, and at least one oxidation byproduct at least a portion of which are withdrawn via line 60. Oxidation byproducts typically comprise at least one or more of the following classes of compounds and their isomers: carboxylic acids, aldehydes, hydroxyaldehydes, carboxyaldehydes, ketones, alcohols, and hydrocarbons. In the case of oxidation of p-xylene, oxidation by-products typically comprise at least one of the following compounds: 4-carboxybenzaldehyde, p-toluic acid, p-tolualdehyde, isophthalic acid, phthalic acid, benzoic acid, trimellitic acid, 4,4'-dicarboxybiphenyl, 2,6- and 2,7-dicarboxyfluorenone, 2,6-dicarboxyanthraquinone, 4,4'-dicarboxybenzophenone, 4,4'-dicarboxybiphenyl, and a-bromo-p-toluic acid. The solvent typically comprises acetic acid, but can be any solvent that has been previously mentioned.

The crude carboxylic acid composition 30 is produced by oxidizing in a primary oxidation zone 20 an aromatic feed stock 10. In one embodiment, the aromatic feedstock 10 comprises paraxylene. The primary oxidation zone 20 comprises at least one oxidation reactor. The crude carboxylic acid composition 30 comprises at least one carboxylic acid.

In an embodiment of the invention, the oxidation reactor can be operated at temperatures between about 110° C. to about 200° C.; another range is between about 140° C. to about 170° C. Typically, the oxidizable compound in the aromatic feedstock 10 is paraxylene, and the carboxylic acid produced is terephthalic acid. In one embodiment of the invention, the primary oxidation zone 20 comprises a bubble column.

Carboxylic acids include aromatic carboxylic acids produced via controlled oxidation of an organic substrate or any carboxylic acid produced by the oxidation of oxidizable compounds previously mentioned. Such aromatic carboxylic acids include compounds with at least one carboxylic acid group attached to a carbon atom that is part of an aromatic ring, preferably having at least 6 carbon atoms, even more preferably having only carbon atoms. Suitable examples of such aromatic rings include, but are not limited to, benzene, biphenyl, terphenyl, naphthalene, and other carbon-based fused aromatic rings. Examples of suitable carboxylic acids include, but are not limited to, terephthalic acid, benzoic acid, p-toluic, phthalic acid, isophthalic acid, trimellitic acid, naphthalene dicarboxylic acid, and 2,5-diphenylterephthalic acid.

Crude terephthalic acid slurry is conventionally produced via the liquid phase oxidation of paraxylene in the presence of suitable oxidation catalyst. In another embodiment of the invention, suitable catalysts include, but are not limited to, cobalt, manganese and bromine compounds, which are soluble in the selected solvent.

The crude carboxylic acid composition in conduit 30 is optionally fed to a liquid displacement zone 40 capable of removing a portion of the liquid contained in the crude carboxylic acid composition 30 to produce the slurry composition in conduit 70. In embodiments of the invention, a portion means at least 5% by weight of the liquid is removed. In another embodiment of the invention, a portion means at least 10% by weight of the liquid is removed. In another embodiment of the invention, a portion means at least 15% by weight of the liquid is removed. In another embodiment of the invention, a portion means at least 25% by weight of the liquid is removed. In another embodiment of the invention, a portion means at least 35% by weight of the liquid is removed. In another embodiment of the invention, a portion means at least 45% by weight of the liquid is removed. In another embodiment of the invention, a portion means at least 55% by weight of the liquid is removed. In another embodiment of the invention, a portion means at least 65% by weight of the liquid is removed. In another embodiment of the invention, a portion means at least 75% by weight of the liquid is removed. In another embodiment of the invention, a portion means at least 85% by weight of the liquid is removed. In another embodiment of the invention, a portion can mean any part up to and including the whole by weight of the liquid is removed.

The removal of a portion of the liquid to produce a slurry composition in conduit 70 can be accomplished by any means known in the art. Typically, the liquid displacement zone 40 comprises a solid-liquid separator that is selected from the group consisting of a decanter centrifuge, disk stack centrifuge, vacuum belt filter, rotary vacuum filter, rotary pressure filter, perforated basket centrifuge and the like. The crude carboxylic acid composition in conduit 30 is fed to the liquid displacement zone 40 comprising at least one solid-liquid separator. In an embodiment of the invention, the solid-liquid separator can be operated at temperatures between about 5° C. to about 200° C. In yet another range, the solid-liquid separator can be operated from about 90° C. to about 170° C. In yet another range, the solid-liquid separator can be operated from about 140° C. to about 170° C. The solid-liquid separator can be operated at pressures up to 200 psig. In yet another range the solid liquid separator can be operated at pressures between about 30 psig to about 200 psig. The solid-liquid separator in the liquid displacement zone 40 may be operated in continuous or batch mode, although it will be appreciated that for commercial processes, the continuous mode is preferred.

A portion of the oxidation byproducts is displaced from the liquid displacement zone 40 in a mother liquor and withdrawn via line 60. In one embodiment of the invention, additional solvent is fed to the liquid displacement zone 40 via line 50 to reslurry the crude carboxylic acid composition 30 and form a slurry composition 70. The mother liquor 60 is withdrawn from liquid displacement zone 40 via line 60 and comprises a solvent, typically acetic acid, catalyst, and at least one oxidation byproduct(s). The mother liquor in line 60 may either be sent to a process for separating impurities from oxidation solvent via lines not shown or recycled to the catalyst system via lines not shown. One technique for impurity removal from the mother liquor 60 commonly used in the chemical processing industry is to draw out or "purge" some portion of the recycle stream. Typically, the purge stream is simply disposed of, or if economically justified, subjected to various treatments to remove undesired impurities while recovering valuable components. Examples of impurity removal processes include U.S. Pat. No. 4,939,297 and U.S. Pat. No. 4,356,319, herein incorporated by reference to the extent that they do not contradict statements made herein.

In embodiments of the present invention a process is described that can allow for the controlled partitioning of at least one selected compound, by-product or impurity among the filtration mother liquor, wash feed, and terephthalic acid wet cake while achieving recovery of the oxidization catalyst and oxidation reaction solvent or medium.

Also in embodiments of this invention, the purge process can be significantly reduced or eliminated by the enrichment of a post catalyst removal composition 200 with selected compounds. The enrichment process results in these compounds being carried out with the enriched composition 240 or the dried carboxylic acid composition 280, therefore greatly reducing or eliminating a purge process. The enrichment can be preceded by a catalyst removal process.

Figure 2:
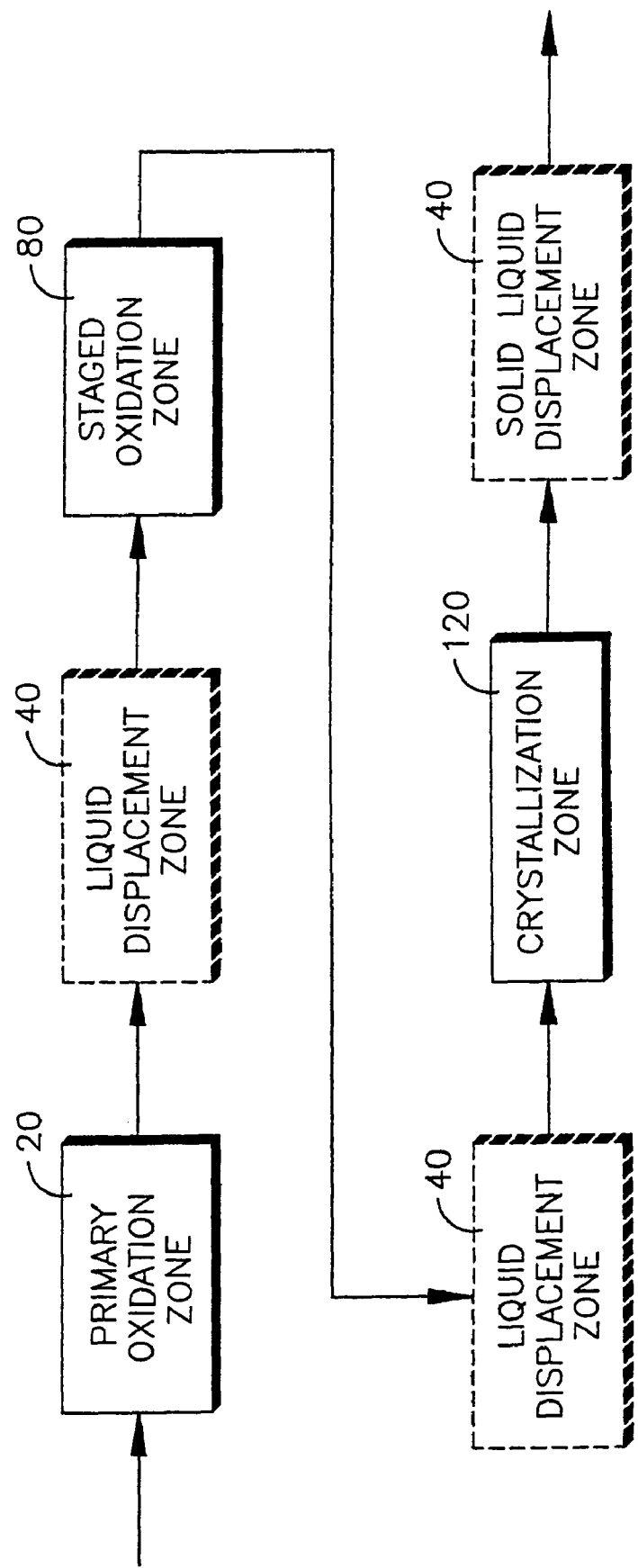
FIG. 2 illustrates various embodiments of the invention wherein multiple liquid displacement zones 40 can be used.

It should be pointed out that the liquid displacement zone 40 is optional and also can be located in multiple locations in the process as shown in FIG. 2 by the dashed lines. In another embodiment of the invention, there are more than one liquid displacement zone(s) 40 such as, for example, between the primary oxidation zone 20 and staged oxidation zone 80, and another liquid displacement zone 40 can be located either after the staged oxidation zone 80 or after the crystallization zone 120. There could be three liquid displacement zones 40 as shown in FIG. 2 or any combination as shown in FIG. 2.

Step (c) comprises optionally oxidizing the slurry composition 70 or a crude carboxylic acid composition 30 in a staged oxidation zone 80 to form a staged oxidation composition 110.

In one embodiment of the invention, the slurry composition 70 or a crude carboxylic acid composition 30 is withdrawn via line 70 to a staged oxidation zone 80 and can be heated to between about 140° C. to about 280° C. Another range is between about 160° C. to about 240° C., another range is between about 170° C. to about 200° C., and further oxidized with air fed by line 106 to produce a staged oxidation composition 110. Another range is about 180° C. to about 280° C.

The staged oxidation zone 80 comprises at least one staged oxidation reactor vessel. The slurry composition 70 is fed to the staged oxidation zone 80. The term "staged" means that the oxidation occurs in both the primary oxidation zone 20 discussed previously as well as in the staged oxidation zone 80. For example, the staged oxidation zone 80 can comprise staged oxidation reactor vessels in series.

When the carboxylic acid is terephthalic acid, the staged oxidation zone 80 comprises an oxidation reactor that can be heated to between about 140° C. to about 280° C. or between about 160° C. to about 240, or between about 170° C. to about 200° C., or between about 160° C. to about 210° C., and further oxidized with air or a source of molecular oxygen fed by line 106 to produce a staged oxidation composition 110. In an embodiment of the invention, oxidation in the staged oxidation zone 80 is at a higher temperature than the oxidation in the primary oxidation zone 20 to enhance the impurity removal. The staged oxidation zone 80, as well as streams 30 and 70, can be heated directly with solvent vapor, or steam, or indirectly by any means known in the art. Purification in the staged oxidation zone 80 takes place by a mechanism involving recrystallization or crystal growth and oxidation of impurities.

Additional air or molecular oxygen may be fed via conduit 106 to the staged oxidation zone 80 in an amount necessary to oxidize at least a portion of the partially oxidized products, such as, 4-carboxybenzaldehyde (4-CBA) and p-toluic acid in the crude carboxylic acid composition 30 or slurry composition 70 to the corresponding carboxylic acid. Generally, at least 70% by weight of the 4-CBA is converted to terephthalic acid in the staged oxidation zone 80. Preferably, at least 80% by weight of the 4-CBA is converted to terephthalic acid in the staged oxidation zone 80. Significant concentrations of 4-carboxybenzaldehyde and p-toluic acid in the terephthalic acid product are particularly detrimental to polymerization processes as they may act as chain terminators during the condensation reaction between terephthalic acid and ethylene glycol in the production of polyethylene terephthalate (PET).

Impurities in the crude carboxylic acid composition 30 or slurry composition 70 go into solution as the terephthalic acid particles are dissolved and re-crystallized in the staged oxidation zone 80. Offgas from the staged oxidation zone 80 is withdrawn and can be fed to a recovery system where the solvent is removed from the offgas comprising volatile organic compounds (VOCs). VOCs including methyl bromide may be treated, for example, by incineration in a catalytic oxidation unit. The offgas may also be processed before the staged oxidation composition 110 from the staged oxidation zone 80 is withdrawn via line 110.

Step (d) comprises optionally crystallizing the slurry composition 70 or the crude carboxylic acid composition 30 or the staged oxidation composition 110 in a crystallization zone 120 to form a crystallized slurry composition 160. Generally, the crystallization zone 120 comprises at least one crystallizer. Vapor product from the crystallization zone 120 can be condensed in at least one condenser and returned to the crystallization zone 120. Optionally, the liquid from the condenser or vapor product from the crystallization zone 120 can be recycled, or it can be withdrawn or sent to an energy recovery device.

In addition, the crystallizer offgas is removed and can be routed to a recovery system where the solvent is removed and crystallizer offgas comprising VOCs may be treated, for example, by incineration in a catalytic oxidation unit.

The staged oxidation composition 110 from the staged oxidation zone 80 is withdrawn via line 110 and fed to a crystallization zone 120 comprising at least one crystallizer where it is cooled to a temperature between about 110° C. to about 190° C. to form a crystallized slurry composition 160, preferably to a temperature between about 140° C. to about 180° C., and most preferably about 150° C. to about 170° C.

The crystallized slurry composition 160 from the crystallization zone 120 is withdrawn via line 160. Typically, the crystallized slurry composition 160 is then fed directly to a vessel and cooled to form a cooled carboxylic acid composition 170. When the carboxylic acid is terephthalic acid, the cooled carboxylic acid composition 170 is cooled in a vessel to typically a temperature of about 160° C. or less, preferably to about 100° C. or less, before being introduced into a process for recovering the terephthalic acid as a dry powder or wet cake.

Step (e) comprises optionally cooling the crystallized slurry composition 160 or the staged oxidation composition 110 or the slurry composition 70 or the crude carboxylic acid composition 30 in a cooling zone 165 to form a cooled carboxylic acid composition 170.

The crystallized slurry composition 160 or the staged oxidation composition 110 or the slurry composition 70 or the crude carboxylic acid composition 30 is fed to a cooling zone 165 and cooled to a temperature ranging from about 5° C. to about 160° C., or about 5° C. to about 90° C., or about 5° C. to about 195° C. or about 20° C. to about 160° C. to form the cooled carboxylic acid composition 170. In another embodiment of the invention, the crystallized slurry composition 160 or the staged oxidation composition 110 or the slurry composition 70 or the crude carboxylic acid composition 30 is fed to a cooling zone 165 and cooled to a temperature ranging from about 20° C. to about 90° C. to form the cooled carboxylic acid composition 170. In another embodiment of the invention, the crystallized slurry composition 160 or the staged oxidation composition 110 or the slurry composition 70 or the crude carboxylic acid composition 30 is fed to a cooling zone 165 and cooled to a temperature ranging from about 20° C. to about 120° C. to form the cooled carboxylic acid composition 170. In another embodiment of the invention, the crystallized slurry composition 160 or the staged oxidation composition 110 or the slurry composition 70 or the crude carboxylic acid composition 30 is fed to a cooling zone 165 and cooled to a temperature ranging from about 10° C. to about 90° C. to form the cooled carboxylic acid composition 170. In another embodiment of the invention, the crystallized slurry composition 160 or the staged oxidation composition 110 or the slurry composition 70 or the crude carboxylic acid composition 30 is fed to a cooling zone 165 and cooled to a temperature ranging from about 20° C. to about 60° C. to form the cooled carboxylic acid composition 170. In another embodiment of the invention, the crystallized slurry composition 160 or the staged oxidation composition 110 or the slurry composition 70 or the crude carboxylic acid composition 30 is fed to a cooling zone 165 and cooled to a temperature ranging from about 20° C. to about 40° C. to form the cooled carboxylic acid composition 170.

In another embodiment of the invention, a portion of the solvent is optionally removed from the crystallized slurry composition 160 or the staged oxidation composition 110 or the slurry composition 70 or the crude carboxylic acid composition 30 via conduit 163 to produce the cooled carboxylic acid composition 170. In one embodiment of the invention, a portion can mean any part up to and including the whole. A portion can mean at least 5% by weight of the solvent is removed. In another embodiment of the invention, a portion can mean at least 10% by weight of the solvent is removed. In another embodiment of the invention, a portion can mean at least 25% by weight of the solvent is removed. In another embodiment of the invention, a portion can mean at least 50% by weight of the solvent is removed. In another embodiment of the invention, a portion can mean at least 75% by weight of the solvent is removed. In another embodiment of the invention, a portion can mean at least 85% by weight of the solvent is removed. In another embodiment of the invention, a portion can mean at least 90% by weight of the solvent is removed from the crystallized slurry composition 160 or the staged oxidation composition 110 or the slurry composition 70 or the crude carboxylic acid composition 30.

Solvent removal can be accomplished by any means known in the art. For example, the solvent can be removed by evaporation or by flashing and removing the solvent under vacuum.

In another embodiment of the invention, both cooling and solvent removal are utilized.

Figure 3:
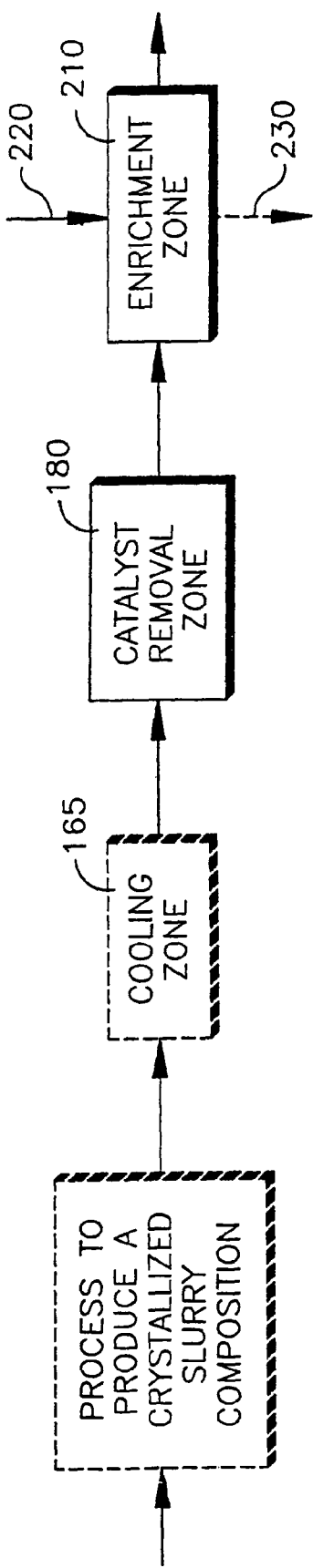
FIG. 3 illustrates an embodiment of the invention wherein a crystallized slurry composition 160 can be produced by multiple different processes.
Figure 4:
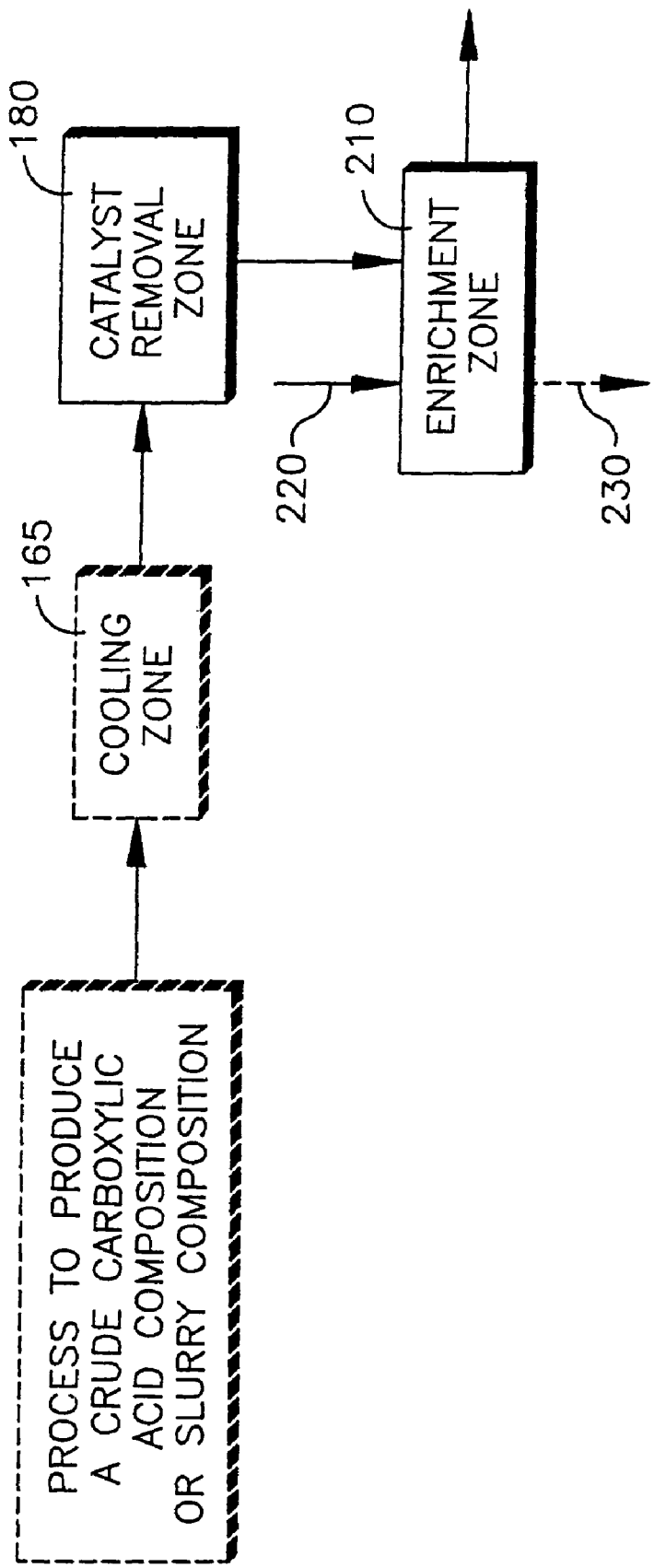
FIG. 4 illustrates an embodiment of the invention wherein the crude carboxylic acid composition or a slurry composition can be produced by multiple different processes.

Steps (a) through steps (d) and steps (a) through (e) are to illustrate embodiments of the invention in which a cooled carboxylic acid composition 170 is produced. In should also be pointed out that the liquid displacement zone 40, the staged oxidation zone 80, and the crystallization zone 120 were all optional in this embodiment of the invention. For example, other processes that produce a cooled carboxylic acid composition 170, or a crystallized slurry composition 160, or a staged oxidation composition 110, or a slurry composition 70, or a crude carboxylic acid composition 30 can be utilized. Such processes are described in U.S. Pat. Nos. 5,877,346; 4,158,738; 5,840,965; 5,877,346; U.S. Pat. No. 5,527,957; and U.S. Pat. No. 5,175,355, all of which are herein incorporated by reference in their entirety to the extent that they do not contradict statements made herein. Therefore, as shown in FIG. 3, any process known in the art capable of producing a crystallized slurry composition 160 can be utilized. In addition, as shown in FIG. 4, any process known in the art capable of producing a crude carboxylic acid composition 30 or a slurry composition 70 can be utilized.

Figure 5:
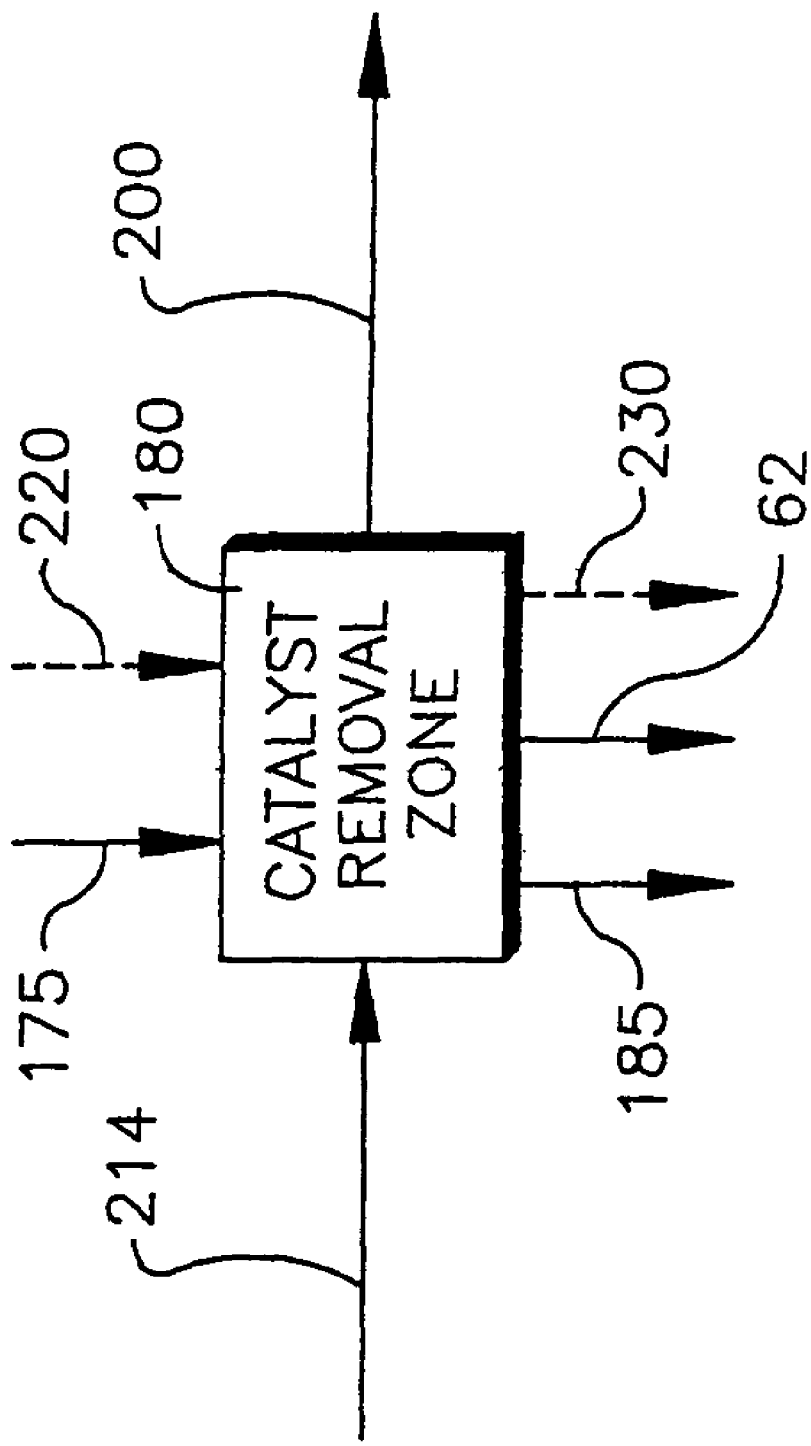
FIG. 5 illustrates an embodiment of the invention wherein a post catalyst removal composition 200 is produced from a carboxylic acid composition 214 in a catalyst removal zone 180.
Figure 6:
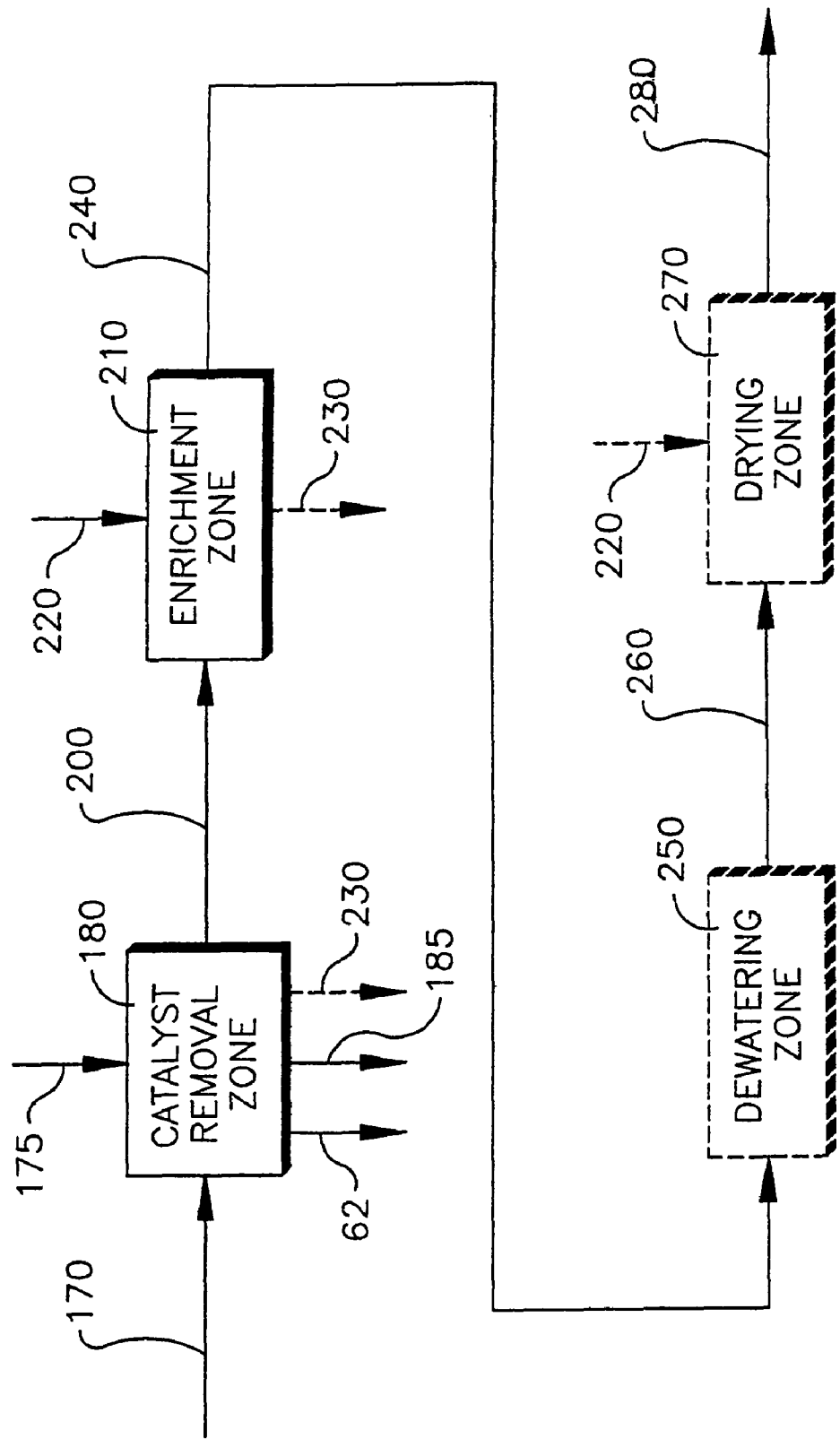
FIG. 6 illustrates an embodiment of the invention wherein both a catalyst removal zone 180 and an enrichment zone 210 are utilized to produce an enriched composition 240 from a cooled carboxylic acid composition 170.

Generally, as depicted in FIG. 5, any carboxylic acid composition 214 can be used in step (f) provided the carboxylic acid composition or cooled carboxylic acid composition 170 comprises at least one carboxylic acid, at least one solvent and at least one catalyst. The carboxylic acid comprises any carboxylic acid previously disclosed or any carboxylic acid capable of being produced by the oxidation of the oxidizable compounds previously disclosed. The solvent is typically acetic acid, but can be any solvent previously disclosed. The catalyst is any catalyst that has been previously disclosed. FIG. 6 shows a process that utilizes a cooled carboxylic acid composition 170 in step (f).

Step (f) comprises contacting a cooled carboxylic acid composition 170, or a crystallized slurry composition 160, or a staged oxidation composition 110 or a slurry composition 70, or a crude carboxylic acid composition 30 with a wash feed 175 and optionally an enrichment feed 220 in a catalyst removal zone 180 to form a catalyst rich liquor 185, a wash liquor stream 62, an optional depleted enrichment liquor stream 230, and a post catalyst removal composition 200.

The cooled carboxylic acid composition 170, or a crystallized slurry composition 160, or a staged oxidation composition 110 or a slurry composition 70, or a crude carboxylic acid composition 30 is contacted with a wash feed 175 in the catalyst removal zone 180. In an embodiment of the invention the cooled carboxylic acid composition 170 can be in the form or a dry powder, wet cake, liquid or gas entrained liquid, solid, slurry, solution or combination thereof.

The wash feed 175 is contacted with the cooled carboxylic acid composition 170, or a crystallized slurry composition 160, or a staged oxidation composition 110 or a slurry composition 70, or a crude carboxylic acid composition 30 in the catalyst removal zone 180 to remove a portion of the catalyst from the cooled, purified carboxylic acid composition 170 to form the post catalyst removal composition 200. In an embodiment of the invention, the post catalyst removal composition 200 comprises a carboxylic acid, solvent, catalyst, and optionally, one or more compounds selected from the group consisting of isophthalic acid, phthalic acid, trimellitic acid, hydroxymethylbenzoic acid isomers, hydroxybenzoic acid isomers, benzoic acid, and toluic acid isomers. In another embodiment of the invention, the post catalyst removal composition 200 comprises a carboxylic acid, solvent and optionally one or more compounds selected from the group consisting of isophthalic acid, phthalic acid, trimellitic acid, benzoic acid, 4-hydroxybenzoic acid, 4-hydroxymethyl benzoic acid, 4,4'-dicarboxybiphenyl, 2,6-dicarboxyanthraquinone, 4,4'-dicarboxystilbene, 2,5,4'-tricarboxybiphenyl, 2,5,4'-tricarboxybenzophenone, 4,4'-dicarboxybenzophenone, 4,4'-dicarboxybenzil, form-acethydroxybenzoic acid, acet-hydroxymethylbenzoic acid, a-bromo-p-toluic acid, bromo-benzoic acid, bromo-acetic acid, p-tolualdehye and terephthaldehyde. In an embodiment of the invention, the post catalyst removal composition 200 can be in the form of a dry powder, wet cake, slurry, solution, liquid, gas-entrained liquid or solid. In another embodiment of the invention the post catalyst removal composition 200 can comprise any composition suitable to produce the dried carboxylic acid composition 280 to be described subsequently.

A portion of the catalyst is removed via the catalyst rich liquor 185 and the wash liquor 62 from the cooled carboxylic acid composition 170, or a crystallized slurry composition 160, or a staged oxidation composition 110 or a slurry composition 70, or a crude carboxylic acid composition 30 to produce the post catalyst removal composition 200 having a catalyst concentration of less than 1000 ppm by weight. The catalyst rich liquor 185 comprises solvent, catalyst, and an oxidation byproduct(s). The wash liquor 62 comprises at least one solvent, at least one catalyst, an at least one oxidation byproduct(s). As used herein, catalyst can be at least one catalyst previously described in the catalyst system. In another embodiment of the invention, catalyst can be any catalyst used in an oxidation reaction of an aromatic feedstock. In another embodiment of the invention, a portion of catalyst is removed when the post catalyst removal composition 200 has a catalyst concentration of less than 500 ppm by weight. In another embodiment of the invention, a portion is that amount of catalyst that is removed such that the post catalyst removal composition 200 has a catalyst concentration of less than 250 ppm by weight. In another embodiment of the invention, a portion is that amount of catalyst that is removed such that the post catalyst removal composition 200 has a catalyst concentration of less than 75 ppm by weight. Another range is less than 50 ppm by weight. In yet other ranges, the catalyst concentration of the post catalyst removal composition 200 is less than 20 ppm by weight or less than 10 ppm by weight. In yet other ranges, the catalyst concentration is less than 5 ppm by weight or less than 1 ppm by weight. As used herein "catalyst concentration" means the total concentration of all catalyst in the composition.

The wash feed 175 comprises compositions that are capable of producing the post catalyst removal composition 200 previously disclosed. In an embodiment of the invention, the wash feed 175 can be in a form of a liquid or a condensable vapor or a solution. In another embodiment of the invention, the wash feed 175 is greater than 50% by weight water. In another embodiment of the invention, the wash feed 175 is greater than 75% by weight water. In another embodiment of the invention, the wash feed 175 is greater than 90% by weight water. In another embodiment of the invention, the wash feed 175 is greater than 50% by weight solvent. In another embodiment of the invention, the wash feed 175 is greater than 75% by weight solvent. In another embodiment of the invention, the wash feed 175 is greater than 90% by weight solvent. In another embodiment of the invention, the wash feed 175 comprises at least one solvent, and optionally at least one compound selected from the group consisting of benzoic acid, isophthalic acid, phthalic acid, trimellitic acid, hydroxybenzoic acid isomers, hydroxymethylbenzoic acid isomers, and p-toluic acid. In another embodiment of the invention the wash feed 175 comprises compositions sufficient to produce the dried carboxylic acid composition 280 disclosed subsequently. In another embodiment of the invention the wash feed 175 comprises at least one solvent, and optionally at least one compound selected from the group consisting of isophthalic acid, phthalic acid, trimellitic acid, hydroxymethylbenzoic acid isomers, hydroxybenzoic acid isomers, benzoic acid, and toluic acid isomers and wherein at least one of the compounds is enriched above the concentration of the post catalyst removal composition 200. In another embodiment of the invention, the wash feed 175 comprises at least one solvent, and optionally, one or more compounds selected from the group consisting of isophthalic acid, phthalic acid, trimellitic acid, benzoic acid, 4-hydroxybenzoic acid, 4-hydroxymethylbenzoic acid, 4,4'-dicarboxybiphenyl, 2,6-dicarboxyanthraquinone, 4,4'-dicarboxystilbene, 2,5,4'-tricarboxybiphenyl, 2,5,4'-tricarboxybenzophenone, 4,4'-dicarboxybenzophenone, 4,4'-dicarboxybenzil, form-acet-hydroxybenzoic acid, acet-hydroxymethylbenzoic acid, a-bromo-p-toluic acid, bromo-benzoic acid, bromo-acetic acid, p-tolualdehye and terephthaldehyde.

In an embodiment of the invention the wash feed has a temperature ranging from the freezing point of the solvent to about 90° C., or about 5° C. to about 90° C., or about 5° C. to about 195° C., or about 5° C. to about 100° C. or the freezing point of the solvent to about 70° C., or about 5° C. to about 70° C., or about 30° C. to about 70° C., or the freezing point of the solvent to about 30° C.

In an embodiment of the invention the wash ratio ranges from about 0.2 to about 6.0, or about 0.2 to about 4.0, or about 0.2 to about 1.0, or about 0.4 to about 1, or about 0.5 to about 2.0, or about 1 to about 3. The "wash ratio" as used herein means the total mass of the wash feed 175 divided by the mass of the post catalyst removal composition 200 on a dry solids basis.

The catalyst removal zone 180 comprises at least one solid liquid separation device capable of contacting the cooled carboxylic acid composition 170 or a crystallized slurry composition 160, or a staged oxidation composition 110 or a slurry composition 70, or a crude carboxylic acid composition 30 with the wash feed 175 to produce a post catalyst removal composition 200.

For example, the catalyst removal zone 180 comprises one solid liquid separation device in which a post catalyst removal composition 200 is generated and then washed with a wash solvent. Examples include, but are not limited to, a rotary vacuum drum filter, a vacuum belt filter, a rotary pressure filter, a filter press, and a pressure leaf filter. Solid liquid separation devices, which can generate a cake but do not allow washing, are also useful when combined with a reslurry device. Solid liquid separation devices, such as, a solid bowl centrifuge can be used to generate a cake which can be reslurried with wash solvent in a separate mixing device to achieve washing by dilution. Washing by dilution often requires multiple stages of cake generation and subsequent reslurrying operated in a counter current fashion.

Step (g) comprises optionally contacting a post catalyst removal composition 200 with a enrichment feed 220 in an enrichment zone 210 to form a depleted enrichment stream 230 and an enriched composition 240; wherein the enriched composition 240 comprises one or more compounds selected from the group consisting of isophthalic acid, phthalic acid, trimellitic acid, hydroxymethylbenzoic acid isomers, hydroxybenzoic acid isomers, benzoic acid, and toluic acid isomers and wherein at least one of the compounds is enriched above the concentration of the post catalyst removal composition 200. In another embodiment of the invention, the enriched composition 240 comprises one or more compounds selected from the group consisting of isophthalic acid, phthalic acid, trimellitic acid, benzoic acid, 4-hydroxybenzoic acid, 4-hydroxymethylbenzoic acid, 4,4'-dicarboxybiphenyl, 2,6-dicarboxyanthraquinone, 4,4'-dicarboxystilbene, 2,5,4'-tricarboxybiphenyl, 2,5,4'-tricarboxybenzophenone, 4,4'-dicarboxybenzophenone, 4,4'-dicarboxybenzil, form-acet-hydroxybenzoic acid, acet-hydroxymethylbenzoic acid, a-bromo-p-toluic acid, bromo-benzoic acid, bromo-acetic acid, p-tolualdehye and terephthaldehyde.

Figure 1B:
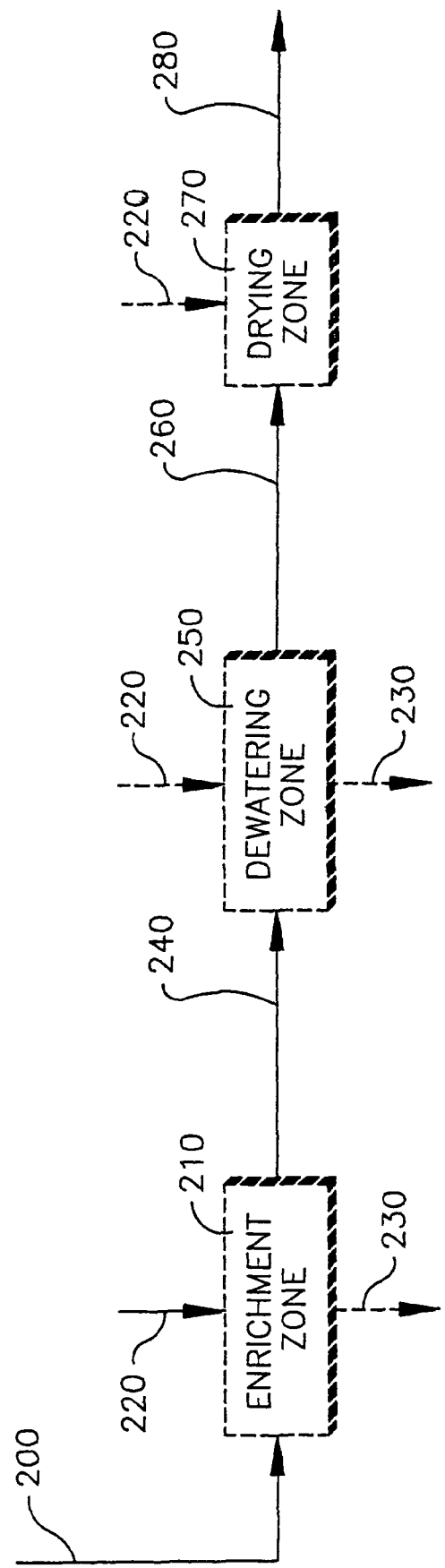

The term "enriched" means that primary outlet stream leaving an enrichment zone or plurality of enrichment zones, or any zone, or any conveyance mentioned herein has a greater concentration of any selected enrichment compound(s) than the primary inlet stream going into an enrichment zone or plurality of enrichment zones, wherein the enrichment compound(s) comprises at least one compound or compounds selected from the group consisting of terephthalic acid, isophthalic acid, phthalic acid, benzene-tricarboxylic acid isomers, benzoic acid, hydroxybenzoic acid isomers, hydroxymethylbenzoic acid isomers, dicarboxybiphenyl isomers, dicarboxystilbene isomers, tricarboxybiphenyl isomers, tricarboxybenzophenone isomers, dicarboxybenzophenone isomers, dicarboxybenzil isomers, form-acethydroxybenzoic acid isomers, acet-hydroxymethylbenzoic acid isomers, a-bromo-toluic acid isomers, bromo-benzoic acid, bromo-acetic acid, tolualdehye isomers, and phthaldehyde isomers. In another embodiment of the invention, enrichment compounds or the enrichment feed 220 can also include monomers, co-monomers, additives, or any compounds useful for making polyester or any combination thereof. For example, in an embodiment of the invention depicted on FIGS. 1a and 1b, the primary outlet stream is the enriched composition 240 and the primary inlet stream is the post catalyst removal composition 200. In an embodiment of the invention, shown in FIG. 9, the primary inlet stream is the carboxylic acid composition 214, or the crystallized slurry composition 160, and the primary outlet stream is the enriched carboxylic acid stream 280. In an embodiment of the invention, depicted in FIG. 10, the primary inlet stream is the carboxylic acid composition 214, and the primary outlet stream is the enriched carboxylic acid composition 216.

In other embodiments of the invention, the termed "enriched" means that the primary outlet stream has a greater concentration of any selected compound(s) as described previously by at least 5 ppmw, or at least 10 ppmw, or at least 100 ppmw, or at least 1000 ppmw, or at least 5 wt %, or at least 10 wt %, or at least 25 wt %, or at least 30 wt % or at least 50 wt % than the primary inlet stream, all measured on a dry solid basis.

The enrichment feed 220 comprises compounds sufficient to enrich at least one compound selected from the group consisting of terephthalic acid, isophthalic acid, phthalic acid, benzene-tricarboxylic acid isomers, benzoic acid, hydroxybenzoic acid isomers, hydroxymethylbenzoic acid isomers, dicarboxybiphenyl isomers, dicarboxystilbene isomers, tricarboxybiphenyl isomers, tricarboxybenzophenone isomers, dicarboxybenzophenone isomers, dicarboxybenzil isomers, form-acet-hydroxybenzoic acid isomers, acet-hydroxymethylbenzoic acid isomers, a-bromo-toluic acid isomers, bromo-benzoic acid, bromo-acetic acid, tolualdehye isomers, benzyl alcohol isomers, methyl benzyl alcohol isomers, and phthaldehyde isomers. In the another embodiment of the invention, the enrichment feed 220 can also include monomers, co-monomers, additives, or any compounds useful for making polyester or any combination thereof. In another embodiment of the invention the enrichment compounds or enrichment feed 220 comprises one or more compounds selected from the group consisting of fluorene isomers, diphenyl methane isomers, diphenyl ethane isomers, and saturated aromatic isomers. Examples of saturated aromatic isomers include, but are not limited to, cyclohexane carboxylic acid and 1,4-cyclohexane dicarboxylic acid.

Figure 7:
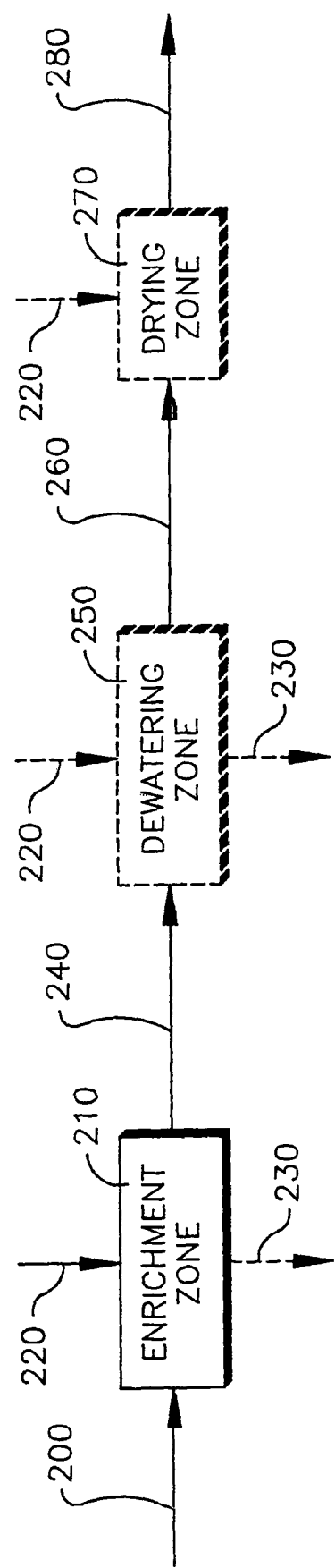
FIG. 7 illustrates an embodiment of the invention wherein an enriched composition 240 is produced from a post catalyst removal composition 200 in an enrichment zone 210.

In another embodiment of the invention, the enrichment feed 220 comprises compounds sufficient to enrich the post catalyst removal composition 200 as shown in FIG. 7 such that on a dry solids basis the enriched composition 240 comprises compositions identical to the dried carboxylic acid composition 280 described subsequently. There are no special limitations as far as the conditions of the enrichment feed 220 other than it comprises compounds sufficient to enrich the post catalyst removal composition 200 with the enrichment compound(s) specified previously. For example, the enrichment feed 220 can be, but is not limited to a cake, powder, solids, wash feed, slurry, solution, paste, or gas entrained solid or liquid.

Figure 8:
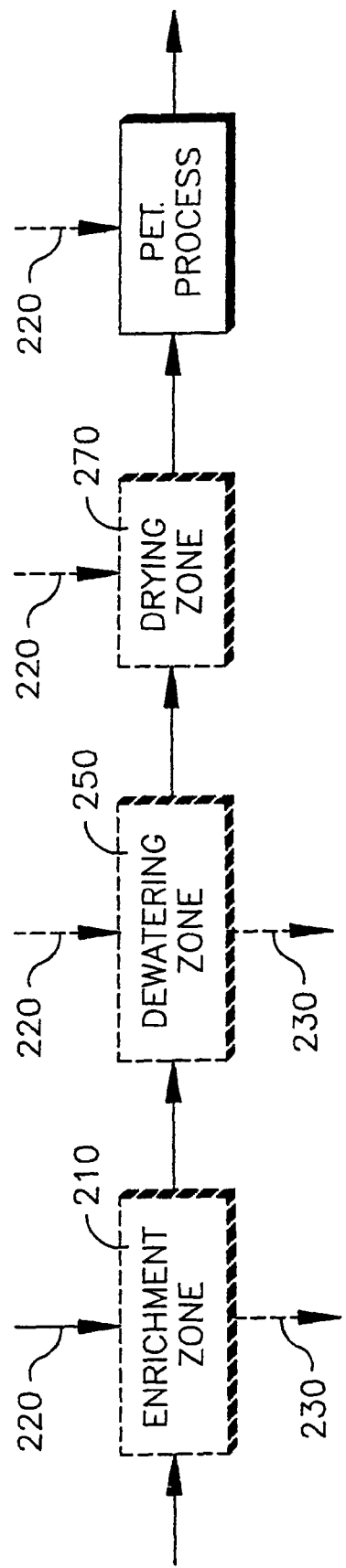
FIG. 8 illustrates an embodiment of the invention showing multiple enrichment feed 220 points.

It should be pointed out that the enrichment feed 220 does not necessarily need to be introduced into the enrichment zone 210. As shown in FIG. 8, the enrichment feed 220 can be introduced in a number of locations including, but not limited to, the enrichment zone 210, dewatering zone 250, drying zone 270, and in the polyester processes, or more specifically PET processes. A variety of polyester processes have been developed. Early efforts used reactive distillation as shown in U.S. Pat. No. 2,905,707 and reactive distillation with ethylene glycol ("EG") vapor as reactants as shown in U.S. Pat. No. 2,829,153 to produce PET: both of these patents are herein incorporated by reference to the extent they do not contradict statements made herein. Multiple stirred pots have been disclosed to gain additional control of the reaction as shown in U.S. Pat. No. 4,110,316, herein incorporated by reference to the extent it does not contradict statement made herein. U.S. Pat. No. 3,054,776 discloses the use of lower pressure drops between reactors in a PET process, while U.S. Pat. No. 3,385,881 discloses multiple reactor stages within one reactor shell, both of these patents are herein incorporated by reference to the extent they do not contradict statement made herein. These designs were improved to solve problems with entrainment or plugging, heat integration, heat transfer, reaction time, the number of reactors, etc., as described in U.S. Pat. Nos. 3,118,843; 3,582,244; 3,600,137; 3,644,096; 3,689,461; 3,819,585; 4,235,844; 4,230,818; and 4,289,895; all of which are herein incorporated by reference to the extent that they do not contradict statements made herein.

In a PET process 400 as shown in FIG. 8, the enrichment feed 220 can be introduced in the paste tank, esterification reactors, and/or other locations in the process. The enrichment feed 220 can be introduced in multiple locations or at only one location, either at one time or gradually over time.

Raw materials for manufacturing step-growth polymers and copolymers from terephthalic acid (TPA) include monomers and co-monomers, catalyst(s), and additives. Monomers and co-monomers include, but are not limited to, diamines, diols, and diacids, etc. Important commercial step-growth polymers which can be made using TPA as a monomer or co-monomer include polyamides, polyesters, especially poly (ethylene terephthalate) (PET), co-polyamides, co-polyesters, and co-polyester-amides. It can be advantageous to introduce and achieve intimate mixing of the monomers or co-monomers, catalyst(s) and/or additives with the terephthalic acid, so that they do not have to be added to the polymerization process separately from the TPA. A process has been invented that allows for the production of terephthalic acid, in the form of powder, paste, wet cake, or slurry, and which is enriched with certain monomers or co-monomers, catalyst(s) and/or additives. This process is achieved with intimate mixing with TPA so as to obviate the need for separate addition of the materials in the PET manufacturing process.

The following description will be given for PET, but can be extended in a straight-forward manner to other step-growth polymers and copolymers made using TPA. The manufacture of PET involves the esterification of terephthalic acid with ethylene glycol, formation of a prepolymer, and polycondensation to form PET with a molecular weight high enough for the intended subsequent polymer processing and application which can include coatings, fibers, films, containers, and other articles. Certain monomers or co-monomers, catalyst(s) and/or additives can also be used. The most common co-monomers, beside ethylene glycol (EG), are isophthalic acid (IPA or PIA) and cyclohexanedimethanol (CHDM). The most common catalysts for PET manufacture are antimony and titanium. Additives useful in the manufacture of PET include, but are not limited to, phosphorous compounds, dyes, pigment, colorants, reheat agents, polydispersity modifiers, anti-oxidants and stabilizers (thermal, oxidative, UV, etc.), coupling or chain-extending agents, end-capping agents, telechelic modifiers, such as, for example metal co-ordinated sulfo-isophthalic acid, acetaldehyde reducing agents, acetaldehyde scavengers, buffers, agents to reduce formation of diethylene glycol (DEG), antistats, slip or anti-block agents, barrier modifiers, nucleators, titanium dioxide and other fillers/opacifiers, anti-fogging agents, optical brighteners, etc. The introduction of such co-monomers, catalyst(s), and/or additives is typically at various points in the PET manufacturing process separate from the addition of TPA. However, it can be advantageous to introduce certain additives with the TPA, i.e. prior to the PET manufacturing process, especially co-monomers, such as, isophthalic acid and dyes or colorants which are thermally stable. Thus, co-monomers, catalyst(s), and additives can be introduced and intimately mixed with the TPA during the TPA manufacturing process rather than during the PET manufacturing process. Specific TPA manufacturing steps in which the intimate introduction of additive(s) can be achieved include addition at the solid liquid separation device for isolating the TPA cake, at any drying equipment, at or in any conveyance line or process pipeline, and prior to shipping the TPA product in any container. Thus, the TPA product in any form, whether dry solids (with residual water or acetic acid), wet cake (with some liquid water, or methanol, or EG, or some other diol or co-monomer, or mixtures), wet paste (with some liquid water, or methanol, or EG, or some other diol or co-monomer, or mixtures), or slurry (with water, or methanol, or EG, or some other diol or co-monomer, or mixtures), can be enriched prior to use in PET manufacture.

Figure 9:
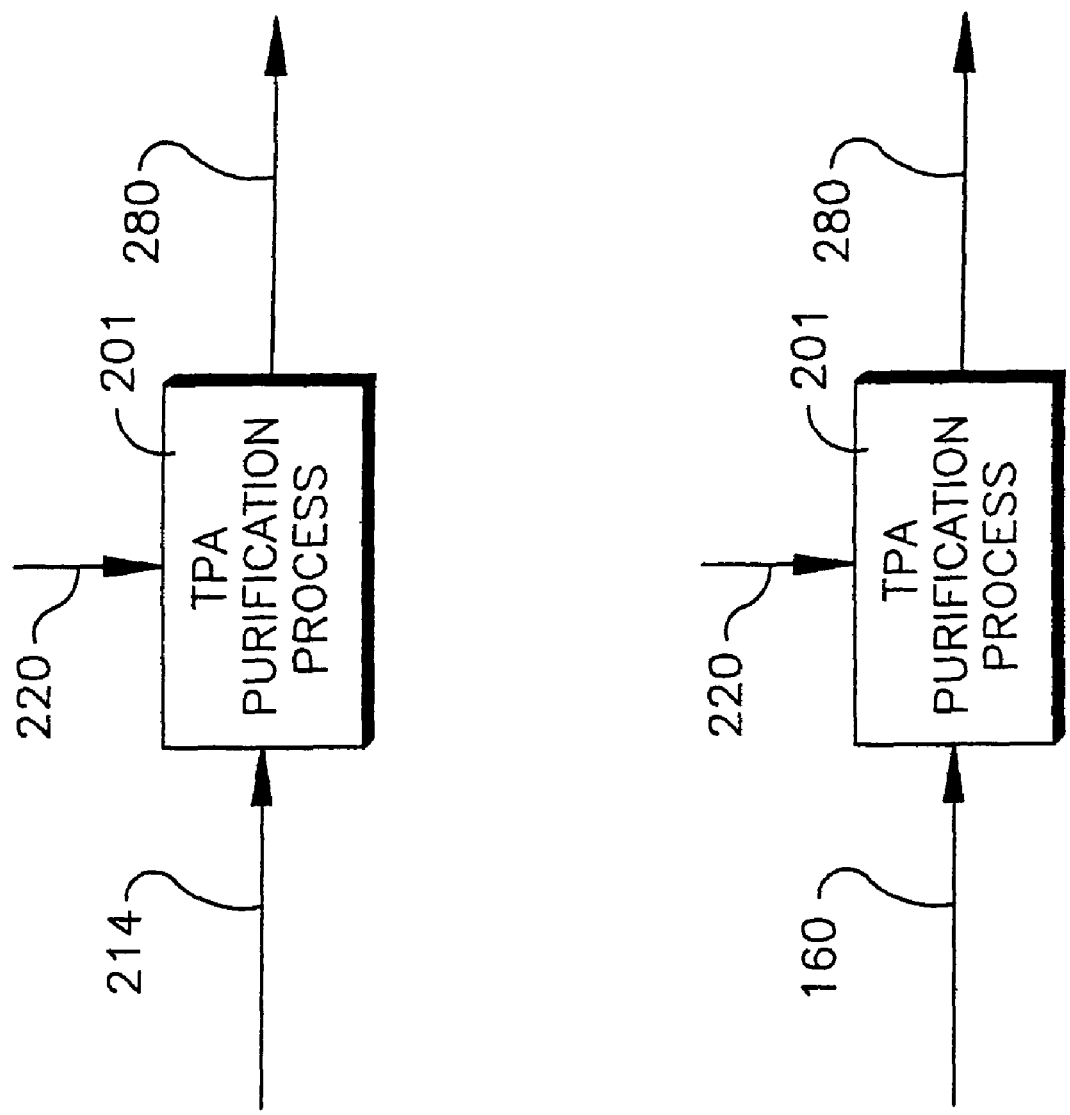
FIG. 9 illustrates various embodiments of the invention wherein a carboxylic acid composition 214 and/or a crystallized slurry composition 160 are enriched.

In addition, FIG. 9 depicts that the enrichment feed 220 can be introduced and enrichment can occur at any point from the crystallized slurry composition 160 to the dried carboxylic acid composition 280.

Figure 10:
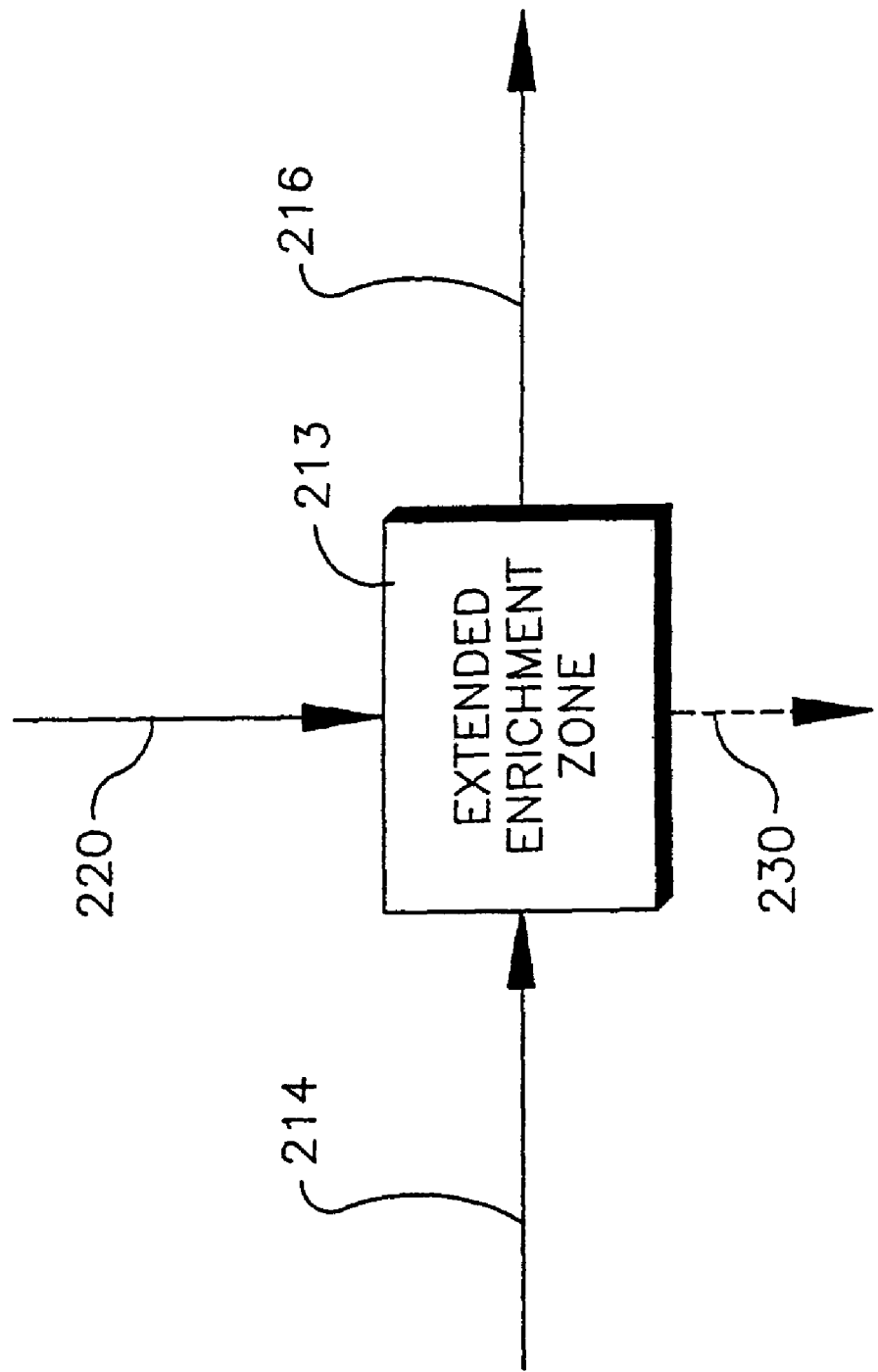
FIG. 10 illustrates various embodiments of the invention wherein a carboxylic acid composition 214 is enriched in an extended enrichment zone 213.

Another embodiment of the invention is provided in FIG. 10. The enrichment process can be conducted on a carboxylic acid composition 214 in an extended enrichment zone 213 to produce an enriched carboxylic acid composition 216. The enrichment feed 220 can comprise any composition previously or subsequently disclosed. There are no limitations on the carboxylic acid composition other than the carboxylic acid composition 214 comprises a carboxylic acid, optional solvent, and optionally a catalyst. In another embodiment of the invention the carboxylic acid composition can be used to produce the dried carboxylic acid composition 280.

Figure 11:
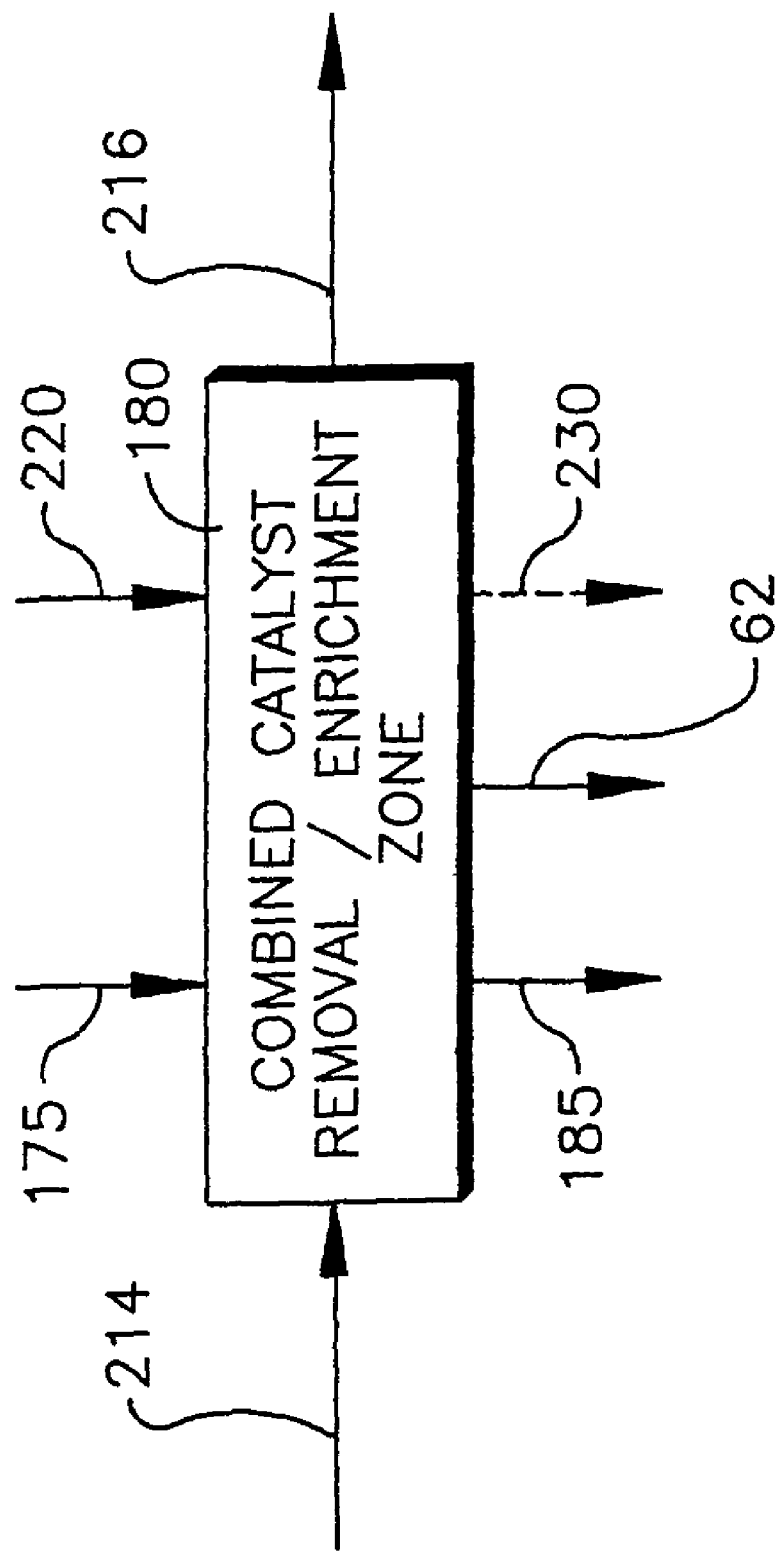
FIG. 11 illustrates various embodiments of the invention wherein the enrichment zone 210 and the catalyst removal zone 180 can be combined into at least one combined catalyst removal/enrichment zone 181 or at least one device that accomplishes both functions.

It should also be pointed out that in another embodiment of the invention, the enrichment zone 210 and the catalyst removal zone 180 can be combined into one zone comprising at least one device that accomplishes both functions as shown in FIG. 11.

There are no special limitations for the enrichment feed 220 other than it has a composition suitable to enrich the post catalyst removal composition 200. For example, the enrichment feed 220 can be a solid, a wash, a slurry, a paste, solids, solution or gas entrained liquid or solid. In an embodiment of the invention, the enrichment feed 220 comprises compositions capable of making the dried carboxylic acid cake composition 280. In another embodiment of the invention, the enrichment feed 220 are only solids and are added at one point or throughout the process to produce the dried carboxylic acid cake composition 280.

FIGS. 12, 13, 14 and 15 illustrate one embodiment of the invention showing how an enrichment feed 220 can be obtained and how the enrichment feed 220 is utilized through the process. In FIGS. 12, 13, 14, and 15, the enrichment feed(s) are depicted as stream 220. This is to illustrate that the enrichment feed(s) 220 can be taken from a variety of sources or one source and the enrichment feed(s) can have a variety of different compositions, different physical forms, and different addition points in the process. Also, the enrichment feed 220 can be added at one time, intermittently, or gradually throughout the process.

Figure 15:
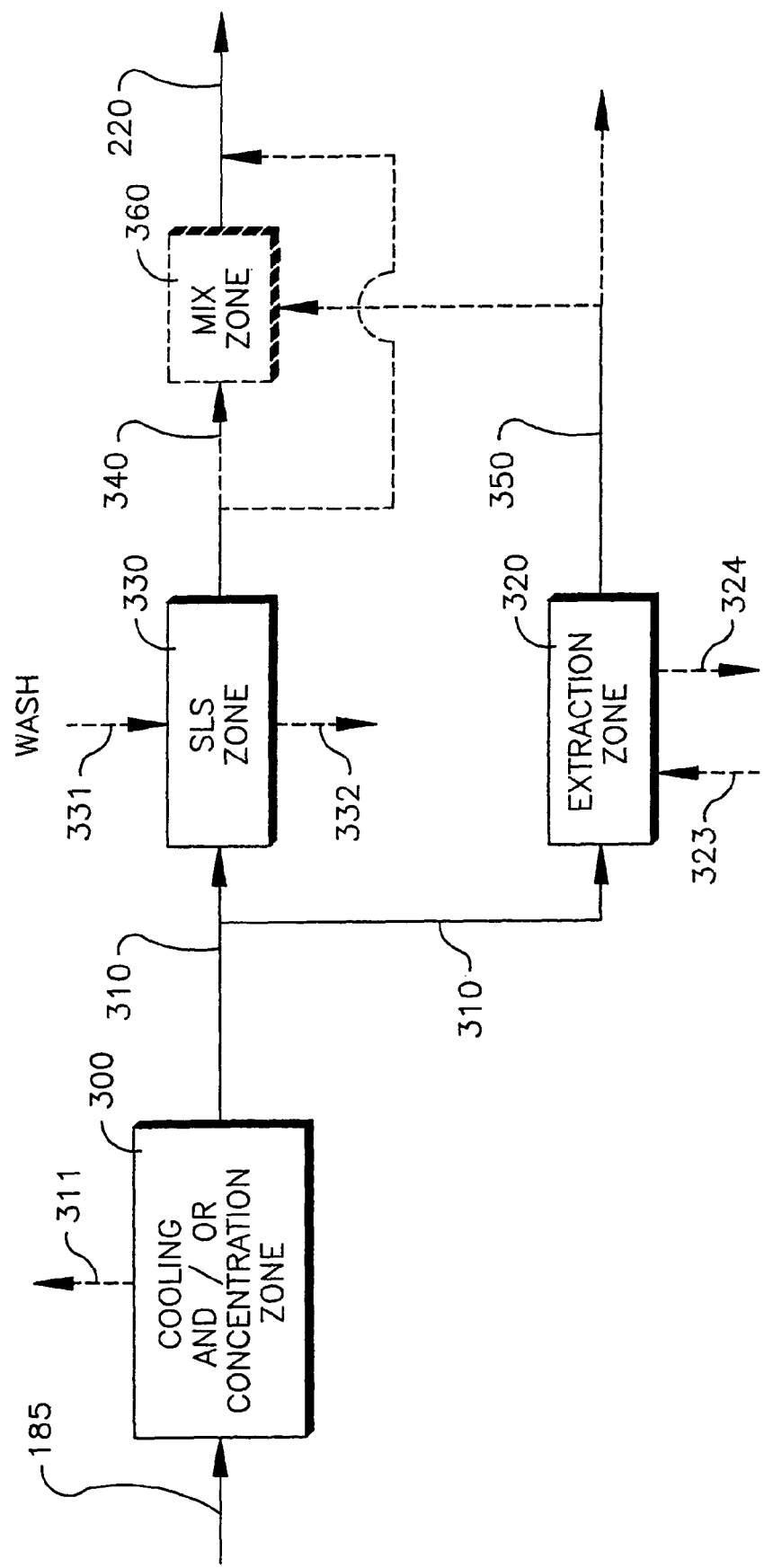

FIG. 15 illustrates one embodiment of the invention on how an enrichment feed 220 can be obtained. At least a portion of the catalyst rich liquor 185 is fed to a cooling and/or concentration zone 300 to generate a concentrated mother liquor stream 310 and a solvent stream 311. Sufficient solvent removal in the cooling and/or concentration zone 300 is achieved such that the concentrated catalyst rich stream 310 can have a % solids ranging from 10% by weight to 45% by weight.

A portion of the concentrated mother liquor stream 310 and an extraction solvent stream 323 is fed to an extraction zone 320 to generate a catalyst rich stream 324 and a catalyst depleted stream 350. The balance of the concentrated mother liquor stream 310 and a wash stream 331 is fed to a solid-liquid separation zone (SLS Zone), generating a wet cake stream 340 and wash liquor stream 332, comprising mother liquor and wash liquor. The wet cake stream 340 can be used as an enrichment feed 220 and a portion of the wet cake stream 340 can be sent to the product filter or product dryer to enrich the product stream with at least a portion of the contents of the wet cake stream 340. Alternatively, a portion of the wet cake stream 340 and a portion of catalyst depleted stream 350 can be fed to an optional mix zone where the two streams are mixed forming an enrichment feed 220 and a portion of this stream can be sent to a product filter or product dryer to enrich the product stream with at least a portion of the contents of enrichment feed 220.

The extraction zone 320 comprises at least one extractor. The extraction solvent 323 used in the extractor should be substantially water-insoluble to minimize the amount of organic solvent dissolved in the aqueous fraction. Additionally, the extraction solvent 323 is preferably an azeotropic agent which serves to assist solvent recovery from the organic extract. Solvents which have proven to be particularly useful are C1 to C6 alkyl acetates, particularly n-propyl acetate (n-PA), isopropyl acetate, isobutyl acetate, sec-butyl acetate, ethyl acetate and n-butyl acetate, although other water-insoluble organic solvents having an appropriate density and a sufficiently low boiling point may also be used, such as p-xylene. N-propyl acetate and isopropyl acetate are particularly preferred due to their relatively low water solubility, excellent azeotropic behavior, and their ability to remove the remaining acetic acid as well as high-boiling organic impurities from the aqueous mixture.

The extraction can be effected using solvent ratios from about 1 to about 4 parts by weight solvent per part of extractor feed depending on the extractor feed composition. Space velocities of the combined feeds to the extractor generally range from 1 to about 3 hr$^{-1}$. Although the extraction can be done at ambient temperature and pressure, heating the solvent and extractor to about 30° C. to about 70° C., or about 40° C. to about 60° C., can be used.

Figure 12:
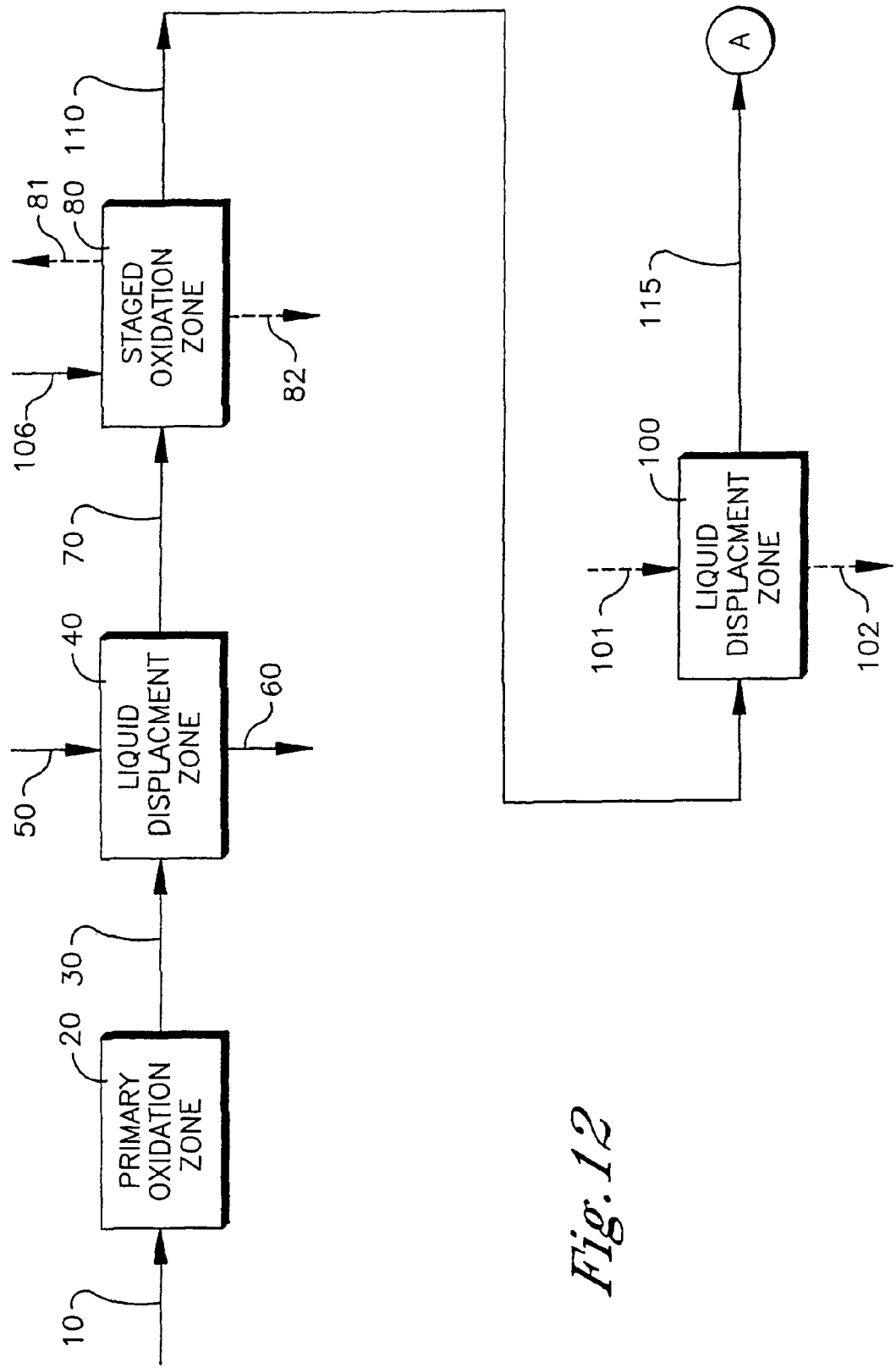
FIGS. 12, 13, 14 and 15 Illustrates an embodiment of the invention showing multiple enrichment feeds 220 in a given process.
Figure 13:
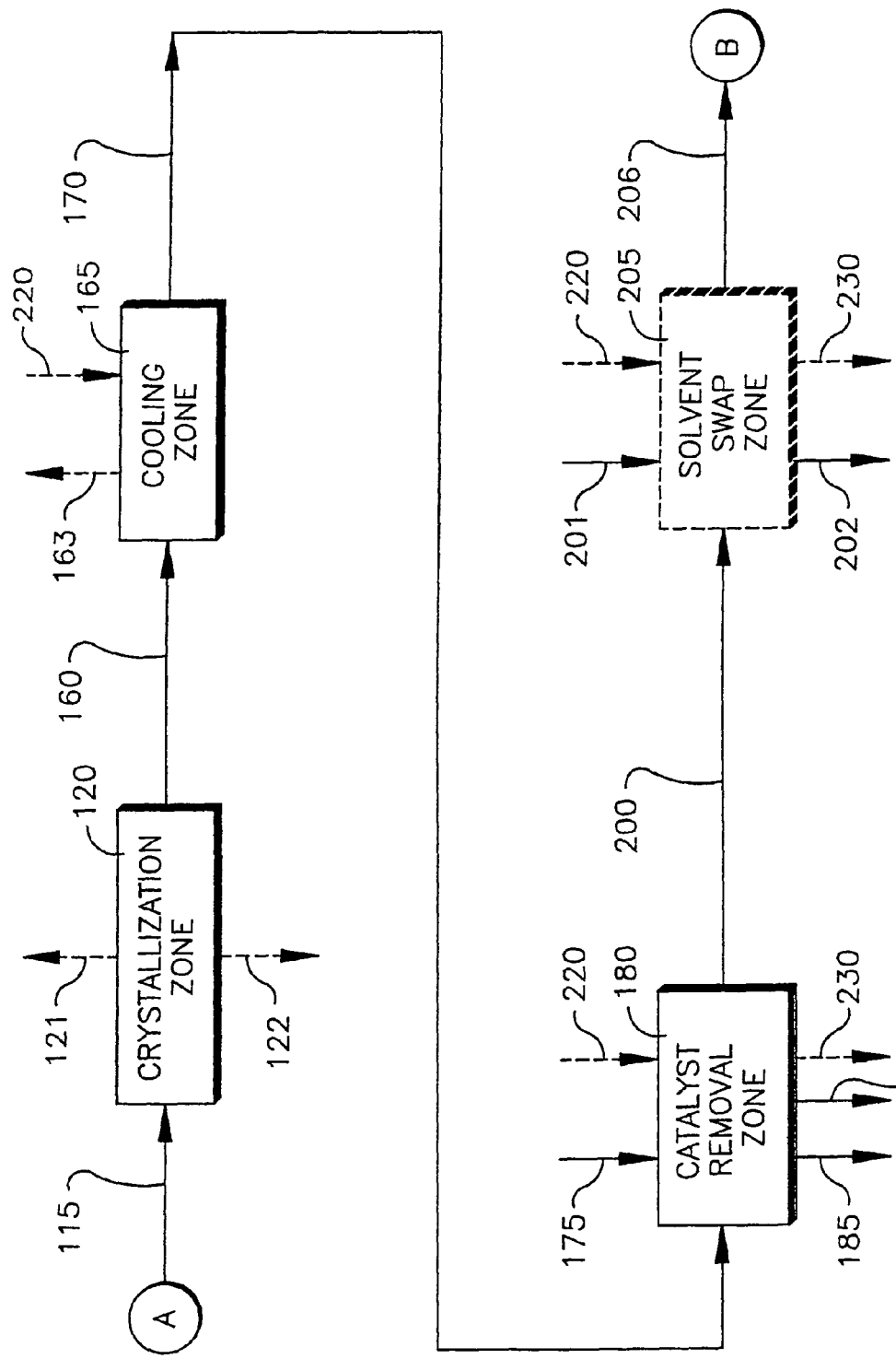
Figure 14:
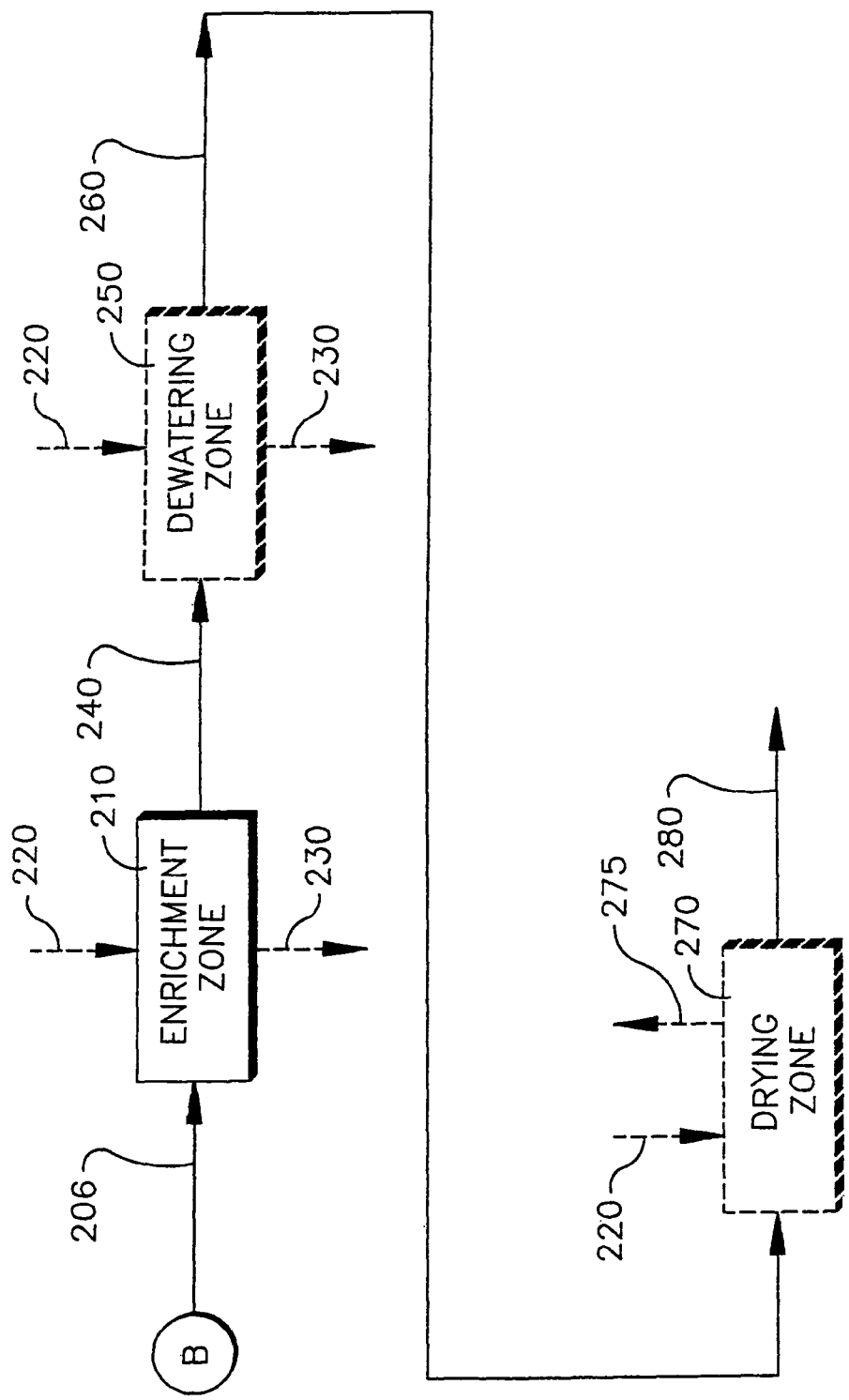

FIGS. 12, 13, and 14 illustrate one embodiment of the invention showing how an enrichment feed 220 can be utilized throughout the process. Aromatic feed stock 10 comprising reactants and catalyst are fed to the primary oxidation zone 20 generating a crude carboxylic acid composition 30. The crude carboxylic acid composition 30 and a solvent stream 50 are fed to liquid displacement zone 40 to achieve a partial solvent swap exchanging a portion of the oxidation solvent present in stream 30 with pure solvent generating a displaced solvent stream 60 and a slurry composition stream 70. The slurry composition 70 and a gas stream containing oxygen 106 are fed to a staged oxidation zone 80 to generate a staged oxidation composition 110. The staged oxidation composition 110 and a solvent stream 101 are fed to a liquid displacement zone 100 to achieve a partial solvent swap exchanging a portion of the oxidation solvent present in the staged oxidation composition 110 with pure solvent generating a displaced solvent stream 102 and a post solvent swap staged oxidation composition 115. The post solvent swap staged oxidation composition 115 is fed to a crystallization zone 120 generating a crystallized slurry composition Stream 160, an optional solvent vapor stream 121, and an optional liquid solvent stream 122. The crystallized slurry composition stream 160 and an optional enrichment feed 220 is fed to a cooling zone 165 where a cooled carboxylic acid composition stream 170 and an optional oxidation solvent stream 163 is generated. The cooled carboxylic acid composition 170, a wash feed 175, and an optional enrichment feed 220 are fed to a catalyst removal zone 180 to generate a post catalyst removal composition 200, the catalyst rich liquor 185, and a wash liquor 62, and a depleted enrichment feed 230. The post catalyst removal composition 200, swap solvent stream 201, and an optional enrichment fee 220 are fed to an optional solvent swap zone 205 to generate a swap solvent liquor 202, and post solvent swap composition 206. The post solvent swap composition 206 and an enrichment feed 220 are fed to an enrichment zone 210 to generate an enriched carboxylic acid composition Stream 240 and a depleted enrichment feed 230. The enriched composition 240 and an optional enrichment feed 220 are fed to an optional dewatering zone 250 to generate a dewatered carboxylic acid composition 260.

The catalyst removal zone 180, solvent swap zone 205, enrichment zone 210, dewatering zone 250, and optionally the drying zone 270 can be achieved in a single solid liquid separation device, preferably a continuous pressure or vacuum filter, and most preferably a vacuum belt filter. A continuous pressure drum filter or a rotary vacuum drum filter can also be used. The dewatered enriched carboxylic acid composition 260, and an optional enrichment feed 220 are fed to an optional drying zone 270 to generate a dry enriched carboxylic acid composition 280 and a solvent vapor stream 275.

In another embodiment of the invention, the enrichment feed 220 comprises water in a quantity greater than 50% by weight. In another embodiment of the invention, the enrichment feed 220 comprises water in a quantity greater than 75% by weight. In another embodiment of the invention, the enrichment feed 220 comprises water in a quantity greater than 95% by weight. In another embodiment of the invention, the enrichment feed 220 comprises water in a quantity greater than 99% by weight.

In another embodiment of the invention, the post catalyst removal composition 200 enters the enrichment zone 210 at a temperature in a range of about 200° C. to the freezing point of the enrichment feed 220. In another embodiment of the invention, the post catalyst removal composition 200 enters the enrichment zone 210 at a temperature in a range of about 100° C. to the freezing point of the enrichment feed 220. In another embodiment of the invention, the post catalyst removal composition 200 enters the enrichment zone 210 at a temperature in a range of about 200° C. to about 0° C. In another embodiment of the invention, the post catalyst removal composition 200 enters the enrichment zone 210 at a temperature in a range of about 0° C. to 100° C. Other ranges are less than 100° C. to 20° C.; and 40° C. to less than 100° C.

The enrichment zone 210 comprises at least one device sufficient to provide a sufficient amount of contact time between the enrichment feed 220 and the post catalyst removal composition 200 to allow for at least one compound selected from the group consisting of benzoic acid, isophthalic acid, phthalic acid, trimellitic acid, hydroxybenzoic acid isomers, hydroxymethylbenzoic acid isomers, and toluic acid isomers to be enriched. In another embodiment of the invention, the enrichment zone 210 or extended enrichment zone 213 comprises a device that provides a sufficient amount of contact time between the enrichment feed and the post catalyst removal composition 200 or carboxylic acid composition 214 to allow monomers, co-monomers, additives, and other compounds useful in the production of polyesters to be enriched. In another embodiment of the invention, the enrichment zone 210 or extended enrichment zone 213 comprises at least one device selected from the group consisting of a belt filter, pressure filter, rotary pressure filter, centrifuges capable of adding solids and or a wash stream such as a perforated basket centrifuge, a disk stack centrifuge etc, and the like.

In another embodiment of the invention, the enriched composition 240 on a dry solids basis encompasses all possible combinations of compositions of the dried carboxylic acid composition 280 described subsequently in this disclosure. Dry solids basis will be described subsequently in this disclosure.

All compositions are measured on a dry solids basis to be described subsequently in the disclosure. All measurements and claims in ppm are in ppm by weight on a dry solids basis.

Step (h) comprises optionally dewatering the enriched composition 240 in a dewatering zone 250 to form a dewatered post catalyst removal composition 260.

The dewatering can be conducted by any means know in the art. The dewatering results in the dewatered post catalyst removal composition 260 having a moisture content of less than 25% by weight moisture. Other moisture content ranges are less than 15% by weight moisture or less than 10% by weight moisture or less than 5% by weight moisture. In yet another embodiment of the invention, dewatering can be accomplished through the use of mostly mechanical means for drying and wherein the majority of the drying is not accomplished through evaporation. Majority as used herein means greater than 50%.

Step (i) comprises filtering and optionally drying the enriched composition 240 or the dewatered post catalyst removal composition 260 in a filtration and drying zone 270 to remove a portion of the solvent from the enriched composition 240 or the dewatered post catalyst removal composition 260 to produce the dried carboxylic acid composition 280.

The enriched composition 240 or the dewatered post catalyst removal composition 260 is withdrawn from the enrichment zone 210 or the dewatering zone 250 and fed to a filtration and drying zone 270.

In one embodiment of the invention, the filtration cake goes through an initial solvent removal step, is then rinsed with acid wash to remove residual catalyst, and then solvent is removed again before being sent to the dryers.

The drying zone 270 comprises at least one dryer and can be accomplished by any means known in the art that is capable of evaporating at least 10% of the volatiles remaining in the filter cake to produce the dried carboxylic acid composition 280. For example, indirect contact dryers including a rotary steam tube dryer, a Single Shaft Porcupine® Processor dryer, and a Bepex Solidaire® Processor can be used for the drying to produce a dried carboxylic acid composition 280. Direct contact dryers including a fluid bed dryer and drying in a convey line can be used for drying to produce a dried carboxylic acid composition 280. In another embodiment of the invention, drying can be accomplished in a solid-liquid separation device like a vacuum belt filter or a rotary pressure drum filter by allowing a gas stream to flow through the filter cake thus removing volatiles. In another embodiment of the invention, a solid-liquid separation device can comprise any combination of the following zones: a catalyst removal zone, an enrichment zone, a dewatering zone, and a drying zone. A dried carboxylic acid composition can be a carboxylic acid composition with less than 5% moisture, preferably less than 2% moisture, and more preferably less than 1% moisture, and even more preferably less than 0.5%, and yet more preferably less than 0.1%.

In an embodiment of the invention, the dried carboxylic acid composition 280 has a b* less than about 9.0. In another embodiment of the invention, the b* color of the dried carboxylic acid composition 280 is less than about 6.0. In another embodiment of the invention, the b* color of the dried carboxylic acid composition 280 is less than about 5.0. In another embodiment of the invention, the b* color of the dried carboxylic acid composition 280 is less than about 4.0. In another embodiment of the invention, the b* color of the dried carboxylic acid composition 280 is less than about 3. The b* color is one of the three-color attributes measured on a spectroscopic reflectance-based instrument. A Hunter Ultrascan XE instrument in reflectance mode is typically the measuring device. Positive readings signify the degree of yellow (or absorbance of blue), while negative readings signify the degree of blue (or absorbance of yellow).

Compositions Comprising at Least One Carboxylic Acid

I. In an embodiment of the invention, the dried carboxylic acid composition 280 comprises:

(1) carboxylic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight; and optionally, (2) (a) carboxybenzaldehyde (CBA) isomers in an amount ranging from 1 ppm to 1000 ppm, or ranging from 1 ppm to 500 ppm, or ranging from 1 ppm to 250 ppm, or ranging from 1 ppm to 125 ppm; or (b) toluic acid (TA) isomers in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
(i) carboxybenzaldehyde isomers in an amount ranging from 1 ppm to 1000 ppm, or ranging from 1 ppm to 500 ppm, or ranging from 1 ppm to 250 ppm or ranging from 1 ppm to 125 ppm;
(ii) toluic acid isomers in an amount ranging from 1 ppm to 500 ppm, or ranging from 1 ppm to 250 ppm, or ranging from 1 ppm to 125 ppm;
wherein the total concentration of carboxybenzaldehyde and toluic acid isomers ranges from 1 ppm to 2000 ppm, 1 ppm to 1000 ppm, or from 1 ppm to 500 ppm, or from 1 ppm to 250 ppm, or from 1 ppm to 125 ppm;

and (3) at least one, or at least two, or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or all of the following:

(a) terephthalic acid in an amount at least 50 ppm, or ranging from 50 ppm to 2000 ppm, or ranging from 75 ppm to 1500 ppm, or ranging from 100 ppm or 1000 ppm, or ranging from 150 ppm or 500 ppm;

(b) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm;

(c) phthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm;

(d) benzene-tricarboxylic acid isomers in an amount of at least 125 ppm, or ranging from 125 ppm to 1000 ppm, or ranging from 150 ppm to 750 ppm, or ranging from 175 ppm to 500 ppm;

(e) benzoic acid in an amount of at least 50 ppm, or at least 75 ppm, or at least 100 ppm; or ranging from 50 ppm to 500 ppm, or ranging from 75 ppm to 400 ppm, or ranging from 100 ppm to 300 ppm;

(f) hydroxybenzoic acid isomers in an amount of at least 3 ppm, at least 5 ppm, or at least 20 ppm, or ranging from 3 ppm to 200 ppm, or ranging from 5 ppm to 175 ppm, or ranging from 20 ppm to 150 ppm;

(g) hydroxymethylbenzoic acid isomers in an amount of at least 40 ppm, or at least 80 ppm, or at least 100 ppm, or ranging from 40 ppm to 200 ppm, or ranging from 80 ppm to 180, or ranging from 100 ppm to 160 ppm;

(h) dicarboxybiphenyl isomers in an amount ranging from 20 ppm to 150 ppm, or ranging from 25 ppm to 100 ppm, or ranging from 25 ppm to 75 ppm;

(i) dicarboxystilbene isomers in an amount ranging from greater than 7 ppm; or greater than 10 ppm;

(j) tricarboxybiphenyl isomers in an amount ranging from 8 ppm to 100 ppm, or ranging from 9 ppm to 50 ppm, or ranging from 10 ppm to 25 ppm;

(k) tricarboxybenzophenone isomers in an amount ranging from 5 ppm to 100 ppm, or ranging from 6 ppm to 75 ppm, or ranging from 7 ppm to 60 ppm;

(l) dicarboxybenzophenone isomers in an amount ranging from 10 ppm to 150 ppm, or ranging from 12 ppm to 100 ppm, or ranging from 15 ppm to 75 ppm;

(m) dicarboxybenzil isomers in an amount ranging from 1 ppm to 30 ppm, or ranging from 2 ppm to 20 ppm, or ranging from 3 ppm to 10 ppm;

(n) form-acet-hydroxybenzoic acid isomers in an amount ranging from 1 ppm to 20 ppm, or ranging from 2 ppm to 15 ppm, or ranging from 3 ppm to 10 ppm;

(o) acet-hydroxymethylbenzoic acid isomers in an amount ranging from 1 ppm to 30 ppm, or ranging from 2 ppm to 20 ppm, or ranging from 3 ppm to 15 ppm;

(p) a-bromo-toluic acid isomers in an amount ranging from 1 ppm to 100 ppm, or ranging from 2 ppm to 50 ppm, or ranging from 5 ppm to 25 ppm;

(q) bromo-benzoic acid in an amount ranging from 5 ppm to 50 ppm, or ranging from 10 ppm to 40 ppm, or ranging from 15 ppm to 35 ppm;

(r) bromo-acetic acid in an amount ranging from 1 ppm to 10 ppm;

(s) tolualdehye isomers in an amount ranging from 7 ppm to 50 ppm, or ranging from 8 ppm to 25 ppm, or ranging from 9 ppm to 20 ppm;

(t) phthaldehyde isomers in an amount ranging from 0.25 ppm to 10 ppm, or ranging from 0.5 ppm to -5 ppm, or ranging from 0.75 ppm to 2 ppm; wherein the compound or compounds selected in (3) are different than the compound or compounds selected in (1) and (2);

and optionally, (4) at least one, or at least two, or at least three, or at least four, or at least five or at least six, or at least seven, or at least eight, or all of the following:

(a) terephthalic acid in an amount of at least 1 ppm, or ranging from 1 ppm to 5000 ppm, or ranging from 5 ppm to 2500 ppm, or ranging from 10 ppm to 2000 ppm, or ranging from 15 ppm to 1000 ppm, or ranging from 20 ppm to 500 ppm;

(b) isophthalic acid in an amount of at least 1 ppm, or ranging from 1 ppm to 5000 ppm, or ranging from 5 ppm to 2500 ppm, or ranging from 10 ppm to 2000 ppm, or ranging from 15 ppm to 1000 ppm, or ranging from 20 ppm to 500 ppm;

(c) phthalic acid in an amount of at least 1 ppm, or ranging from 1 ppm to 3000 ppm, or ranging from 2 ppm to 2000 ppm, or ranging from 3 ppm to 1000 ppm, or ranging from 4 ppm to 500 ppm;

(d) benzene-tricarboxylic acid isomers in an amount of at least 1 ppm, or ranging from 1 ppm to 3000 ppm, or ranging from 5 ppm to 2000 ppm, or ranging from 10 ppm to 1000 ppm, or ranging from 20 ppm to 500 ppm;

(e) benzoic acid in an amount of at least 1 ppm, or ranging from 1 ppm to 3000 ppm, or ranging from 5 ppm to 2000 ppm, or ranging from 10 ppm to 1000 ppm, or ranging from 20 ppm to 500 ppm;

(f) hydroxybenzoic acid isomers in an amount of at least 1 ppm, or ranging from 1 ppm to 500 ppm, or ranging from 5 ppm to 400 ppm, or ranging from 10 ppm to 200 ppm;

(g) hydroxymethylbenzoic acid isomers in an amount of at least 1 ppm, or ranging from 1 ppm to 500 ppm, or ranging from 5 ppm to 400 ppm, or ranging from 10 ppm to 200 ppm;

(h) dicarboxybiphenyl isomers in an amount of at least 1 ppm, or ranging from 1 ppm to 500 ppm, or ranging from 5 ppm to 400 ppm, or ranging from 10 ppm to 200 ppm;

wherein the compound or compounds selected in (4) are different than the compound or compounds selected in (3).

II. In another embodiment of the invention, the dried carboxylic acid composition 280 comprises:

(1) carboxylic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) carboxybenzaldehyde isomers (CBA) in an amount ranging from 1 ppm to 1000 ppm, or ranging from 1 ppm to 500 ppm, or ranging from 1 ppm to 250 ppm, or ranging from 1 ppm to 125 ppm; or (b) toluic acid isomers (TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
(1) carboxybenzaldehyde isomers (CBA) in an amount ranging from 1 ppm to 1000 ppm, or ranging from 1 ppm to 500 ppm, or ranging from 1 ppm to 250 ppm or ranging from 1 ppm to 125 ppm;
(2) toluic acid isomers (TA) in an amount ranging from 1 ppm to 500 ppm, or ranging from 1 ppm to 250 ppm, or ranging from 1 ppm to 125 ppm;
wherein the total concentration of CBA and TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least two, or at least three, or at least four, or at least five, or at least six, or seven, or all of the following:

(a) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

(c) dicarboxybiphenyl isomers in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

(d) phthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm, or ranging from 20 ppm, 50 ppm, 100 ppm to 500 ppm, or 750 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 750 ppm, or 1000 ppm to 2000 ppm, or 0.5 wt %, or 1 wt %, or 2 wt %, or 3 wt %, or 5 wt %, or 10 wt %, or 25 wt %, or 49 wt %;

(e) hydroxybenzoic acid isomers ranging from 3 ppm to 200 ppm, or ranging from 5 ppm to 175 ppm, or ranging from 20 ppm to 150 ppm, or ranging from 3 ppm, or 5 ppm or 20 ppm to 150 ppm, or 175 ppm, or 200 ppm, or 500 ppm, or 1000 ppm;

(f) hydroxymethylbenzoic acid isomers in an amount of at least 40 ppm, or at least 80 ppm, or at least 100 ppm, or ranging from 40 ppm to 200 ppm, or ranging from 80 ppm to 180, or ranging from 100 ppm to 160 ppm, or ranging from 40 ppm, or 80 ppm, or 100 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %;

(g) benzoic acid ranging from 60 ppm to 500 ppm, or ranging from 75 ppm to 400 ppm, or ranging from 100 ppm to 300 ppm, or ranging from 60 ppm, or 75 ppm, or 100 ppm to 300 ppm, or 500 ppm, or 1000 ppm (h) terephthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm, or ranging from 20 ppm, 50 ppm, 100 ppm to 500 ppm, or 750 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 750 ppm, or 1000 ppm to 2000 ppm, or 0.5 wt %, or 1 wt %, or 2 wt %, or 3 wt %, or 5 wt %, or 10 wt %, or 25 wt %, or 49 wt %;

III. In an embodiment of the invention, the dried carboxylic acid composition 280 comprises:

(1) carboxylic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) carboxybenzaldehyde isomers (CBA) in an amount ranging from 1 ppm to 1000 ppm, or ranging from 1 ppm to 500 ppm, or ranging from 1 ppm to 250 ppm, or ranging from 1 ppm to 125 ppm; or (b) toluic acid isomers (TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
(1) carboxybenzaldehyde isomers (CBA) in an amount ranging from 1 ppm to 1000 ppm, or ranging from 1 ppm to 500 ppm, or ranging from 1 ppm to 250 ppm or ranging from 1 ppm to 125 ppm;
(2) toluic acid isomers (TA) in an amount ranging from 1 ppm to 500 ppm, or ranging from 1 ppm to 250 ppm, or ranging from 1 ppm to 125 ppm;
wherein the total concentration of CBA and TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least two, or at least three, or at least four, or five, or all of the following:

(a) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

(c) dicarboxybiphenyl isomers in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

(d) phthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm, or ranging from 20 ppm, 50 ppm, 100 ppm to 500 ppm, or 750 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 750 ppm, or 1000 ppm to 2000 ppm, or 0.5 wt %, or 1 wt %, or 2 wt %, or 3 wt %, or 5 wt %, or 10 wt %, or 25 wt %, or 49 wt %;

(e) benzoic acid ranging from 60 ppm to 500 ppm, or ranging from 75 ppm to 400 ppm, or ranging from 100 ppm to 300 ppm, or ranging from 60 ppm, or 75 ppm, or 100 ppm to 300 ppm, or 500 ppm, or 1000 ppm.

(f) terephthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm, or ranging from 20 ppm, 50 ppm, 100 ppm to 500 ppm, or 750 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 750 ppm, or 1000 ppm to 2000 ppm, or 0.5 wt %, or 1 wt %, or 2 wt %, or 3 wt %, or 5 wt %, or 10 wt %, or 25 wt %, or 49 wt %;

IV. In an embodiment of the invention, the dried carboxylic acid composition 280 comprises:

(1) carboxylic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) carboxybenzaldehyde isomers (CBA) in an amount ranging from 1 ppm to 1000 ppm, or ranging from 1 ppm to 500 ppm, or ranging from 1 ppm to 250 ppm, or ranging from 1 ppm to 125 ppm; or (b) toluic acid isomers (TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
(1) carboxybenzaldehyde isomers (CBA) in an amount ranging from 1 ppm to 1000 ppm, or ranging from 1 ppm to 500 ppm, or ranging from 1 ppm to 250 ppm or ranging from 1 ppm to 125 ppm;
(2) toluic acid isomers (TA) in an amount ranging from 1 ppm to 500 ppm, or ranging from 1 ppm to 250 ppm, or ranging from 1 ppm to 125 ppm;
wherein the total concentration of CBA and TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least two, or at least three, or four, or all of the following:
(a) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;
(b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;
(c) dicarboxybiphenyl isomers in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;
(d) phthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm, or ranging from 20 ppm, 50 ppm, 100 ppm to 500 ppm, or 750 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 750 ppm, or 1000 ppm to 2000 ppm, or 0.5 wt %, or 1 wt %, or 2 wt %, or 3 wt %, or 5 wt %, or 10 wt %, or 25 wt %, or 49 wt %;
(e) terephthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm, or ranging from 20 ppm, 50 ppm, 100 ppm to 500 ppm, or 750 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 750 ppm, or 1000 ppm to 2000 ppm, or 0.5 wt %, or 1 wt %, or 2 wt %, or 3 wt %, or 5 wt %, or 10 wt %, or 25 wt %, or 49 wt %;

V. In an embodiment of the invention, the dried carboxylic acid composition 280 comprises:

(1) carboxylic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) carboxybenzaldehyde isomers (CBA) in an amount ranging from 1 ppm to 1000 ppm, or ranging from 1 ppm to 500 ppm, or ranging from 1 ppm to 250 ppm, or ranging from 1 ppm to 125 ppm; or (b) toluic acid isomers (TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
(1) carboxybenzaldehyde isomers (CBA) in an amount ranging from 1 ppm to 1000 ppm, or ranging from 1 ppm to 500 ppm, or ranging from 1 ppm to 250 ppm or ranging from 1 ppm to 125 ppm;
(2) toluic acid isomers (TA) in an amount ranging from 1 ppm to 500 ppm, or ranging from 1 ppm to 250 ppm, or ranging from 1 ppm to 125 ppm;
wherein the total concentration of CBA and TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least two, or three, or all of the following:
(a) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;
(b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;
(c) dicarboxybiphenyl isomers in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

(d) terephthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

VI. In an embodiment of the invention, the dried carboxylic acid composition 280 comprises:

(1) carboxylic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) carboxybenzaldehyde isomers (CBA) in an amount ranging from 1 ppm to 1000 ppm, or ranging from 1 ppm to 500 ppm, or ranging from 1 ppm to 250 ppm, or ranging from 1 ppm to 125 ppm; or (b) toluic acid isomers (TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
  (1) carboxybenzaldehyde isomers (CBA) in an amount ranging from 1 ppm to 1000 ppm, or ranging from 1 ppm to 500 ppm, or ranging from 1 ppm to 250 ppm or ranging from 1 ppm to 125 ppm;
  (2) toluic acid isomers (TA) in an amount ranging from 1 ppm to 500 ppm, or ranging from 1 ppm to 250 ppm, or ranging from 1 ppm to 125 ppm;
  wherein the total concentration of CBA and TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least two, or all of the following:
  (a) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;
  (b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;
  (c) dicarboxybiphenyl isomers in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

VII. In an embodiment of the invention, the dried carboxylic acid composition 280 comprises:

(1) carboxylic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) carboxybenzaldehyde isomers (CBA) in an amount ranging from 1 ppm to 1000 ppm, or ranging from 1 ppm to 500 ppm, or ranging from 1 ppm to 250 ppm, or ranging from 1 ppm to 125 ppm; or (b) toluic acid isomers (TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
  (1) carboxybenzaldehyde isomers (CBA) in an amount ranging from 1 ppm to 1000 ppm, or ranging from 1 ppm to 500 ppm, or ranging from 1 ppm to 250 ppm or ranging from 1 ppm to 125 ppm;
  (2) toluic acid isomers (TA) in an amount ranging from 1 ppm to 500 ppm, or ranging from 1 ppm to 250 ppm, or ranging from 1 ppm to 125 ppm;
  wherein the total concentration of CBA and TA ranges from 1 ppm to 2000 ppm, 1 ppm to 1000 ppm, or from 1 ppm to 500 ppm, or from 1 ppm to 250 ppm, or from 1 ppm to 125 ppm;

and (3) both of the following:
  (a) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;
  (b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

VII. In an embodiment of the invention, the dried carboxylic acid composition 280 comprises:

(1) carboxylic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) carboxybenzaldehyde isomers (CBA) in an amount ranging from 1 ppm to 1000 ppm, or ranging from 1 ppm to 500 ppm, or ranging from 1 ppm to 250 ppm, or ranging from 1 ppm to 125 ppm; or (b) toluic acid isomers (TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
(1) carboxybenzaldehyde isomers (CBA) in an amount ranging from 1 ppm to 1000 ppm, or ranging from 1 ppm to 500 ppm, or ranging from 1 ppm to 250 ppm or ranging from 1 ppm to 125 ppm;
(2) toluic acid isomers (TA) in an amount ranging from 1 ppm to 500 ppm, or ranging from 1 ppm to 250 ppm, or ranging from 1 ppm to 125 ppm;
wherein the total concentration of CBA and TA ranges from 1 ppm to 2000 ppm, 1 ppm to 1000 ppm, or from 1 ppm to 500 ppm, or from 1 ppm to 250 ppm, or from 1 ppm to 125 ppm;

and (3) both of the following:
(a) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;
(b) dicarboxybiphenyl isomers in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

IX. In an embodiment of the invention, the dried carboxylic acid composition 280 comprises:

(1) carboxylic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) carboxybenzaldehyde isomers (CBA) in an amount ranging from 1 ppm to 1000 ppm, or ranging from 1 ppm to 500 ppm, or ranging from 1 ppm to 250 ppm, or ranging from 1 ppm to 125 ppm; or (b) toluic acid isomers (TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
(1) carboxybenzaldehyde isomers (CBA) in an amount ranging from 1 ppm to 1000 ppm, or ranging from 1 ppm to 500 ppm, or ranging from 1 ppm to 250 ppm or ranging from 1 ppm to 125 ppm;
(2) toluic acid isomers (TA) in an amount ranging from 1 ppm to 500 ppm, or ranging from 1 ppm to 250 ppm, or ranging from 1 ppm to 125 ppm;
wherein the total concentration of CBA and TA ranges from 1 ppm to 2000 ppm, 1 ppm to 1000 ppm, or from 1 ppm to 500 ppm, or from 1 ppm to 250 ppm, or from 1 ppm to 125 ppm;

and (3) both of the following:
(a) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;
(b) dicarboxybiphenyl isomers in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

X. In an embodiment of the invention, the dried carboxylic acid composition 280 comprises:

(1) carboxylic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) carboxybenzaldehyde isomers (CBA) in an amount ranging from 1 ppm to 1000 ppm, or ranging from 1 ppm to 500 ppm, or ranging from 1 ppm to 250 ppm, or ranging from 1 ppm to 125 ppm; or (b) toluic acid isomers (TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
(1) carboxybenzaldehyde isomers (CBA) in an amount ranging from 1 ppm to 1000 ppm, or ranging from 1 ppm to 500 ppm, or ranging from 1 ppm to 250 ppm or ranging from 1 ppm to 125 ppm;
(2) toluic acid isomers (TA) in an amount ranging from 1 ppm to 500 ppm, or ranging from 1 ppm to 250 ppm, or ranging from 1 ppm to 125 ppm;
wherein the total concentration of CBA and TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least two, or all of the following:
(a) terephthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

(c) dicarboxybiphenyl isomers in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

XI. In an embodiment of the invention, the dried carboxylic acid composition 280 comprises:

(1) carboxylic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) carboxybenzaldehyde isomers (CBA) in an amount ranging from 1 ppm to 1000 ppm, or ranging from 1 ppm to 500 ppm, or ranging from 1 ppm to 250 ppm, or ranging from 1 ppm to 125 ppm; or (b) toluic acid isomers (TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
(1) carboxybenzaldehyde isomers (CBA) in an amount ranging from 1 ppm to 1000 ppm, or ranging from 1 ppm to 500 ppm, or ranging from 1 ppm to 250 ppm or ranging from 1 ppm to 125 ppm;
(2) toluic acid isomers (TA) in an amount ranging from 1 ppm to 500 ppm, or ranging from 1 ppm to 250 ppm, or ranging from 1 ppm to 125 ppm;
wherein the total concentration of CBA and TA ranges from 1 ppm to 2000 ppm, 1 ppm to 1000 ppm, or from 1 ppm to 500 ppm, or from 1 ppm to 250 ppm, or from 1 ppm to 125 ppm;

and (3) both of the following:
(a) terephthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

XII. In an embodiment of the invention, the dried carboxylic acid composition 280 comprises:

(1) carboxylic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) carboxybenzaldehyde isomers (CBA) in an amount ranging from 1 ppm to 1000 ppm, or ranging from 1 ppm to 500 ppm, or ranging from 1 ppm to 250 ppm, or ranging from 1 ppm to 125 ppm; or (b) toluic acid isomers (TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
(1) carboxybenzaldehyde isomers (CBA) in an amount ranging from 1 ppm to 1000 ppm, or ranging from 1 ppm to 500 ppm, or ranging from 1 ppm to 250 ppm or ranging from 1 ppm to 125 ppm;
(2) toluic acid isomers (TA) in an amount ranging from 1 ppm to 500 ppm, or ranging from 1 ppm to 250 ppm, or ranging from 1 ppm to 125 ppm;
wherein the total concentration of CBA and TA ranges from 1 ppm to 2000 ppm, 1 ppm to 1000 ppm, or from 1 ppm to 500 ppm, or from 1 ppm to 250 ppm, or from 1 ppm to 125 ppm;

and (3) both of the following:
(a) terephthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) dicarboxybiphenyl isomers in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

XIII. In another embodiment of the invention, the dried carboxylic acid composition 280 comprises:

(1) carboxylic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight; and (2) carboxybenzaldehyde isomers (CBA) in an amount ranging from 1 ppm to 500 ppm, and (3) all of the following:
(a) phthalic acid isomers in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

(c) dicarboxybiphenyl isomers in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

Isophthalic Acid Compositions

I. In an embodiment of the invention, the dried carboxylic acid composition 280 comprises:

(1) isophthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 3-carboxybenzaldehyde (3-CBA) in an amount ranging from 1 ppm to 1000 ppm, or ranging from 1 ppm to 500 ppm, or ranging from 1 ppm to 250 ppm, or ranging from 1 ppm to 125 ppm; or (b) m-toluic acid (m-TA isomers) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
(1) 3-carboxybenzaldehyde (3-CBA) in an amount ranging from 1 ppm to 1000 ppm, or ranging from 1 ppm to 500 ppm, or ranging from 1 ppm to 250 ppm or ranging from 1 ppm to 125 ppm;
(2) m-toluic acid isomers (m-TA) in an amount ranging from 1 ppm to 500 ppm, or ranging from 1 ppm to 250 ppm, or ranging from 1 ppm to 125 ppm;
wherein the total concentration of 3-CBA and m-TA ranges from 1 ppm to 2000 ppm, 1 ppm to 1000 ppm, or from 1 ppm to 500 ppm, or from 1 ppm to 250 ppm, or from 1 ppm to 125 ppm and (3) at least one, or at least two, or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or all of the following:

(a) terephthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm;

(b) phthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm;

(c) benzene-tricarboxylic acid isomers in an amount of at least 140 ppm, or ranging from 140 ppm to 1000 ppm, or ranging from 175 ppm to 750 ppm, or ranging from 200 ppm to 500 ppm;

(d) benzoic acid in an amount of at least 50 ppm, or at least 75 ppm, or at least 100 ppm; or ranging from 50 ppm to 500 ppm, or ranging from 75 ppm to 400 ppm, or ranging from 100 ppm to 300 ppm;

(e) 3-hydroxybenzoic acid in an amount of at least 3 ppm, at least 5 ppm, or at least 20 ppm, or ranging from 3 ppm to 200 ppm, or ranging from 5 ppm to 175 ppm, or ranging from 20 ppm to 150 ppm;

(f) 3-hydroxymethylbenzoic acid in an amount of at least 40 ppm, or at least 80 ppm, or at least 100 ppm, or ranging from 40 ppm to 200 ppm, or ranging from 80 ppm to 180, or ranging from 100 ppm to 160 ppm;

(g) 3,3'-dicarboxybiphenyl isomers in an amount ranging from 20 ppm to 150 ppm, or ranging from 25 ppm to 100 ppm, or ranging from 25 ppm to 75 ppm;

(h) dicarboxyanthraquinone isomers in an amount less than 1 ppm, or less than 0.5 ppm, or less than 0.4 ppm, or less than 0.35 ppm;

(i) dicarboxystilbene isomers in an amount ranging from greater than 7 ppm; or greater than 10 ppm;

(j) tricarboxybiphenyl isomers in an amount ranging from 8 ppm to 100 ppm, or ranging from 9 ppm to 50 ppm, or ranging from 10 ppm to 25 ppm;

(k) tricarboxybenzophenone isomers in an amount ranging from 5 ppm to 100 ppm, or ranging from 6 ppm to 75 ppm, or ranging from 7 ppm to 60 ppm;

(l) dicarboxybenzophenone isomers in an amount ranging from 10 ppm to 150 ppm, or ranging from 12 ppm to 100 ppm, or ranging from 15 ppm to 75 ppm;

(m) dicarboxybenzil isomers in an amount ranging from 1 ppm to 30 ppm, or ranging from 2 ppm to 20 ppm, or ranging from 3 ppm to 10 ppm;

(n) form-acet-hydroxybenzoic acid isomers in an amount ranging from 1 ppm to 20 ppm, or ranging from 2 ppm to 15 ppm, or ranging from 3 ppm to 10 ppm;

(o) acet-hydroxymethylbenzoic acid isomers in an amount ranging from 1 ppm to 30 ppm, or ranging from 2 ppm to 20 ppm, or ranging from 3 ppm to 15 ppm;

(p) a-bromo-m-toluic acid in an amount ranging from 1 ppm to 100 ppm, or ranging from 2 ppm to 50 ppm, or ranging from 5 ppm to 25 ppm;

(q) bromo-benzoic acid in an amount ranging from 5 ppm to 50 ppm, or ranging from 10 ppm to 40 ppm, or ranging from 15 ppm to 35 ppm;

(r) bromo-acetic acid in an amount ranging from 1 ppm to 10 ppm;

(s) m-tolualdehye in an amount ranging from 7 ppm to 50 ppm, or ranging from 8 ppm to 25 ppm, or ranging from 9 ppm to 20 ppm;

(t) isophthaldehyde in an amount ranging from 0.25 ppm to 10 ppm, or ranging from 0.5 ppm to-5 ppm, or ranging from 0.75 ppm to 2 ppm; and optionally (4) at least one, or at least two, or at least three, or at least four, or at least five or at least six, or at least seven, or all of the following:

(a) terephthalic acid in an amount of at least 1 ppm, or ranging from 1 ppm to 5000 ppm, or ranging from 5 ppm to 2500 ppm, or ranging from 10 ppm to 2000 ppm, or ranging from 15 ppm to 1000 ppm, or ranging from 20 ppm to 500 ppm;

(b) phthalic acid in an amount of at least 1 ppm, or ranging from 1 ppm to 3000 ppm, or ranging from 2 ppm to 2000 ppm, or ranging from 3 ppm to 1000 ppm, or ranging from 4 ppm to 500 ppm;

(c) benzene-tricarboxylic acid isomers in an amount of at least 1 ppm, or ranging from 1 ppm to 3000 ppm, or ranging from 5 ppm to 2000 ppm, or ranging from 10 ppm to 1000 ppm, or ranging from 20 ppm to 500 ppm;

(d) benzoic acid in an amount of at least 1 ppm, or ranging from 1 ppm to 3000 ppm, or ranging from 5 ppm to 2000 ppm, or ranging from 10 ppm to 1000 ppm, or ranging from 20 ppm to 500 ppm;

(e) 3-hydroxybenzoic acid in an amount of at least 1 ppm, or ranging from 1 ppm to 500 ppm, or ranging from 5 ppm to 400 ppm, or ranging from 10 ppm to 200 ppm;

(f) 3-hydroxymethylbenzoic acid in an amount of at least 1 ppm, or ranging from 1 ppm to 500 ppm, or ranging from 5 ppm to 400 ppm, or ranging from 10 ppm to 200 ppm;

(g) 3,3'-dicarboxybiphenyl in an amount of at least 1 ppm, or ranging from 1 ppm to 500 ppm, or ranging from 5 ppm to 400 ppm, or ranging from 10 ppm to 200 ppm;

(h) dicarboxyanthraquinone isomers in an amount of at least 0.1 ppm, or ranging from 0.1 ppm to 5 ppm, or ranging from 0.2 ppm to 4 ppm, or ranging from 0.3 ppm to 3 ppm;

wherein the compound or compounds selected in (4) are different than the compound or compounds selected in (3).

II. In an embodiment of the invention, the dried carboxylic acid composition 280 comprises:

(1) isophthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 3-carboxybenzaldehyde (3-CBA) in an amount ranging from 1 ppm to 1000 ppm, or ranging from 1 ppm to 500 ppm, or ranging from 1 ppm to 250 ppm, or ranging from 1 ppm to 125 ppm; or (b) m-toluic acid (m-TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
(1) 3-carboxybenzaldehyde (3-CBA) in an amount ranging from 1 ppm to 1000 ppm, or ranging from 1 ppm to 500 ppm, or ranging from 1 ppm to 250 ppm or ranging from 1 ppm to 125 ppm;
(2) m-toluic acid (m-TA) in an amount ranging from 1 ppm to 500 ppm, or ranging from 1 ppm to 250 ppm, or ranging from 1 ppm to 125 ppm;
wherein the total concentration of 3-CBA and m-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least two, or at least three, or at least four, or at least five, or at least six, or all of the following:

(a) terephthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

(c) 3,3'-dicarboxybiphenyl in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

(d) phthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm, or ranging from 20 ppm, 50 ppm, 100 ppm to 500 ppm, or 750 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 750 ppm, or 1000 ppm to 2000 ppm, or 0.5 wt %, or 1 wt %, or 2 wt %, or 3 wt %, or 5 wt %, or 10 wt %, or 25 wt %, or 49 wt %;

(e) 3-hydroxybenzoic acid ranging from 3 ppm to 200 ppm, or ranging from 5 ppm to 175 ppm, or ranging from 20 ppm to 150 ppm, or ranging from 3 ppm, or 5 ppm or 20 ppm to 150 ppm, or 175 ppm, or 200 ppm, or 500 ppm, or 1000 ppm;

(f) 3-hydroxymethylbenzoic acid in an amount of at least 40 ppm, or at least 80 ppm, or at least 100 ppm, or ranging from 40 ppm to 200 ppm, or ranging from 80 ppm to 180, or ranging from 100 ppm to 160 ppm, or ranging from 40 ppm, or 80 ppm, or 100 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %;

(g) benzoic acid ranging from 60 ppm to 500 ppm, or ranging from 75 ppm to 400 ppm, or ranging from 100 ppm to 300 ppm, or ranging from 60 ppm, or 75 ppm, or 100 ppm to 300 ppm, or 500 ppm, or 1000 ppm.

III. In an embodiment of the invention, the dried carboxylic acid composition 280 comprises:

(1) isophthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 3-carboxybenzaldehyde (3-CBA) in an amount ranging from 1 ppm to 1000 ppm, or ranging from 1 ppm to 500 ppm, or ranging from 1 ppm to 250 ppm, or ranging from 1 ppm to 125 ppm; or (b) m-toluic acid (m-TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
(1) 3-carboxybenzaldehyde (3-CBA) in an amount ranging from 1 ppm to 1000 ppm, or ranging from 1 ppm to 500 ppm, or ranging from 1 ppm to 250 ppm or ranging from 1 ppm to 125 ppm;
(2) m-toluic acid (m-TA) in an amount ranging from 1 ppm to 500 ppm, or ranging from 1 ppm to 250 ppm, or ranging from 1 ppm to 125 ppm;

wherein the total concentration of 3-CBA and m-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least two, or at least three, or at least four, or all of the following:

(a) terephthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

(c) 3,3'-dicarboxybiphenyl in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

(d) phthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm, or ranging from 20 ppm, 50 ppm, 100 ppm to 500 ppm, or 750 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 750 ppm, or 1000 ppm to 2000 ppm, or 0.5 wt %, or 1 wt %, or 2 wt %, or 3 wt %, or 5 wt %, or 10 wt %, or 25 wt %, or 49 wt %;

(e) benzoic acid ranging from 60 ppm to 500 ppm, or ranging from 75 ppm to 400 ppm, or ranging from 100 ppm to 300 ppm, or ranging from 60 ppm, or 75 ppm, or 100 ppm to 300 ppm, or 500 ppm, or 1000 ppm.

IV. In an embodiment of the invention, the dried carboxylic acid composition 280 comprises:

(1) isophthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 3-carboxybenzaldehyde (3-CBA) in an amount ranging from 1 ppm to 1000 ppm, or ranging from 1 ppm to 500 ppm, or ranging from 1 ppm to 250 ppm, or ranging from 1 ppm to 125 ppm; or (b) m-toluic acid (m-TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:

(1) 3-carboxybenzaldehyde (3-CBA) in an amount ranging from 1 ppm to 1000 ppm, or ranging from 1 ppm to 500 ppm, or ranging from 1 ppm to 250 ppm or ranging from 1 ppm to 125 ppm;

(2) m-toluic acid (m-TA) in an amount ranging from 1 ppm to 500 ppm, or ranging from 1 ppm to 250 ppm, or ranging from 1 ppm to 125 ppm;

wherein the total concentration of 3-CBA and m-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least two, or at least three, or all of the following:

(a) terephthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt % or less than 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

(c) 3,3'-dicarboxybiphenyl in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

(d) phthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm, or ranging from 20 ppm, 50 ppm, 100 ppm to 500 ppm, or 750 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 750 ppm, or 1000 ppm to 2000 ppm, or 0.5 wt %, or 1 wt %, or 2 wt %, or 3 wt %, or 5 wt %, or 10 wt %, or 25 wt %, or 49 wt %;

V. In an embodiment of the invention, the dried carboxylic acid composition 280 comprises:

(1) isophthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 3-carboxybenzaldehyde (3-CBA) in an amount ranging from 1 ppm to 1000 ppm, or ranging from 1 ppm to 500 ppm, or ranging from 1 ppm to 250 ppm, or ranging from 1 ppm to 125 ppm; or (b) m-toluic acid (m-TA) in an amount ranging from 1 ppm to 1000 ppm, or ranging from 1 ppm to 500 ppm, or ranging from 1 ppm to 250 ppm, or ranging from 1 ppm to 125 ppm; or

43

(c) both of the following:
(1) 3-carboxybenzaldehyde (3-CBA) in an amount ranging from 1 ppm to 1000 ppm, or ranging from 1 ppm to 500 ppm, or ranging from 1 ppm to 250 ppm or ranging from 1 ppm to 125 ppm;
(2) m-toluic acid (m-TA) in an amount ranging from 1 ppm to 500 ppm, or ranging from 1 ppm to 250 ppm, or ranging from 1 ppm to 125 ppm;
wherein the total concentration of 3-CBA and m-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least two or all of the following:
(a) terephthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;
(b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;
(c) 3,3'-dicarboxybiphenyl in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

VI. In an embodiment of the invention, the dried carboxylic acid composition 280 comprises:

(1) isophthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 3-carboxybenzaldehyde (3-CBA) in an amount ranging from 1 ppm to 1000 ppm, or ranging from 1 ppm to 500 ppm, or ranging from 1 ppm to 250 ppm, or ranging from 1 ppm to 125 ppm; or
(b) m-toluic acid (m-TA) in an amount ranging from 1 ppm to 1000 ppm, or ranging from 1 ppm to 500 ppm, or ranging from 1 ppm to 250 ppm, or ranging from 1 ppm to 125 ppm; or
(c) both of the following:
(1) 3-carboxybenzaldehyde (3-CBA) in an amount ranging from 1 ppm to 1000 ppm, or ranging from 1 ppm to 500 ppm, or ranging from 1 ppm to 250 ppm or ranging from 1 ppm to 125 ppm;
(2) m-toluic acid (m-TA) in an amount ranging from 1 ppm to 500 ppm, or ranging from 1 ppm to 250 ppm, or ranging from 1 ppm to 125 ppm;

44 wherein the total concentration of 3-CBA and m-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) both of the following:
(a) terephthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt % or less than 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;
(b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

VII. In an embodiment of the invention, the dried carboxylic acid composition 280 comprises:

(1) isophthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 3-carboxybenzaldehyde (3-CBA) in an amount ranging from 1 ppm to 1000 ppm, or ranging from 1 ppm to 500 ppm, or ranging from 1 ppm to 250 ppm, or ranging from 1 ppm to 125 ppm; or
(b) m-toluic acid (m-TA) in an amount ranging from 1 ppm to 1000 ppm, or ranging from 1 ppm to 500 ppm, or ranging from 1 ppm to 250 ppm, or ranging from 1 ppm to 125 ppm; or
(c) both of the following:
(1) 3-carboxybenzaldehyde (3-CBA) in an amount ranging from 1 ppm to 1000 ppm, or ranging from 1 ppm to 500 ppm, or ranging from 1 ppm to 250 ppm or ranging from 1 ppm to 125 ppm;
(2) m-toluic acid (m-TA) in an amount ranging from 1 ppm to 500 ppm, or ranging from 1 ppm to 250 ppm, or ranging from 1 ppm to 125 ppm;
wherein the total concentration of 3-CBA and m-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) both of the following:
(a) terephthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) 3,3'-dicarboxybiphenyl in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

VII. In an embodiment of the invention, the dried carboxylic acid composition 280 comprises:

(1) isophthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 3-carboxybenzaldehyde (3-CBA) in an amount ranging from 1 ppm to 1000 ppm, or ranging from 1 ppm to 500 ppm, or ranging from 1 ppm to 250 ppm, or ranging from 1 ppm to 125 ppm; or (b) m-toluic acid (m-TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:

(1) 3-carboxybenzaldehyde (3-CBA) in an amount ranging from 1 ppm to 1000 ppm, or ranging from 1 ppm to 500 ppm, or ranging from 1 ppm to 250 ppm or ranging from 1 ppm to 125 ppm;

(2) m-toluic acid (m-TA) in an amount ranging from 1 ppm to 500 ppm, or ranging from 1 ppm to 250 ppm, or ranging from 1 ppm to 125 ppm;

wherein the total concentration of 3-CBA and m-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) both of the following:

(a) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

(b) 3,3'-dicarboxybiphenyl in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

IX. In another embodiment of the invention, the dried carboxylic acid composition 280 comprises:

(1) isophthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight; and (2) 3-carboxybenzaldehyde (3-CBA) in an amount ranging from 1 ppm to 500 ppm, and (3) all of the following:

(a) terephthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) benzene-tricarboxylic acid isomers ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

(c) 3,3'-dicarboxybiphenyl in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

Terephthalic Acid Compositions

I. In an embodiment of the invention, the dried carboxylic acid composition 280 comprises:

(1) terephthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 4-carboxybenzaldehyde (4-CBA) in an amount ranging from 1 ppm to 1000 ppm, or ranging from 1 ppm to 500 ppm, or ranging from 1 ppm to 250 ppm, or ranging from 1 ppm to 125 ppm; or (b) p-toluic acid (p-TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:

(1) 4-carboxybenzaldehyde (4-CBA) in an amount ranging from 1 ppm to 1000 ppm, or ranging from 1 ppm to 500 ppm, or ranging from 1 ppm to 250 ppm or ranging from 1 ppm to 125 ppm;

(2) p-toluic acid (p-TA) in an amount ranging from 1 ppm to 500 ppm, or ranging from 1 ppm to 250 ppm, or ranging from 1 ppm to 125 ppm;

wherein the total concentration of 4-CBA and p-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least one, or at least two, or at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or all of the following:

(a) isophthalic acid in an amount of at least 50 ppm, or ranging from 50 ppm to 2000 ppm, or ranging from 75 ppm to 1500 ppm, or ranging from 100 ppm to 1000 ppm, or ranging from 150 ppm to 500 ppm;

(b) phthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm;

(c) trimellitic acid in an amount of at least 140 ppm, or ranging from 140 ppm to 1000 ppm, or ranging from 175 ppm to 750 ppm, or ranging from 200 ppm to 500 ppm;

(d) benzoic acid in an amount of at least 50 ppm, or at least 75 ppm, or at least 100 ppm; or ranging from 50 ppm to 500 ppm, or ranging from 75 ppm to 400 ppm, or ranging from 100 ppm to 300 ppm;

(e) 4-hydroxybenzoic acid in an amount of at least 3 ppm, at least 5 ppm, or at least 20 ppm, or ranging from 3 ppm to 200 ppm, or ranging from 5 ppm to 175 ppm, or ranging from 20 ppm to 150 ppm;

(f) 4-hydroxymethylbenzoic acid in an amount of at least 40 ppm, or at least 80 ppm, or at least 100 ppm, or ranging from 40 ppm to 200 ppm, or ranging from 80 ppm to 180, or ranging from 100 ppm to 160 ppm;

(g) 4,4'-dicarboxybiphenyl in an amount ranging from 20 ppm to 150 ppm, or ranging from 25 ppm to 100 ppm, or ranging from 25 ppm to 75 ppm;

(h) 2,6-dicarboxyanthraquinone in an amount less than 1 ppm, or less than 0.5 ppm, or less than 0.4 ppm, or less than 0.35 ppm;

(i) 4,4'-dicarboxystilbene in an amount greater than 7 ppm; or greater than 10 ppm;

(j) 2,5,4'-tricarboxybiphenyl in an amount ranging from 8 ppm to 100 ppm, or ranging from 9 ppm to 50 ppm, or ranging from 10 ppm to 25 ppm;

(k) 2,5,4'-tricarboxybenzophenone in an amount ranging from 5 ppm to 100 ppm, or ranging from 6 ppm to 75 ppm, or ranging from 7 ppm to 60 ppm;

(l) 4,4'-dicarboxybenzophenone in an amount ranging from 10 ppm to 150 ppm, or ranging from 12 ppm to 100 ppm, or ranging from 15 ppm to 75 ppm;

(m) 4,4'-dicarboxybenzil in an amount ranging from 1 ppm to 30 ppm, or ranging from 2 ppm to 20 ppm, or ranging from 3 ppm to 10 ppm;

(n) form-acet-hydroxybenzoic acid in an amount ranging from 1 ppm to 20 ppm, or ranging from 2 ppm to 15 ppm, or ranging from 3 ppm to 10 ppm;

(o) acet-hydroxymethylbenzoic acid in an amount ranging from 1 ppm to 30 ppm, or ranging from 2 ppm to 20 ppm, or ranging from 3 ppm to 15 ppm;

(p) a-bromo-p-toluic acid in an amount ranging from 1 ppm to 100 ppm, or ranging from 2 ppm to 50 ppm, or ranging from 5 ppm to 25 ppm;

(q) bromo-benzoic acid in an amount ranging from 5 ppm to 50 ppm, or ranging from 10 ppm to 40 ppm, or ranging from 15 ppm to 35 ppm;

(r) bromo-acetic acid in an amount ranging from 1 ppm to 10 ppm;

(s) p-tolualdehye in an amount ranging from 7 ppm to 50 ppm, or ranging from 8 ppm to 25 ppm, or ranging from 9 ppm to 20 ppm;

(t) terephthaldehyde in an amount ranging from 0.25 ppm to 10 ppm, or ranging from 0.5 ppm to-5 ppm, or ranging from 0.75 ppm to 2 ppm; and optionally, (4) at least one, or at least two, or at least three, or at least four, or at least five or at least six, or at least seven, or all of the following:

(a) isophthalic acid in an amount of at least 1 ppm, or ranging from 1 ppm to 5000 ppm, or ranging from 5 ppm to 2500 ppm, or ranging from 10 ppm to 2000 ppm, or ranging from 15 ppm to 1000 ppm, or ranging from 20 ppm to 500 ppm;

(b) phthalic acid in an amount of at least 1 ppm, or ranging from 1 ppm to 3000 ppm, or ranging from 2 ppm to 2000 ppm, or ranging from 3 ppm to 1000 ppm, or ranging from 4 ppm to 500 ppm;

(c) trimellitic acid in an amount of at least 1 ppm, or ranging from 1 ppm to 3000 ppm, or ranging from 5 ppm to 2000 ppm, or ranging from 10 ppm to 1000 ppm, or ranging from 20 ppm to 500 ppm;

(d) benzoic acid in an amount of at least 1 ppm, or ranging from 1 ppm to 3000 ppm, or ranging from 5 ppm to 2000 ppm, or ranging from 10 ppm to 1000 ppm, or ranging from 20 ppm to 500 ppm;

(e) 4-hydroxybenzoic acid in an amount of at least 1 ppm, or ranging from 1 ppm to 500 ppm, or ranging from 5 ppm to 400 ppm, or ranging from 10 ppm to 200 ppm;

(f) 4-hydroxymethylbenzoic acid in an amount of at least 1 ppm, or ranging from 1 ppm to 500 ppm, or ranging from 5 ppm to 400 ppm, or ranging from 10 ppm to 200 ppm;

(g) 4,4'-dicarboxybiphenyl in an amount of at least 1 ppm, or ranging from 1 ppm to 500 ppm, or ranging from 5 ppm to 400 ppm, or ranging from 10 ppm to 200 ppm;

(h) 2,6-dicarboxyanthraquinone in an amount of at least 0.1 ppm, or ranging from 0.1 ppm to 5 ppm, or ranging from 0.2 ppm to 4 ppm, or ranging from 0.3 ppm to 3 ppm;

wherein the compound or compounds selected in (4) are different than the compound or compounds selected in (3).

II. In an embodiment of the invention, the dried carboxylic acid composition 280 comprises:

(1) terephthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 4-carboxybenzaldehyde (4-CBA) in an amount ranging from 1 ppm to 1000 ppm, or ranging from 1 ppm to 500 ppm, or ranging from 1 ppm to 250 ppm, or ranging from 1 ppm to 125 ppm; or (b) p-toluic acid (p-TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:

(1) 4-carboxybenzaldehyde (4-CBA) in an amount ranging from 1 ppm to 1000 ppm, or ranging from 1 ppm to 500 ppm, or ranging from 1 ppm to 250 ppm or ranging from 1 ppm to 125 ppm;

(2) p-toluic acid (p-TA) in an amount ranging from 1 ppm to 500 ppm, or ranging from 1 ppm to 250 ppm, or ranging from 1 ppm to 125 ppm;

wherein the total concentration of 4-CBA and p-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least two, or at least three, or at least four, or at least five, or at least six, or all of the following:

(a) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) trimellitic acid ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

(c) 4,4'-dicarboxybiphenyl in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

(d) phthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm, or ranging from 20 ppm, 50 ppm, 100 ppm to 500 ppm, or 750 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 750 ppm, or 1000 ppm to 2000 ppm, or 0.5 wt %, or 1 wt %, or 2 wt %, or 3 wt %, or 5 wt %, or 10 wt %, or 25 wt %, or 49 wt %;

(e) 4-hydroxybenzoic acid ranging from 3 ppm to 200 ppm, or ranging from 5 ppm to 175 ppm, or ranging from 20 ppm to 150 ppm, or ranging from 3 ppm, or 5 ppm or 20 ppm to 150 ppm, or 175 ppm, or 200 ppm, or 500 ppm, or 1000 ppm;

(f) 4-hydroxymethylbenzoic acid in an amount of at least 40 ppm, or at least 80 ppm, or at least 100 ppm, or ranging from 40 ppm to 200 ppm, or ranging from 80 ppm to 180, or ranging from 100 ppm to 160 ppm, or ranging from 40 ppm, or 80 ppm, or 100 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %;

(g) benzoic acid ranging from 60 ppm to 500 ppm, or ranging from 75 ppm to 400 ppm, or ranging from 100 ppm to 300 ppm, or ranging from 60 ppm, or 75 ppm, or 100 ppm to 300 ppm, or 500 ppm, or 1000 ppm.

III. In an embodiment of the invention, the dried carboxylic acid composition 280 comprises:

(1) terephthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 4-carboxybenzaldehyde (4-CBA) in an amount ranging from 1 ppm to 1000 ppm, or ranging from 1 ppm to 500 ppm, or ranging from 1 ppm to 250 ppm, or ranging from 1 ppm to 125 ppm; or (b) p-toluic acid (p-TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:

(1) 4-carboxybenzaldehyde (4-CBA) in an amount ranging from 1 ppm to 1000 ppm, or ranging from 1 ppm to 500 ppm, or ranging from 1 ppm to 250 ppm or ranging from 1 ppm to 125 ppm;

(2) p-toluic acid (p-TA) in an amount ranging from 1 ppm to 500 ppm, or ranging from 1 ppm to 250 ppm, or ranging from 1 ppm to 125 ppm;

wherein the total concentration of 4-CBA and p-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least two, or at least three, or at least four, or all of the following:

(a) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) trimellitic acid ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

(c) 4,4'-dicarboxybiphenyl in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

(d) phthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm, or ranging from 20 ppm, 50 ppm, 100 ppm to 500 ppm, or 750 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 750 ppm, or 1000 ppm to 2000 ppm, or 0.5 wt %, or 1 wt %, or 2 wt %, or 3 wt %, or 5 wt %, or 10 wt %, or 25 wt %, or 49 wt %;

(e) benzoic acid ranging from 60 ppm to 500 ppm, or ranging from 75 ppm to 400 ppm, or ranging from 100 ppm to 300 ppm, or ranging from 60 ppm, or 75 ppm, or 100 ppm to 300 ppm, or 500 ppm, or 1000 ppm.

IV. In an embodiment of the invention, the dried carboxylic acid composition 280 comprises:

(1) terephthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 4-carboxybenzaldehyde (4-CBA) in an amount ranging from 1 ppm to 1000 ppm, or ranging from 1 ppm to 500 ppm, or ranging from 1 ppm to 250 ppm, or ranging from 1 ppm to 125 ppm; or (b) p-toluic acid (p-TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:

(1) 4-carboxybenzaldehyde (4-CBA) in an amount ranging from 1 ppm to 1000 ppm, or ranging from 1 ppm to 500 ppm, or ranging from 1 ppm to 250 ppm or ranging from 1 ppm to 125 ppm;

(2) p-toluic acid (p-TA) in an amount ranging from 1 ppm to 500 ppm, or ranging from 1 ppm to 250 ppm, or ranging from 1 ppm to 125 ppm;

wherein the total concentration of 4-CBA and p-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least two, or at least three, or all of the following:

(a) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) trimellitic acid ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

(c) 4,4'-dicarboxybiphenyl in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

(d) phthalic acid in an amount of at least 20 ppm, or at least 50 ppm, or at least 100 ppm, or ranging from 20 ppm to 1000 ppm, or ranging from 50 ppm to 750 ppm, or ranging from 100 ppm to 500 ppm, or ranging from 20 ppm, 50 ppm, 100 ppm to 500 ppm, or 750 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 750 ppm, or 1000 ppm to 2000 ppm, or 0.5 wt %, or 1 wt %, or 2 wt %, or 3 wt %, or 5 wt %, or 10 wt %, or 25 wt %, or 49 wt %;

V. In an embodiment of the invention, the dried carboxylic acid composition 280 comprises:

(1) terephthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 4-carboxybenzaldehyde (4-CBA) in an amount ranging from 1 ppm to 1000 ppm, or ranging from 1 ppm to 500 ppm, or ranging from 1 ppm to 250 ppm, or ranging from 1 ppm to 125 ppm; or (b) p-toluic acid (p-TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:

(1) 4-carboxybenzaldehyde (4-CBA) in an amount ranging from 1 ppm to 1000 ppm, or ranging from 1 ppm to 500 ppm, or ranging from 1 ppm to 250 ppm or ranging from 1 ppm to 125 ppm;

(2) p-toluic acid (p-TA) in an amount ranging from 1 ppm to 500 ppm, or ranging from 1 ppm to 250 ppm, or ranging from 1 ppm to 125 ppm;

wherein the total concentration of 4-CBA and p-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) at least two or all of the following:

(a) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) trimellitic acid ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

(c) 4,4'-dicarboxybiphenyl in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

VI. In an embodiment of the invention, the dried carboxylic acid composition 280 comprises:

(1) terephthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 4-carboxybenzaldehyde (4-CBA) in an amount ranging from 1 ppm to 1000 ppm, or ranging from 1 ppm to 500 ppm, or ranging from 1 ppm to 250 ppm, or ranging from 1 ppm to 125 ppm; or (b) p-toluic acid (p-TA) in an amount ranging from 1 ppm to 1000 ppm, or ranging from 1 ppm to 500 ppm, or ranging from 1 ppm to 250 ppm, or ranging from 1 ppm to 125 ppm; or (c) both of the following:
(1) 4-carboxybenzaldehyde (4-CBA) in an amount ranging from 1 ppm to 1000 ppm, or ranging from 1 ppm to 500 ppm, or ranging from 1 ppm to 250 ppm or ranging from 1 ppm to 125 ppm;
(2) p-toluic acid (p-TA) in an amount ranging from 1 ppm to 500 ppm, or ranging from 1 ppm to 250 ppm, or ranging from 1 ppm to 125 ppm;
wherein the total concentration of 4-CBA and p-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) both of the following:
(a) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;
(b) trimellitic acid ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

VII. In an embodiment of the invention, the dried carboxylic acid composition 280 comprises:

(1) terephthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 4-carboxybenzaldehyde (4-CBA) in an amount ranging from 1 ppm to 1000 ppm, or ranging from 1 ppm to 500 ppm, or ranging from 1 ppm to 250 ppm, or ranging from 1 ppm to 125 ppm; or
(b) p-toluic acid (p-TA) in an amount ranging from 1 ppm to 1000 ppm, or ranging from 1 ppm to 500 ppm, or ranging from 1 ppm to 250 ppm, or ranging from 1 ppm to 125 ppm; or
(c) both of the following:
(1) 4-carboxybenzaldehyde (4-CBA) in an amount ranging from 1 ppm to 1000 ppm, or ranging from 1 ppm to 500 ppm, or ranging from 1 ppm to 250 ppm or ranging from 1 ppm to 125 ppm;
(2) p-toluic acid (p-TA) in an amount ranging from 1 ppm to 500 ppm, or ranging from 1 ppm to 250 ppm, or ranging from 1 ppm to 125 ppm;
wherein the total concentration of 4-CBA and p-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) both of the following:
(a) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;
(b) 4,4'-dicarboxybiphenyl in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

VIII. In an embodiment of the invention, the dried carboxylic acid composition 280 comprises:

(1) terephthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight;

and (2) (a) 4-carboxybenzaldehyde (4-CBA) in an amount ranging from 1 ppm to 1000 ppm, or ranging from 1 ppm to 500 ppm, or ranging from 1 ppm to 250 ppm, or ranging from 1 ppm to 125 ppm; or
(b) p-toluic acid (p-TA) in an amount ranging from 1 ppm to 1000 ppm, or ranging from 1 ppm to 500 ppm, or ranging from 1 ppm to 250 ppm, or ranging from 1 ppm to 125 ppm; or
(c) both of the following:
(1) 4-carboxybenzaldehyde (4-CBA) in an amount ranging from 1 ppm to 1000 ppm, or ranging from 1 ppm to 500 ppm, or ranging from 1 ppm to 250 ppm or ranging from 1 ppm to 125 ppm;
(2) p-toluic acid (p-TA) in an amount ranging from 1 ppm to 500 ppm, or ranging from 1 ppm to 250 ppm, or ranging from 1 ppm to 125 ppm;
wherein the total concentration of 4-CBA and p-TA ranges from 1 ppm to 2000 ppm, 1 ppm to 1000 ppm, or from 1 ppm to 500 ppm, or from 1 ppm to 250 ppm, or from 1 ppm to 125 ppm;

and (3) both of the following:
(a) trimellitic acid ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;
(b) 4,4'-dicarboxybiphenyl in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

IX. In another embodiment of the invention, the dried carboxylic acid composition 280 comprises:

(1) terephthalic acid in an amount greater than 50 percent by weight, or greater than 60 percent by weight, or greater than 70 percent by weight, or greater than 80 percent by weight, or greater than 90 percent by weight, or greater than 95 percent by weight, or greater than 97 percent, or greater than 98 percent, or greater than 98.5 percent, or greater than 99 percent, or greater than 99.5 percent by weight; and (2) 4-carboxybenzaldehyde (4-CBA) in an amount ranging from 1 ppm to 500 ppm, and (3) all of the following:

(a) isophthalic acid in an amount at least 50 ppm, or ranging from 50 ppm to 2000 ppm, or ranging from 75 ppm to 1500 ppm, or ranging from 100 ppm to 1000 ppm, or ranging from 150 ppm to 500 ppm, or ranging from 50 ppm, or 75 ppm, or 100 ppm, or 150 ppm to 500 ppm, or 1000 ppm, or 2000 ppm, or 0.5 wt %, or 1 wt %, or 2 wt %, or 3 wt %, or 5 wt %, or 10 wt %, or 25 wt %, or 49 wt %, or ranging from 500 ppm, or 1000 ppm to 2000 ppm, or 0.5 wt % or 1 wt %, or 2 wt %, or 3 wt %, or 5 wt %, or 10 wt %, or 25 wt %, or 49 wt %;

(b) trimellitic acid ranging from 140 ppm to 1000 ppm, or ranging from 175 ppm to 750 ppm, or ranging from 200 ppm to 500 ppm, or ranging from 150 ppm, or 175 ppm, or 200 ppm to 500 ppm, or 750 ppm, or 1000 ppm;

(c) 4,4'-dicarboxybiphenyl in an amount ranging from 20 ppm to 150 ppm, or ranging from 25 ppm to 100 ppm, or ranging from 25 ppm to 75 ppm, or ranging from 200 ppm, or 300 ppm, or 500 ppm to 1000 ppm, or 2000 ppm, or 0.5 wt %, or 1 wt %, or 2 wt %, or 3 wt %, or 5 wt %, or 10 wt %, or 25 wt %, or 49 wt %;

In another embodiment of this invention, all the compositions of the dried carboxylic acid composition 280 previously stated further comprise a catalyst composition of less than 1000 ppm, or 500 ppm, or 250 ppm, or 100 ppm. Other ranges are less than 85 ppm, and less than 50 ppm. Yet another range is less than 25 ppm, or less than 15 ppm, or less than 10 ppm or less than 5 ppm. In another embodiment of the invention, the catalyst comprises cobalt and manganese. In another embodiment of the invention, the catalyst comprises cobalt.

All concentrations throughout the disclosure and claims are on a dry solids basis. The physical form of the TPA product can be a dry solid, wet cake, paste, or slurry. For the sake of consistency, any liquid present in the TPA product is ignored when describing its composition. The composition will be expressed as a weight percent or ppmw (part per million by weight) on a dry solids basis which assumes there is no moisture in the product. For example, 500 ppmw of p-toluic acid in a TPA product means there are 500 grams of p-toluic acid for every 1,000,000 grams of non-liquid mass in the product regardless of the actual physical form of the product. All measurements expressed in ppm are ppm by weight. Therefore, ppm is equivalent to ppmw throughout the disclosure.

In another embodiment of this invention, all the compositions previously stated are an average composition over a continuous period during steady state operation. In yet another embodiment of the invention, the compositions previously disclosed are the time average compositions obtained over a 7 day period, or 14 day period, or 30 day period during continuous operation. In another embodiment of the invention, the compositions previously disclosed could include any sample taken from a 1 metric ton lot (1,000 kg) or larger. In another embodiment of the invention, the compositions previously disclosed could include any sample in a shipping container, or a shipping container containing at least 500 kg of the disclosed compositions.

In an embodiment of the invention, the compositions of matter we have specified will be utilized to make PET which could be subsequently used in producing coatings, resins, fibers, film, sheet, containers, or other formed articles.

In an embodiment of the invention, the compositions previously disclosed, can have functionalities in PET polymerization ranging from zero through at least three. Functional groups for polycondensation polymerization of polyesters and copolyesters, as well as polyamides, copolyamides, and other co-polycondensation polymers comprise reactive carboxyl and reactive hydroxyl groups. The following discussion will focus on the impact of various impurities or oxidation by-products on the manufacture and properties of poly (ethylene terephthalate) (PET) as an example.

Zero-functional impurities are either removed via purge processes in PET manufacture or end up as diluting species in the PET. Mono- and tri-functional species affect the rate of polymerization, possibly both in melt-phase and solid-stating, but usually more so in solid-stating due to the difficulty of obtaining high molecular weight especially with monofunctional, chain-terminating species present. Depending on the concentrations, mono- and tri-functional species also can affect the PET product properties via changing the PET polydispersity of molecular weight.

For example, p-toluic acid (p-TA) is an impurity which is monofunctional in PET polymerization with PET process polymerization catalysts. In contrast, 4-carboxybenzaldehyde (4-CBA) is monofunctional when used with an Sb (antimony) catalyst in PET polymerization, but can be di- or tri-functional when used with a Ti (titanium) catalyst in PET polymerization, due to the conversion of the aldehyde group to a hemiacetal or an acetal. Trimellitic acid (1,2,4-benzene tricarboxylic acid, or TMA) is a tri-functional impurity. To a first approximation, mono- and tri-functional impurities have offsetting effects on PET polymerization. That is, increased amounts of mono-functional impurities, such as p-toluic acid, benzoic acid, monocarboxyfluorenones, bromo-benzoic acid, bromo-acetic acid, and 4-CBA (with Sb catalyst), can be compensated for via increased concentration of tri- or greater functional impurities, such as trimellitic acid, 2,5,4'-tricarboxybiphenyl, 2,5,4'-tricarboxybenzophenone, and 4-CBA (with Ti catalyst). Molar concentrations must be used and not weight-based concentrations when comparing the polymerization effects of impurities with functionality other than two, as well as the relative reactivity of reacting groups (primarily carboxyl functionality) when the functionality is greater than one. Fortunately, most of the impurities present in PTA in significant concentrations (more than a few ppmw) are bi-functional and thus have no deleterious effects on PET polymerization due to their functionality and they have no deleterious effects on PET polymer properties due to their low concentration. In particular, assuming an Sb-catalyzed PET polymerization process, then each 1.0 ppmw of TMA will approximately offset approximately 0.60 ppmw benzoic acid (BA), or 0.65 ppmw p-TA, due to differences in molecular weight. If analytical information is known for PTA impurities, i.e. the concentrations of the impurities and their functionalities, then an estimate can be made of the relative overall effect on PET polymerization.

Note that for IPA instead of TPA, the compounds will be 3-hydroxybenzoic acid, 3-hydroxymethylbenzoic acid, 3,3'-dicarboxybiphenyl, dicarboxyanthraquinone isomers, and 3,3'-dicarboxystilbene, etc. Similarly, for carboxylic acids, the compounds will be hydroxybenzoic acid isomers, hydroxymethylbenzoic acid isomers, dicarboxybiphenyl isomers, dicarboxyanthraquinone isomers, and dicarboxystilbene isomers, etc.

In another embodiment of the invention, the previously disclosed carboxylic acid compositions comprising terephthalic or isophthalic acid or any di-functional carboxylic acid would have a total monofunctional compound(s) concentration less than 0.5 mole %, or less than 0.25 mole %, or less than 0.1 mole %, or less than 0.05 mole %, or less than 0.025 mole %, or less than 0.01 mole %, or less than 0.005 mole %.

In another embodiment of the invention, the previously disclosed carboxylic acid compositions comprising terephthalic or isophthalic acid or any di-functional carboxylic acid would have a total monofunctional compound(s) concentration less than 5000 ppm, or less than 2500 ppm, or less than 1000 ppm, or less than 500 ppm, or less than 250 ppm, or less than 100 ppm, or less than 50 ppm.

In another embodiment of the invention, the previously disclosed carboxylic acid compositions comprising terephthalic or isophthalic acid or any di-functional carboxylic acid would have a total tri-functional and greater-than-tri-functional compound(s) concentration less than 0.5 mole %, or less than 0.25 mole %, or less than 0.1 mole %, or less than 0.05 mole %, or less than 0.025 mole %, or less than 0.01 mole %, or less than 0.005 mole %.

In another embodiment of the invention, the previously disclosed carboxylic acid compositions comprising terephthalic or isophthalic acid or any di-functional carboxylic acid would have a total tri-functional and greater-than-tri-functional compound(s) concentration less than 5000 ppm, or less than 2500 ppm, or less than 1000 ppm, or less than 500 ppm, or less than 250 ppm, or less than 100 ppm, or less than 50 ppm.

In another embodiment of the invention, the previously disclosed carboxylic acid compositions comprising terephthalic or isophthalic acid or any di-functional carboxylic acid would have a total zero-functional compound(s) concentration less than 0.5 mole %, or less than 0.25 mole %, or less than 0.1 mole %, or less than 0.05 mole %, or less than 0.025 mole %, or less than 0.01 mole %, or less than 0.005 mole %.

In another embodiment of the invention, the previously disclosed carboxylic acid compositions comprising terephthalic or isophthalic acid or any di-functional carboxylic acid would have a total zero-functional compound(s) concentration less than 5000 ppm, or less than 2500 ppm, or less than 1000 ppm, or less than 500 ppm, or less than 250 ppm, or less than 100 ppm, or less than 50 ppm.

In another embodiment of the invention, the previously disclosed carboxylic acid compositions comprising terephthalic or isophthalic acid or any di-functional carboxylic acid would have an average functionality, not including zero functionality species, of at least 1.995 or greater, or at least 1.996 or greater, or at least 1.997 or greater, or at least 1.998 or greater, or at least 1.999 or greater, or at least 1.9995 or greater, or at least 1.9999 or greater.

In another embodiment of the invention, the previously disclosed carboxylic acid compositions comprising terephthalic or isophthalic acid or any di-functional carboxylic acid would have an average functionality, not including zero functionality species, of between 1.995, or 1.996, or 1.997, or 1.998, or 1.999, or 1.9995, or 1.9999 and 2.0000, or 2.0001, or 2.0005, or 2.001, or 2.002 or 2.003, or 2.004, or 2.005.

In another embodiment of the invention, the previously disclosed carboxylic acid compositions comprising terephthalic or isophthalic acid or any di-functional carboxylic acid would have an average carboxyl functionality, not including species with zero carboxyl functionality, of at least 1.995 or greater, or at least 1.996 or greater, or at least 1.997 or greater, or at least 1.998 or greater, or at least 1.999 or greater, or at least 1.9995 or greater, or at least 1.9999 or greater.

In another embodiment of the invention, the previously disclosed carboxylic acid compositions comprising terephthalic or isophthalic acid or any di-functional carboxylic acid would have an average carboxyl functionality, not including species with zero carboxyl functionality, of between 1.995, or 1.996, or 1.997, or 1.998, or 1.999, or 1.9995, or 1.9999 and 2.0000, or 2.0001, or 2.0005, or 2.001, or 2.002 or 2.003, or 2.004, or 2.005.

Figure 20A:
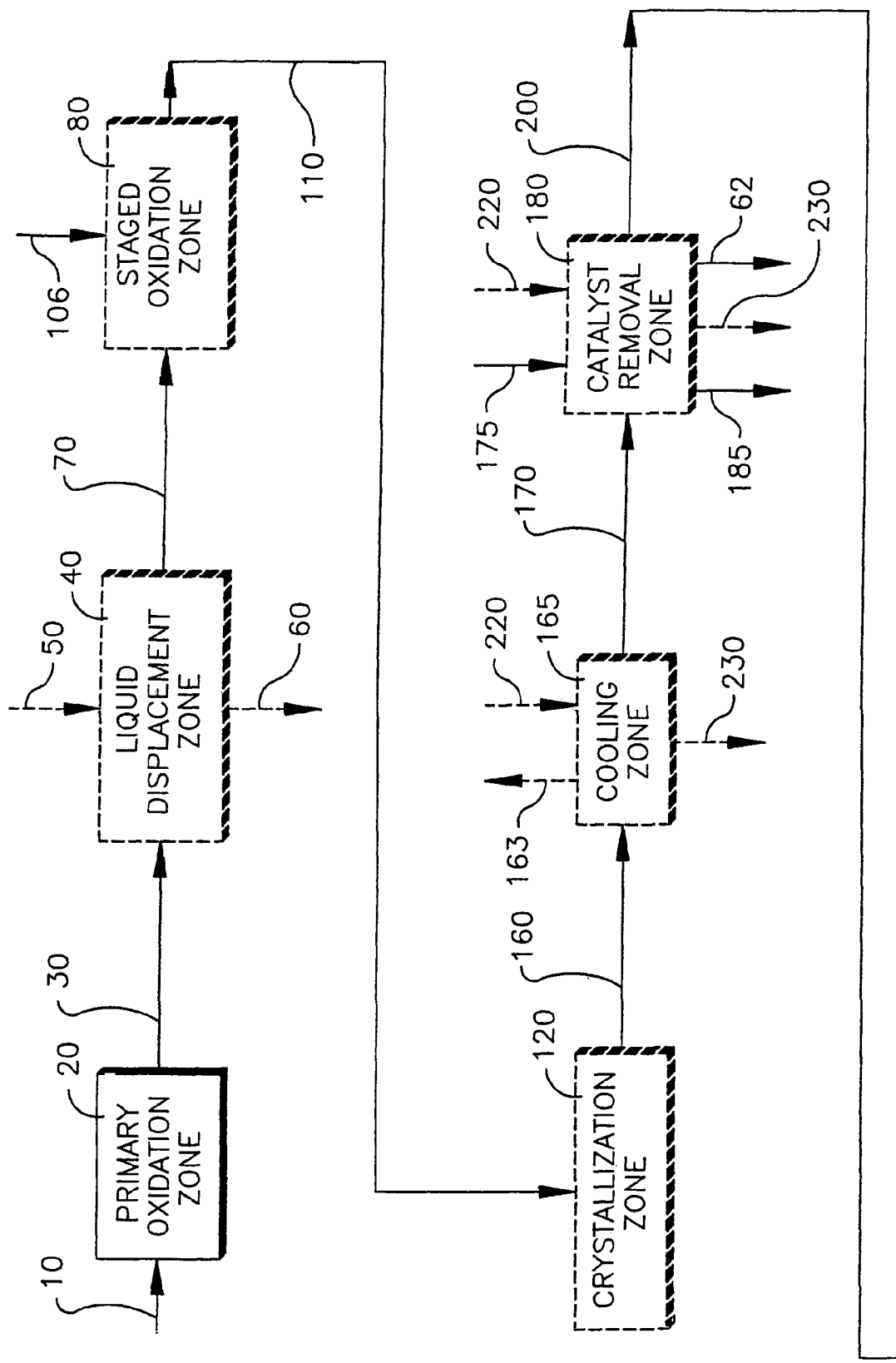
FIGS. 20A & B illustrates an embodiment of the invention wherein the catalyst removal zone 180 is optional, and the enrichment zone 210 is required.
Figure 20B:
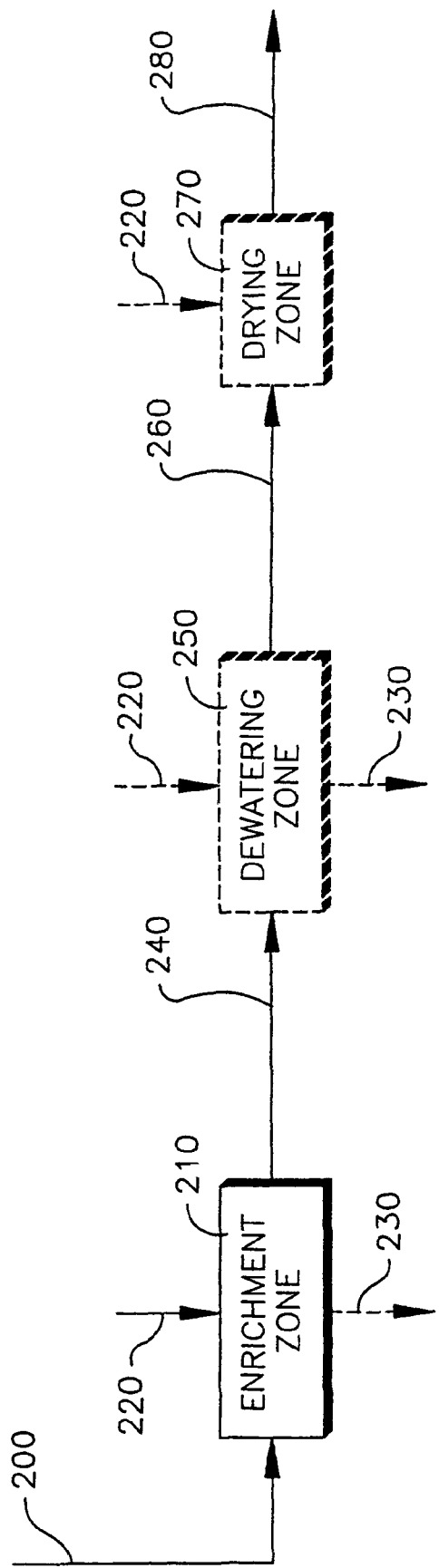

In another embodiment of the invention, a process for producing an enriched composition 240 is provided as shown in FIGS. 20A and 20B. In this embodiment, as shown in FIGS. 20 a&b, the catalyst removal zone 180 is optional and the enrichment zone 210 is required. All of the zones in FIGS. 20A & B have been previously been described in this disclosure. It should be appreciated that the process zones previously described can be utilized in any other logical order to produce the dried carboxylic acid composition 280. It should also be appreciated that when the process zones are reordered that the process conditions may change. It should also be appreciated that the process zones can be used independently.

In another embodiment of this invention, each embodiment can optionally include an additional step comprising decolorizing the carboxylic acid or an esterified carboxylic acid. Preferably the decolorizing is accomplished by hydrogenation. The decolorizing can occur at any location after the primary oxidation zone 20.

The decolorizing of a carboxylic acid slurry or an esterified carboxylic acid can be accomplished by any means known in the art and is not limited to hydrogenation. However, for example in one embodiment of the invention, the decolorizing can be accomplished by reacting a carboxylic acid that has undergone esterification treatment, for example with ethylene glycol, with molecular hydrogen in the presence of a hydrogenation catalyst in a decolorizing reactor zone to produce a decolorized carboxylic acid solution or a decolorized ester product. For the decolorizing reactor zone, there are no special limitations in the form or construction thereof, subject to an arrangement that allows supply of hydrogen to effect intimate contact of the carboxylic acid or ester product with the catalyst in the decolorizing reactor zone. Typically, the hydrogenation catalyst is usually a single Group VIII metal or combination of Group VIII metals. Preferably, the hydrogenation catalyst is selected from a group consisting of palladium, ruthenium, rhodium and combination thereof. The decolorizing reactor zone comprises a hydrogenation reactor that operates at a temperature and pressure sufficient to hydrogenate a portion of the characteristically yellow compounds to colorless derivatives.

Figure 16:
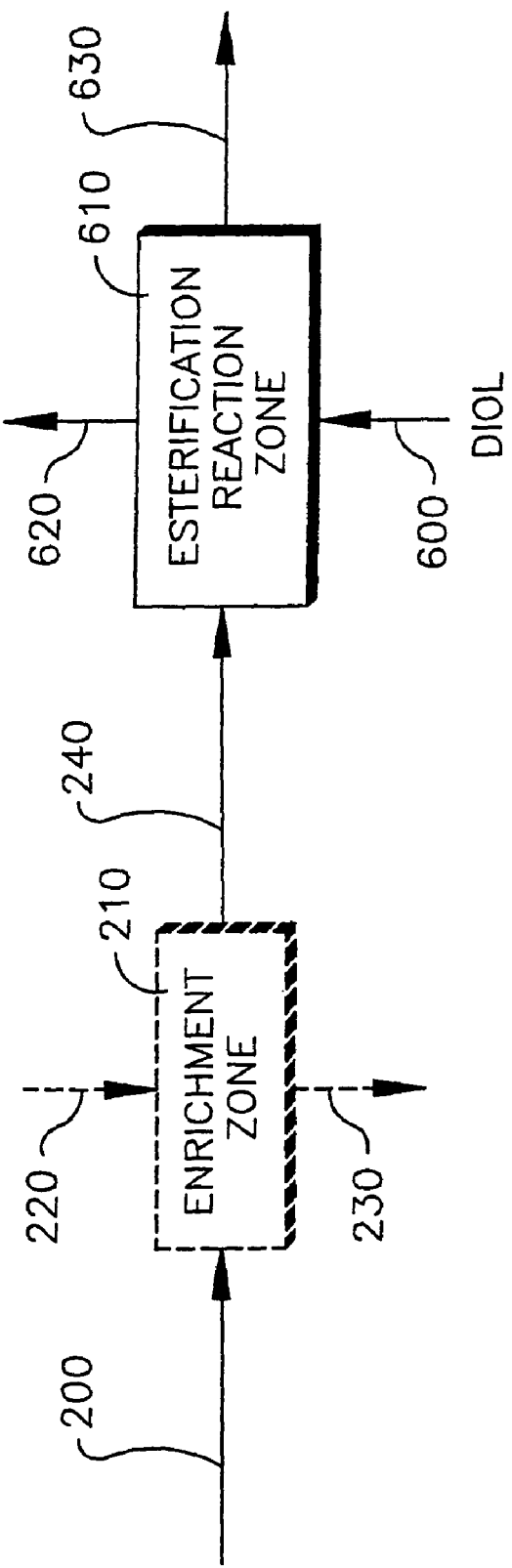
FIG. 16 illustrates an embodiment of the invention wherein an enriched composition 240 is sent directly to an esterification reaction zone 610.

In another embodiment of the invention, instead of utilizing the drying zone as preciously disclosed, the enriched composition 240 can be directly routed to an esterification zone 310 as shown in FIG. 16. In this embodiment, the moisture content in the enriched composition 240 is predominantly water and the weight % of acetic acid in the enriched composition 240 is less than 10%, preferably less than 2%, and most preferably less than 0.1%. "Predominantly" as used herein means greater than 85% of total moisture mass.

Therefore, instead of drying, in an embodiment of the invention, step (i) comprises adding a diol in conduit 600 to the enriched composition 240 in an esterification reactor zone 610 to remove a portion of the moisture via conduit 620 to form a carboxylic acid and diol mixture in the esterification reactor zone 610. The carboxylic acid and diol react to form a hydroxyalkyester stream 630. The hydroxyalkyester stream 630 comprises a hydroxyalky ester compound.

The diol in conduit 600 is introduced in such a manner as to displace the moisture as the dominant slurrying liquid. This can be accomplished by introducing a diol via conduit 600 as a saturated liquid in a temperature range of about 150° C. to about 300° C. Preferably, the diol in conduit 600 is introduced as a saturated or superheated vapor in a temperature range of about 150° C. to about 300° C. in a form with sufficient enthalpy as to evaporate the water to exit via conduit 320. The diol in conduit 600 is selected from the group consisting of ethylene glycol, diethylene glycol, tri-ethylene glycol, 1,3-propanediol, 1,2-propanediol, 1,4-butanediol, 1,3-butanediol, cyclohexanedimethanol, neopentyl glycol, other diols useful in making polyesters and copolyesters, and mixtures thereof. Preferably, the diol in conduit 600 is ethylene glycol. Alternatively, an external heat source can be used to introduce sufficient enthalpy to vaporize the water, which exits via conduit 620. The hydroxalkyl ester stream mixture exits via conduit stream 630.

The esterification reactor zone 610 operates at a temperature of about 240° C. higher. Preferably the esterification reactor zone 610 operates in a temperature range of about 260° C. to about 280° C. The esterification reactor zone 610 operates at a pressure of about 40 psia to about 100 psia so as to effect esterification of the terephthalic acid and diol mixture to produce a hydroxyethyl ester of terephthalic acid.

Figure 17:
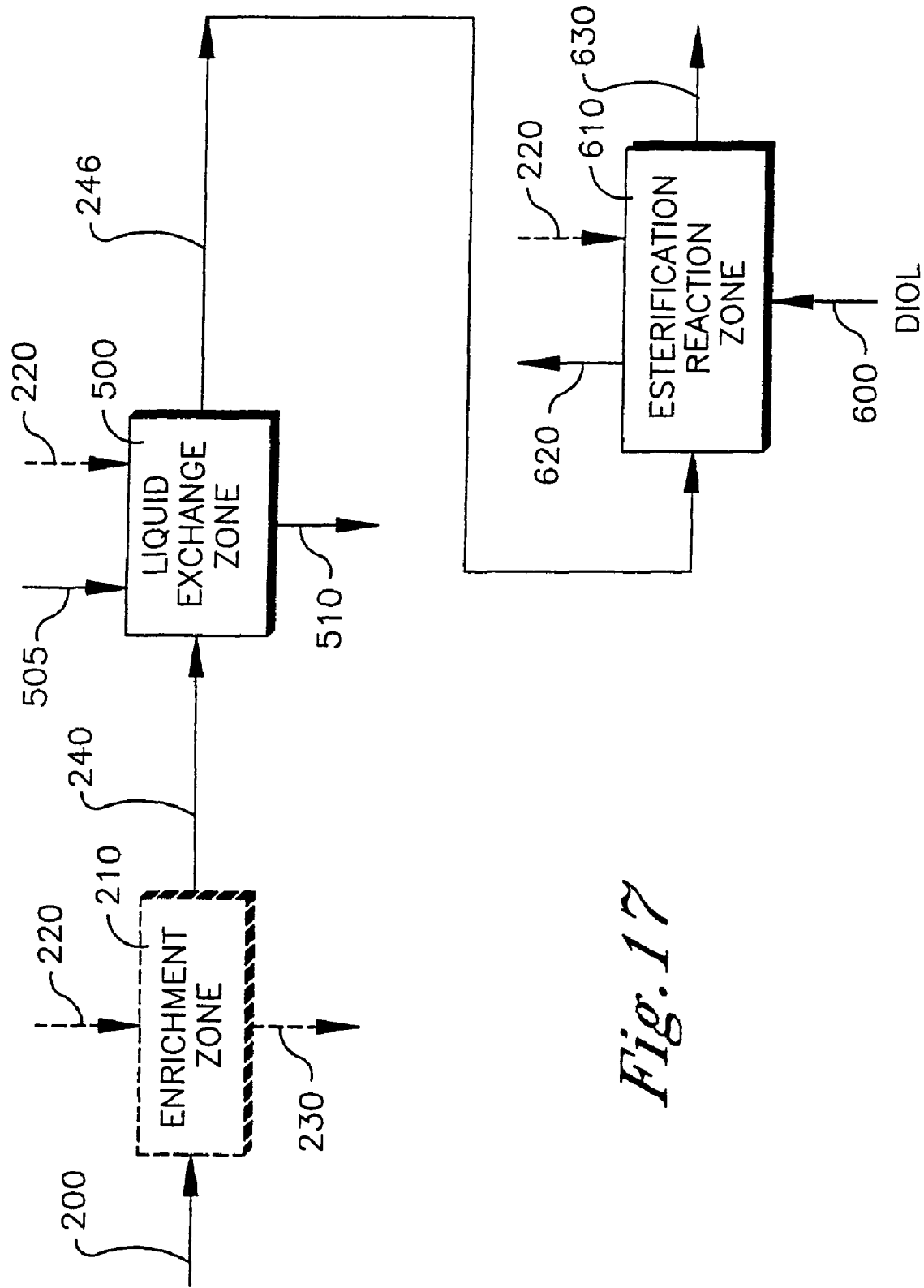
FIG. 17 illustrates an embodiment of the invention wherein a water wet cake composition 246 is sent directly to an esterification reactor zone 610.
Figure 18:
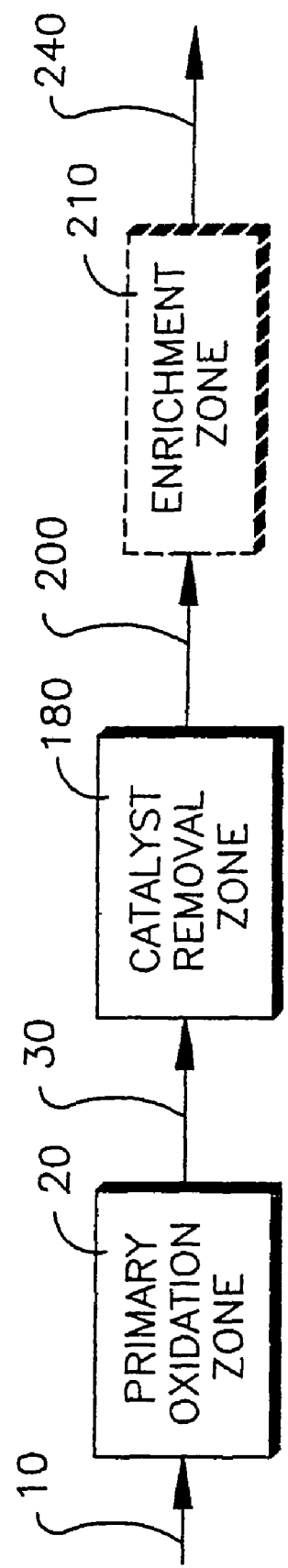
FIG. 18 illustrates an embodiment of the invention where an aromatic feedstock 10 is utilized to produce a post catalyst removal composition 200.
Figure 19:
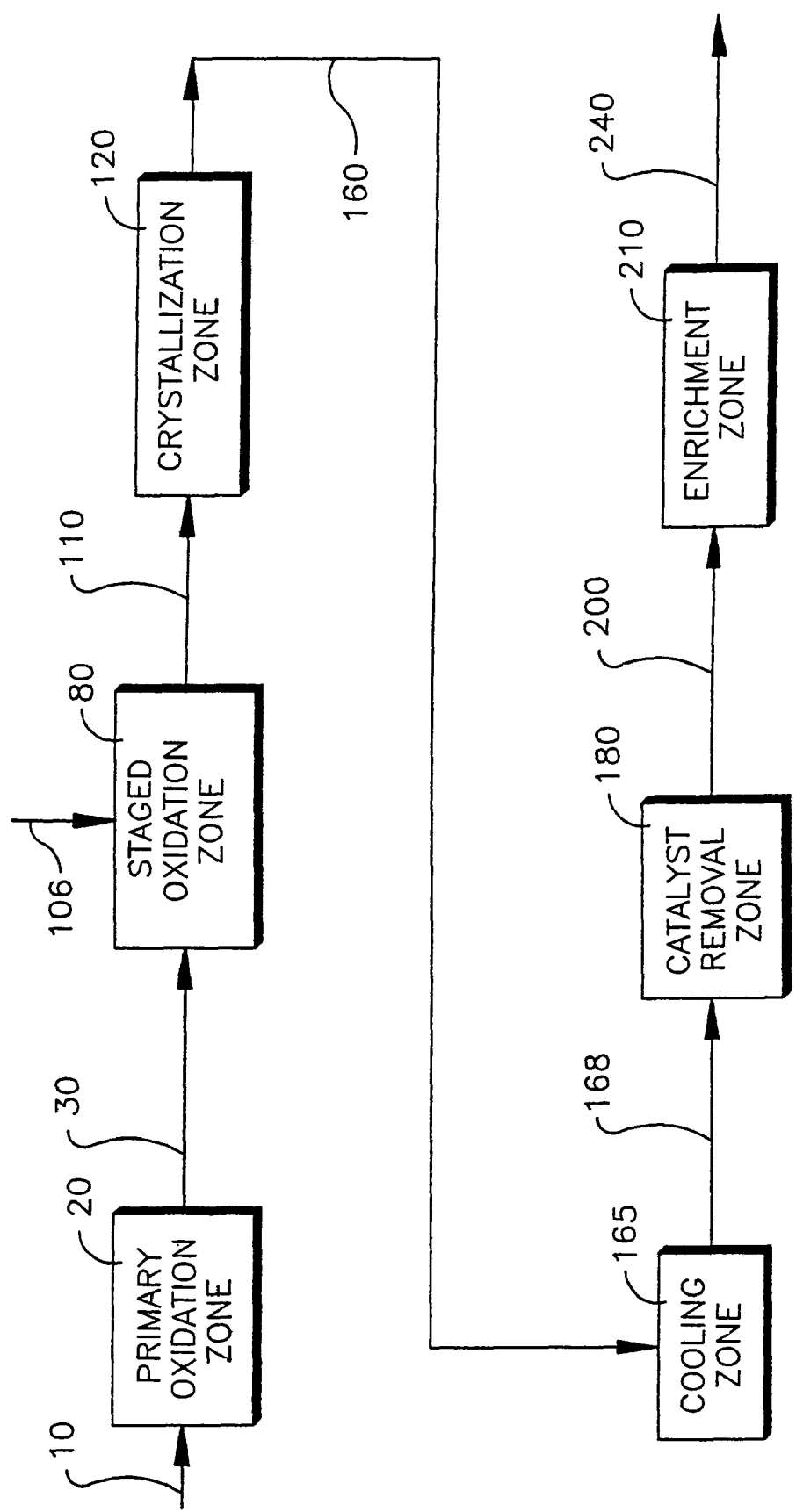
FIG. 19 illustrates an embodiment of the invention wherein an aromatic feedstock 10 is utilized to produce an enriched composition 240.

In another embodiment of the invention, instead of utilizing the drying zone as preciously disclosed, the enriched composition 240 can be directly routed to a liquid exchange zone 500 as shown in FIG. 17. In this embodiment, the moisture content in the enriched composition 240 has a significant amount of solvent. "Significant amount" as used herein means greater than 1%, or greater than 2%, or greater than 5% or greater than 10% or greater than 15%.

The enriched composition 240 is subjected to a wash or "rinsing" with exchange solvent in the liquid exchange zone 500, wherein a portion of the initial solvent is replaced with exchange solvent to form an exchange solvent enriched composition 246. The exchange solvent comprises water, methanol, ethylene glycol, and any diol or monomer compatible with polyester or copolyester manufacturing process. The exchange solvent enriched composition 246, is preferably in the range of 0.5-30% by weight moisture, more preferably in the range of about 1-20% by weight moisture, and most preferably in the range of 1-5% by weight moisture. The residual moisture of the exchange solvent enriched composition 206 could contain less than about 2% by weight solvent, another range is less than 5% or less than 10% by weight, or less than 20%.

In an embodiment of the invention, exchange solvent is introduced into the liquid exchange zone 500. The exchange solvent is preferably introduced on a continuous basis. There are no limitations on the temperature or pressure of the exchange solvent including the use of vaporized water, steam, or a combination of water and steam as wash.

The liquid exchange zone 500 comprises at least one solid liquid separation device. The solid liquid separation device can typically be comprised of, but not limited to, the following types of devices: centrifuges, cyclones, rotary drum filters, belt filters, press filters, etc. The solid liquid separation device can operate within a temperature range of from about 5° C. to 195° C. The liquid exchange zone and the catalyst removal zone can be within the same device, for example in a belt filter. The exchange solvent enriched composition 246 is subsequently sent to an esterification zone 610 which has been previously described.

Examples

An Embodiment of this invention can be further illustrated by the following examples of preferred embodiments thereof, although it will be understood that these examples are included merely for purposes of illustration and are not intended to limit the scope.

PTA Retention Experiments

The objective of this set of experiments was to determine how the retention of IPA in cooled carboxylic acid composition stream 170 varies with wash temperature and wash ratio of wash feed stream 175 in the catalyst removal zone 180. All experiments utilized a bench scale Pannevis vacuum filter apparatus. Cooled carboxylic acid composition stream 170 was prepared by taking a crystallized slurry composition stream 160 slurry at 30 weight percent solids and boiling away solvent until reaching 50% solids. The slurry was then cooled to 30° C. to generate a cooled carboxylic acid composition stream 170 and charged to the vacuum filter, and then washed with a wash feed stream 175. Both the wash ratio and the wash temperature were varied in the experiment. A wash ratio of 1 and 0.5 was used. A wash temperature of 90° C. and 10° C. was used. The wash was 90% acetic acid and 10% water. The time after adding the wash till the dry top of the cake was observed is called the Dry Top Time and was recorded. Samples of the post catalyst removal composition 200 were analyzed for ppm wt IPA.

Experiment 1 (No Wash)

700.10 g of crystallized slurry composition stream 160 were charged to a stainless steel beaker. The slurry was heated until the weight of the slurry was reduced to 420 gms. The slurry was cooled rapidly to 30° C. using wet ice generating a cooled carboxylic acid composition stream 170. The cooled carboxylic acid composition stream 170 was fed to a bench scale Pannevis vacuum filter. After feeding the cooled carboxylic acid composition stream 170 to the vacuum filter 16.5 grams of the cooled carboxylic acid composition stream 170 remained in the steel beaker. The actual mass of the cooled carboxylic acid composition stream 170 to the filter was 403.5 grams, (420 grams-16.5 grams). The weight of the wet cake pre catalyst removal composition stream was 266.38 grams. The % solids of the wet cake was 94.2%. Samples from the wet cake were submitted to analytical for IPA analyses.

Experiment 2 (Wash Ratio 0.5, Wash Temperature 90° C.)

700.04 g of crystallized slurry composition stream 160 was charged to a stainless steel beaker. The slurry was heated until the weight of the slurry was reduced to 420.73 gms. The slurry was cooled rapidly to 30° C. using wet ice generating a cooled carboxylic acid composition Stream 170. The cooled carboxylic acid composition stream 170 was fed to a bench scale Pannevis vacuum filter. After feeding the cooled carboxylic acid composition stream 170 to the vacuum filter 16.5 grams of the cooled carboxylic acid composition stream 170 remained in the stainless steel beaker. The actual mass of the cooled carboxylic acid composition stream 170 to the filter was 405.94 grams, (420.73 grams-14.79 grams). The filter cake was washed with 100.18 gms of 90° C. acetic acid/water solution wash fed stream 175. The weight of the wet cake post catalyst removal composition stream 200 was 232.83 grams. The % solids of the wet cake post catalyst composition stream 200 was 99.2%. Samples from the wet cake were submitted to analytical for IPA analyses.

Experiment 3 (Wash Ratio 1.0, Wash Temperature 90° C.)

700.39 g of crystallized slurry composition stream 160 were charged to a stainless steel beaker. The slurry was heated until the weight of the slurry was reduced to 420.25 gms. The slurry was cooled rapidly to 30° C. using wet ice generating a cooled carboxylic acid composition Stream 170. The cooled carboxylic acid composition stream 170 was fed to a bench scale Pannevis vacuum filter. After feeding stream 170 to the vacuum filter, 12.69 grams of Stream 170 remained in the stainless steel beaker. The actual mass of stream 170 to the filter was 407.56 grams, (420.25 grams-12.69 grams). The filter cake was washed with 200.14 gms of 90 C acetic acid/ water solution wash fed stream 175. The weight of the wet cake post catalyst removal composition stream 200 was 226.61 grams. The % solids of the wet cake post catalyst composition stream 200 was 95.4%. Samples from the post catalyst removal composition 200 were submitted to analytical for IPA analyses.

Experiment 4 (Wash Ratio 0.5, Wash Temperature 10° C.)

700.3 g of crystallized slurry composition stream 160 were charged to a stainless steel beaker. The slurry was heated until the weight of the slurry was reduced to 420.3 gms. The slurry was cooled rapidly to 30° C. using wet ice generating a cooled carboxylic acid composition stream 170. Stream 170 was fed to a bench scale Pannevis vacuum filter. After feeding stream 170 to the vacuum filter, 15.29 grams of stream 170 remained in the stainless steel beaker. The actual mass of Stream 170 to the filter was 405.01 grams, (420.3 grams-15.29 grams). The filter cake was washed with 100.37 grams of 10° C. acetic acid/water solution wash fed stream 175. The weight of the wet cake post catalyst removal composition stream 200 was 248.84 grams. The % solids of the wet cake post catalyst composition stream 200 was 90.75%. Samples from the post catalyst removal composition were submitted to analytical for IPA analyses.

Experiment 5 (Wash Ratio 1.0, Wash Temperature 10° C.)

700.44 g of crystallized slurry composition stream 160 were charged to a stainless steel beaker. The slurry was heated until the weight of the slurry was reduced to 420.35 gms. The slurry was cooled rapidly to 30° C. using wet ice generating a cooled carboxylic acid composition Stream 170. The cooled carboxylic acid composition stream 170 was fed to a bench scale Pannevis vacuum filter. After feeding stream 170 to the vacuum filter, 9.3 grams of stream 170 remained in the stainless steel beaker. The actual mass of stream 170 to the filter was 411.05 grams, (420.35 grams-9.3 grams). The filter cake was washed with 200.06 grams of 10° C. acetic acid/water solution wash fed stream 175. The weight of the wet cake post catalyst removal composition stream 200 was 225.06 grams. The % solids of the wet cake post catalyst composition Stream 200 was 89.55%. Samples from the post catalyst removal composition 200 were submitted to analytical for IPA analyses.

| Results | | | | |
|---|---|---|---|---|
| Experiment | Wash Temp. | Wash Ratio | IPA (ppmw) | Dry Top (sec) |
| 1 | no wash | no wash | 3249 | Na |
| 2 | 90° C. | 0.5 | 146 | 5 |
| 3 | 90° C. | 1.0 | 25 | 10 |
| 4 | 10° C. | 0.5 | 39 | 9 |
| 5 | 10° C. | 1.0 | 20 | 17 |

It is clear that retention of IPA varies with wash temperature and wash ratio allowing the control of the IPA content in the post catalyst removal composition stream 200. The range of IPA content in stream 200 in the experiments above varied from 146 ppm to 20 ppm depending upon the amount and temperature of wash. Retention of select oxidation by-products can be controlled by the temperature, composition, and amount of wash feed Stream 175 applied in the catalyst removal zone 180. This data illustrates oxidation by-product retention in a catalyst removal zone utilizing IPA as an example. IPA is considered representative such that other oxidation by-products can exhibit similar retention behavior under specific wash temperature and wash ratio combinations.

PTA Enrichment with Isophthalic Acid

The objective of this experiment was to demonstrate terephthalic acid enrichment.

In experiment 1, cooled carboxylic acid composition stream 170 slurry was charged to a bench scale Pannevis vacuum filter apparatus and the resulting post catalyst removal composition 200 was analyzed for IPA content.

In experiments 2 and 3, cooled carboxylic acid composition Stream 170 slurry was charged to a bench scale Pannevis vacuum filter and the resulting wet cake was washed with wash feed stream 175 and the post catalyst removal composition stream 200 was analyzed for IPA content. The wash feed stream 175 contained 90% acetic acid and 10% water by weight.

In experiments 4 and 5 the cooled carboxylic acid composition stream 170 slurry was charged to a bench scale Pannevis vacuum filter and the resulting wet cake was washed with hot wash feed Stream 175. The resulting post catalyst removal composition stream 200 wet cake was then washed with an enrichment feed stream 220 and resulting enriched carboxylic acid composition was analyzed for IPA content. Both the catalyst removal Zone 180 and the enrichment Zone 210 were accomplished with the bench scale Pannevis vacuum filter apparatus.

The enrichment feed Stream 220 used in experiments 4 and 5 were prepared in this matter. Acetic acid was heated to 80° C. and enough IPA was added until the IPA would no longer go into solution.

Experiment 1 (No Cake Wash, No Enrichment Wash)

401.67 grams of the cooled carboxylic acid stream 170 at 23.9° C. was fed to the catalyst removal zone 180 which was a bench scale Pannevis vacuum filter. There was no wash feed stream 175. The stream 200 wet cake weight was 145.55 grams and the % solids was 89.4%. A sample of the wet cake was submitted to analytical for IPA analyses.

Experiment 2 (80° C. Cake Wash, No Enrichment Wash)

400.33 grams of the cooled carboxylic acid composition stream 170 slurry at 29.3° C. was fed to the catalyst removal zone 180 which was a bench scale Pannevis vacuum filter. The filter cake was washed with 100.11 grams of 80.2° C. wash feed stream 175. The resulting post catalyst removal stream 200 weight was 139.49 g and the % solids was 99.94%. Samples from the post catalyst removal composition 200 were submitted to analytical for IPA analyses.

Experiment 3 (80° C. Cake Wash, No Enrichment Wash)

401.17 grams of the cooled carboxylic acid composition stream 170 at 24° C. was fed to the catalyst removal zone 180 which was a bench scale Pannevis vacuum filter. The filter cake was washed with 100.05 grams of 80.0° C. wash feed stream 175. The resulting post catalyst removal composition weight was 124.07 grams and the % solids was 99.95%. A sample of the post catalyst removal composition 200 was submitted to analytical for IPA analyses.

Experiment 4 (80° C. Cake Wash, 80° C. Enrichment Wash)

400.45 grams of the cooled carboxylic acid composition stream 170 at 24.3° C. was fed to the catalyst removal Zone 180 which was a bench scale Pannevis vacuum filter. The filter cake was washed with 100.11 grams of 80.1 C wash feed stream 175. The wet cake was then enriched with 100.52 gms of 80.2° C. enrichment feed stream 220. The resulting enriched carboxylic acid composition stream 240 weight was 131.33 grams and the % solids were 99.9%. Samples from enriched carboxylic acid composition stream 240 was submitted to analytical for IPA analyses.

Experiment 5 (80° C. Cake Wash, 80° C. Enrichment Wash)

400.55 grams of the cooled carboxylic acid composition stream 170 at 24.4° C. was fed to the catalyst removal zone 180 which was a bench scale Pannevis vacuum filter. The filter cake was washed with 100.28 grams of 80.2° C. wash feed stream 175. The wet cake was then enriched with 100.54 gms of 80.0° C. enrichment feed stream 220. The resulting enriched carboxylic acid composition stream 240 weight was 144.54 grams and the % solids were 98.8%. Samples from enriched carboxylic acid composition stream 240 were submitted to analytical for IPA analyses.

| Results | |
|---|---|
| Experiment # | Ppm IPA |
| 1 | 2199 |
| 2 | 1087 |
| 3 | 804 |
| 4 | 4676 |
| 5 | 5535 |

In experiment 1 the wet cake is not washed resulting in a concentration of 2199 ppm IPA. In experiments 2 and 3, the wet cake is wash with stream 175 producing a post catalyst composition 200 with an average IPA concentration of about 900 ppm. In experiments 4 and 5 the post catalyst composition 200 is enriched with an enrichment stream 220 to produce an enriched carboxylic composition 240 with an average IPA concentration of about 5000 ppm. It is clear from this data that IPA was enriched in stream 240 to a concentration above that of the post catalyst composition. This data illustrates oxidation by-product enrichment in an enrichment zone utilizing IPA as an example. IPA is considered representative of other oxidation by-products in that the retention of other oxidation by-products in the catalyst removal zone can be influenced by the wash conditions, including the wash ratio, wash solvent composition, and wash temperature, as well as the cake thickness and the particle size distribution which affects the cake porosity.

We claim:

1. A process to produce and recycle an enrichment feed, said process comprising:
    (a) subjecting a catalyst rich liquor produced in a terephthalic acid production process to a cooling and/or concentration zone to form a concentrated mother liquor stream; wherein said catalyst rich liquor comprises at least one solvent, at least one catalyst; wherein said catalyst was previously utilized in the oxidation of paraxylene;
    (b) subjecting at least a portion of said concentrated mother liquor stream and an extraction solvent to an extraction zone to form a catalyst depleted stream;
    (c) subjecting—the balance of said concentrated mother liquor stream not sent to said extraction zone and a wash stream in a SLS zone to form a wet cake stream; wherein said wash stream is any stream suitable for removing a portion of said catalyst from solids isolated in said SLS zone to produce said wet cake stream;
    (d) subjecting at least a portion of said wet cake stream and optionally said catalyst depleted stream to a mix zone to form said enrichment feed; wherein said enrichment feed comprises at least one compound selected from the group consisting of isophthalic acid, phthalic acid, benzene-tricarboxylic acid isomers, hydroxybenzoic acid isomers, hydroxymethylbenzoic acid isomers, dicarboxybiphenyl isomers, dicarboxystilbene isomers, tricarboxybiphenyl isomers, tricarboxybenzophenone isomers, dicarboxybenzophenone isomers, dicarboxybenzil isomers, form-acet-hydroxybenzoic acid isomers, acet-hydroxymethylbenzoic acid isomers and phthaldehyde isomers; and
    (e) recycling at least a portion of said enrichment feed to any point in a TPA production process after a primary oxidation zone and before the isolation of a dried TPA product.

2. The process according to claim 1 wherein said concentrated mother liquor stream has a solid content ranging from 10% by weight to 45% by weight.

3. The process according to claim 1 wherein said concentrated mother liquor stream has a solid content ranging from 10% by weight to 30% by weight.

4. The process according to claim 1 wherein said extraction zone comprises at least one extractor operated at a temperature of 30° C. to 70° C.

5. The process according to claim 2 wherein said extraction zone comprises at least one extractor operated at a temperature of 30° C. to 70° C.

6. The process according to claim 1 wherein said extraction zone comprises at least one extractor; wherein the solvent ratio for said extractor is 1 to 4 parts by weight solvent per part extractor feed.

7. The process according to claim 1 wherein said extraction zone comprises at least one extractor; wherein the space velocities for the combined feed to said extractor range from 1 to about 3 hr$^{-1}$.

8. The process according to claim 1 wherein said extraction solvent comprises at least one solvent selected from the group consisting of N-propyl acetate (n-PA), isopropyl acetate, isobutyl acetate, sec-butyl acetate, ethyl acetate, and n-butyl acetate.

9. The process according to claim 1 wherein said extraction solvent comprises at least one solvent selected from the group consisting of N-propyl acetate and isopropyl acetate.

* * * * *